US009107956B2

(12) United States Patent
Riggs-Sauthier et al.

(10) Patent No.: US 9,107,956 B2
(45) Date of Patent: Aug. 18, 2015

(54) OLIGOMER-PROTEASE INHIBITOR CONJUGATES

(71) Applicant: NEKTAR THERAPEUTICS, San Francisco, CA (US)

(72) Inventors: Jennifer Riggs-Sauthier, San Francisco, CA (US); Lin Cheng, Millbrae, CA (US); Tacey X. Viegas, Madison, AL (US); Xuyuan Gu, Foster City, CA (US); Franco J. Duarte, Huntsville, AL (US); Wen Zhang, Dublin, CA (US)

(73) Assignee: NEKTAR THERAPEUTICS, San Francisco, CA (US)

( * ) Notice: Subject to any disclaimer, the term of this patent is extended or adjusted under 35 U.S.C. 154(b) by 0 days.

(21) Appl. No.: 14/055,581

(22) Filed: Oct. 16, 2013

(65) Prior Publication Data
US 2014/0045770 A1  Feb. 13, 2014

Related U.S. Application Data

(62) Division of application No. 12/530,363, filed as application No. PCT/US2008/003354 on Mar. 12, 2008, now Pat. No. 8,598,364.

(60) Provisional application No. 60/906,330, filed on Mar. 12, 2007.

(51) Int. Cl.
A61K 47/48 (2006.01)
(52) U.S. Cl.
CPC ................................ A61K 47/48215 (2013.01)
(58) Field of Classification Search
CPC ............................................. A61K 47/48215
USPC .............. 514/20.1, 336; 546/146, 282.1, 332; 549/464
See application file for complete search history.

(56) References Cited

U.S. PATENT DOCUMENTS

| | | |
|---|---|---|
| 5,149,794 A | 9/1992 | Yatkin et al. |
| 5,196,438 A | 3/1993 | Martin et al. |
| 5,413,999 A | 5/1995 | Vacca et al. |
| 5,484,926 A | 1/1996 | Dressman et al. |
| 5,585,397 A | 12/1996 | Tung et al. |
| 5,672,662 A | 9/1997 | Harris et al. |
| 5,732,490 A | 3/1998 | Hydary |
| 5,849,911 A | 12/1998 | Fassler et al. |
| 5,852,195 A | 12/1998 | Romines et al. |
| 6,147,095 A | 11/2000 | Ferry et al. |
| 6,231,887 B1 | 5/2001 | Gao et al. |
| 6,436,989 B1 | 8/2002 | Hale et al. |
| 6,458,818 B1 | 10/2002 | Lipari et al. |
| 6,514,953 B1 | 2/2003 | Armitage et al. |
| 6,765,019 B1 | 7/2004 | Crooks et al. |
| 6,992,177 B1 | 1/2006 | Hui et al. |
| 8,012,488 B2 | 9/2011 | Sakanoue et al. |
| 2004/0127689 A1 | 7/2004 | Sigler et al. |
| 2004/0223948 A1 | 11/2004 | Ekwuribe et al. |
| 2005/0136031 A1 | 6/2005 | Bentley et al. |
| 2011/0195912 A1 | 8/2011 | Riggs-Sauthier et al. |
| 2011/0269677 A1 | 11/2011 | Riggs-Sauthier et al. |
| 2012/0108501 A1 | 5/2012 | Riggs-Sauthier |

FOREIGN PATENT DOCUMENTS

| | | |
|---|---|---|
| EP | 580 402 | 1/1994 |
| EP | 560 268 | 1/1995 |
| EP | 541 168 | 3/1998 |
| FR | 2 773 994 | 7/1999 |
| WO | WO 93/07128 | 4/1993 |
| WO | WO 93/23368 | 11/1993 |
| WO | WO 95/06061 | 3/1995 |
| WO | WO 95/09843 | 4/1995 |
| WO | WO 95/30670 | 11/1995 |
| WO | WO 97/21685 | 6/1997 |
| WO | WO 99/33815 | 7/1999 |
| WO | WO 02/098949 | 12/2002 |
| WO | WO 2005/000360 | 1/2005 |
| WO | WO 2005/124563 | 12/2005 |
| WO | WO 2006/089156 | 8/2006 |

OTHER PUBLICATIONS

Bachmeier, et al., "Quantitative Assessment of HIV-1 Protease Inhibitor Interactions with Drug Efflux Transporters in the Blood-Brain Barrier", Pharm. Res., vol. 22, No. 8, pp. 1259-1268, (Aug. 2005).

Chen, et al., "Synthesis and Properties of ABA Amphiphiles", J. Org. Chem., vol. 64, pp. 6870-6873, (1999).

Giorgio, et al, "Synthesis and anti-HIV activity of prodrugs derived from saquinavir and indinavir", Antiviral Chemistry and Chemo Therapy, vol. 11, No. 2, pp. 97-110, (2000).

Gunaseelan, et al., "Synthesis of Poly(ethylene glycol)-Based Saquinavir Prodrug Conjugates and Assessment of Release and Anti-HIV-1 Bioactivity Using a Novel Protease Inhibition Assay", Bioconjugate, Chem., vol. 15, pp. 1322-1333, (2004).

Hammer, et al., "Treatment for Adult HIV Infection: 2006 Recommendations of the International Aids Society—USA Panel", JAMA, vol. 296, No. 7, pp. 827-843, (2006).

Kempf, et al., "Antiviral and Pharmacokinetic Properties of C2 Symmetric Inhibitors of the Human Immunodeficiency Virus Type 1 Protease", Antimicrob. Agents and Chemotherp., vol. 35, No. 11, pp. 2209-2214, (Nov. 1991).

McQuade, et al., "A Synthetic HIV-1 Protease Inhibitor with Antiviral Activity Arrests HIV-Like Particle Maturation", Science, vol. 247, pp. 454-456, (Jan. 26, 1990).

(Continued)

*Primary Examiner* — Sean Basquill
(74) *Attorney, Agent, or Firm* — Mark A. Wilson

(57) ABSTRACT

The invention provides small molecule drugs that are chemically modified by covalent attachment of a water-soluble oligomer. A conjugate of the invention, when administered by any of a number of administration routes, exhibits characteristics that are different from the small molecule drug not attached to the water-soluble oligomer.

13 Claims, No Drawings

(56) References Cited

OTHER PUBLICATIONS

Pauwels, et al., "Rapid and automated tetrazolium-based colorimetric assay for the detection of anti-HIV compounds", J. of Virological Methods, vol. 20, pp. 309-321, (1988).
Rouquayrol, et al., "Synthesis and anti-HIV activity of glucose-containing prodrugs derived from saquinavir, indinavir and nelfinavir", Carbohy. Res., vol. 336, pp. 161-180, (2001).
Rouquayrol, et al., "Transepithelial Transport of Prodrugs of the HIV Protease Inhibitors Saquinavir, Indinavir, and Nelfinavir across Caco-2 Cell Monolayers", Pharm. Res., vol. 19, No. 11, pp. 1704-1712, (Nov. 2002).
Wan, et al., "Novel multi-component nanopharmaceuticals derived from poly(ethylene) glycol, retro-inverso-Tat nonapeptide and saquinavir demonstrate combined anti-HIV effects", AIDS Res. And Therp., 3:12, pp. 1-15, (2006).
Center for Disease Control and Prevention, MMWR, vol. 55, No. 31, pp. 841-844, (Aug. 11, 2006).
PCT International Search Report in PCT Patent Application No. PCT/US2008/003354 date of mailing Nov. 6, 2008.
PCT International Preliminary Report on Patentability in PCT Patent Application No. PCT/US2008/003354 date of issuance of report Sep. 15, 2009.
Enzon Pharmaceuticals, Macromolecular Engineering Technologies, 16 pages, (2004).
NEKTAR™—Transforming Therapeutics, Nektar Molecule Engineering: Polyethylene Glycol and Derivatives for Advanced PEGylation, 24 pages, Catalog—2003, (Jul. 2003).
NEKTAR™—Transforming Therapeutics, Nektar Advanced PEGylation: Polyethylene Glycol and Derivatives for Advanced PEGylation, 27 pages, Catalog—2004, (Jul. 2004).
NEKTAR™—Transforming Therapeutics, Nektar Advanced PEGylation: Polyethylene Glycol and Derivatives for Advanced PEGylation, 33 pages, (Catalog 2005—2006).
NOF Corporation, PEG Derivatives, Phospholipid and Drug Delivery Materials for Pharmaceuticals, 46 pages, Catalogue 2003-$1^{st}$, (Jan. 2003).
NOF Corporation, PEG Derivatives, Phospholipid and Drug Delivery Materials for Pharmaceuticals, 27 pages, Catalogue 2003-$2^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; Biotins, 5 pages, (Apr. 2004).
Polypure Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
Examiner's First Report corresponding to Australian Patent Application No. 2008226823 dated May 23, 2012.
Notification of the First Office Action corresponding to Chinese Patent Application No. 200880007943.X dated Apr. 21, 2011.
Notification of the Second Office Action corresponding to Chinese Patent Application No. 200880007943.X dated Dec. 6, 2011.
Examination Report corresponding to European Patent Application No. 08 742 083.2-1216 dated Jul. 26, 2010.
Office Communication corresponding to European Patent Application No. 08 742 083.2-1216 dated Jul. 5, 2012.
Office Communication with extended European Search Report corresponding to European Patent Application No. 12178362.5-1216 dated Oct. 11, 2012.
First Substantive Examination Report corresponding to Israeli Patent Application No. 200846 dated Feb. 23, 2012.
Office Action corresponding to Mexican Patent Application No. MX/a/2009/009850 dated Mar. 23, 2012.
Shuman, et al., "Improved Structure-Activity Relationship Analysis of HIV-1 Protease Inhibitors Using Interaction Kinetic Data", J. Med. Chem., vol. 47, pp. 5953-5961, (2004).
Surleraux, et al., "Design of HIV-1 Protease Inhibitors Active on Multidrug-Resistant Virus", J. Med. Chem., vol. 48, pp. 1965-1973, (2005).
Cynkowski, et al., "Synthesis and properties of novel prodrugs of saquinavir with short chain polyethylene glycols, polyoxa acids and amino acids", Database CAPLUS on STN, AN 1998:529831, Book of Abstracts, $216^{th}$ ACS National Meeting, (Aug. 1998).
Canadian Office Action corresponding to Canadian Patent Application No. 2,679,482 dated Jun. 26, 2013.
European Communication corresponding to European Patent Application No. 08 742 083.2 dated Jul. 1, 2013.
European Communication corresponding to European Patent Application No. 12 178 362.5 dated Jul. 11, 2013.
Japanese Notice of Reasons for Rejection corresponding to Japanese Patent Application No. 2009-553629 mailing date Mar. 6, 2013.
Japanese Notice of Reasons for Rejection corresponding to Japanese Patent Application No. 2009-553629 mailing date Aug. 15, 2013.
Mexican Official Letter corresponding to Mexican Patent Application No. MX/a/2009/009850 dated Mar. 27, 2013.
Canadian Office Communication corresponding to Canadian Patent Application No. 2,679,482 dated Apr. 14, 2014.
Chinese Notification of the First Office Action corresponding to Chinese Patent Application No. 201210257651.X date of notification Dec. 25, 2013.
European Communication corresponding to European Patent Application No. 12 178 362.5 dated Jun. 10, 2014.
Israel Communication corresponding to Israel Patent Application No. 200846 dated Sep. 30, 2013.
Indian First Examination Report corresponding to Indian Patent Application No. 5631/DELNP/2009 dated Nov. 26, 2014.
Korean Notice of Grounds for Rejection corresponding to Korean Patent Application No. 2009-7018914 issuance date Apr. 1, 2014.
Korean Notice of Final Rejection corresponding to Korean Patent Application No. 2009-7018914 issuance date Oct. 24, 2014.
Australian Patent Examination Report No. 2 corresponding to Australian Patent Application No. 2008226823 date of issue Feb. 10, 2014.
Japanese Notice of Reasons for Rejection corresponding to Japanese Patent Application No. 2013-233740 mailing date Oct. 14, 2014.
Mexican Official Letter corresponding to Mexican Patent Application No. MX/a/2009/009850 dated Dec. 12, 2013.

OLIGOMER-PROTEASE INHIBITOR CONJUGATES

CROSS REFERENCE TO RELATED APPLICATION

This application is a divisional application of U.S. patent application Ser. No. 12/530,363, filed Jun. 4, 2010, which application is a national phase filing under 35 U.S.C. §371 of International Patent Application No. PCT/US2008/003354, filed Mar. 12, 2008, which claims the benefit of priority under 35 U.S.C. §119(e) of U.S. Provisional Application Ser. No. 60/906,330, filed, Mar. 12, 2007, the disclosures of each of which are incorporated herein by reference.

FIELD OF THE INVENTION

This invention provides chemically modified small molecule protease inhibitors that possess certain advantages over small molecule protease inhibitors lacking the chemical modification. The chemically modified small molecule protease inhibitors described herein relate to and/or have application(s) in (among others) the fields of drug discovery, pharmacotherapy, physiology, organic chemistry and polymer chemistry.

BACKGROUND OF THE INVENTION

Since the first cases of acquired immunodeficiency syndrome (AIDS) were reported in 1981, infection with human immunodeficiency virus (HIV) has grown to pandemic proportions, resulting in an estimated 65 million infections and 25 million deaths. See Aug. 11, 2006, *MMWR* 55(31):841-844 (Center for Disease Control and Prevention). Protease inhibitors represent an important class of compounds used to treat individuals infected with HIV, although these compounds can also treat individuals suffering from other viral infections (e.g., Hepatitis C).

With respect to HIV, protease inhibitors act to inhibit the viral proteases that are necessary for the proteolytic cleavage of the gag and gag/pol fusion polypeptides necessary for the generation of infective viral particles. Thus, by inhibiting this proteolytic cleavage, protease inhibitors diminish the ability of larger HIV-fusion polypeptide precursors to from the mature form of protein necessary for effective viral replication. McQuade et al. (1990) *Science* 247(4941):454-456.

Protease inhibitor-based therapy is acknowledged as an initial treatment for patients presenting symptomatic HIV disease and in non-symptomatic patients after the CD4 cell count is below 350/µL but before a level of 200/µL. Hammer et al. (2006) *JAMA* 296(7):827-843. In such cases, a protease inhibitor-based regimen will include a protease inhibitor (typically boosted with ritonavir) along with a combination of two nucleoside (or nucleotide) reverse transcriptase inhibitors. Id.

Although protease inhibitors serve an important role in treating patients suffering from HIV, their use has been hampered by challenges associated with (among other things) extremely poor aqueous solubility and extensive metabolism. One approach suggested to address these drawbacks includes preparing prodrug forms of protease inhibitors, such as acyl and carbamotoyl glucose-containing prodrugs (Rouquayrol et al. (2001) *Carbohydr. Res.* 336:161-180) and relatively large PEG-based prodrugs (Gunaseelan et al. (2004) *Bioconjugate Chem.* 15:1322-1333). Although potentially addressing some of the disadvantages associated with protease inhibitors, prodrug approaches necessarily result in the return of the original molecule, often along with its associated drawbacks. For example, it is not believed that a prodrug approach would adequately solve the problems associated the extensive metabolism typically observed with protease inhibitors.

The present invention seeks to address this and other needs in the art.

SUMMARY OF THE INVENTION

In one or more embodiments, a compound is provided, the compound comprising a residue of a protease inhibitor covalently attached, either directly or through one or more atoms, via a stable linkage to a water-soluble, non-peptidic oligomer.

In one or more embodiments, a compound is provided, the compound comprising a residue of a protease inhibitor covalently attached, either directly or through one or more atoms, via a stable linkage to a water-soluble, non-peptidic oligomer, wherein the protease inhibitor is encompassed by Formula I.

In one or more embodiments, a compound is provided, the compound comprising a residue of a protease inhibitor covalently attached, either directly or through one or more atoms, via a stable linkage to a water-soluble, non-peptidic oligomer, wherein the protease inhibitor is encompassed by Formula II.

In one or more embodiments, a compound is provided, the compound comprising a residue of a protease inhibitor covalently attached, either directly or through one or more atoms, via a stable linkage to a water-soluble, non-peptidic oligomer, wherein the protease inhibitor is encompassed by Formula III.

In one or more embodiments, a compound is provided, the compound comprising a residue of a protease inhibitor covalently attached, either directly or through one or more atoms, via a stable linkage to a water-soluble, non-peptidic oligomer, wherein the protease inhibitor is encompassed by Formula IV.

In one or more embodiments, a compound is provided, the compound comprising a residue of a protease inhibitor covalently attached, either directly or through one or more atoms, via a stable linkage to a water-soluble, non-peptidic oligomer, wherein the protease inhibitor is encompassed by Formula V.

In one or more embodiments, a compound is provided, the compound comprising a residue of a protease inhibitor covalently attached, either directly or through one or more atoms, via a stable linkage to a water-soluble, non-peptidic oligomer, wherein the protease inhibitor is encompassed by Formula VI.

In one or more embodiments, a compound is provided, the compound comprising a residue of a protease inhibitor covalently attached, either directly or through one or more atoms, via a stable linkage to a water-soluble, non-peptidic oligomer, wherein the protease inhibitor is encompassed by Formula VII.

In one or more embodiments, a compound is provided, the compound having the following structure:

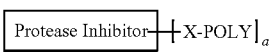

wherein:

[Protease Inhibitor]

is a residue of a small molecule protease inhibitor;
(a) is an integer having a value of one to three, inclusive;
X, in each occurrence, is a stable linkage; and
POLY, in each occurrence, is a water-soluble, non-peptidic oligomer.

In one or more embodiments of the invention, a composition is provided, the composition comprising: a compound comprising a residue of a protease inhibitor covalently attached, either directly or through one or more atoms, via a stable linkage to a water-soluble, non-peptidic oligomer; and, optionally, a pharmaceutically acceptable excipient.

In one or more embodiments of the invention, a composition is provided, the composition comprising:
(i) a compound having the following structure:

[Protease Inhibitor]—[X-POLY]$_a$ wherein:

[Protease Inhibitor]

is a residue of a small molecule protease inhibitor;
(a) is an integer having a value of one to three, inclusive;
X, in each occurrence is a stable linkage; and
POLY, in each occurrence, is a water-soluble, non-peptidic oligomer; and
(ii) optionally, a pharmaceutically acceptable excipient.

In one or more embodiments of the invention, a dosage form is provided, the dosage form comprising a compound comprising a residue of a protease inhibitor covalently attached, either directly or through one or more atoms, via a stable linkage to a water-soluble, non-peptidic oligomer.

In one or more embodiments of the invention, a dosage form is provided, the dosage form comprising a compound having the following structure:

[Protease Inhibitor]—[X-POLY]$_a$ wherein:

[Protease Inhibitor]

is a residue of a small molecule protease inhibitor;
(a) is an integer having a value of one to three, inclusive;
X, in each occurrence is a stable linkage; and
POLY, in each occurrence, is a water-soluble, non-peptidic oligomer.

In one or more embodiments of the invention, a method is provided, the method comprising covalently attaching a water-soluble, non-peptidic oligomer to a small molecule protease inhibitor.

In one or more embodiments of the invention, a method is provided, the method comprising administering a compound having the following structure:

[Protease Inhibitor]—[X-POLY]$_a$ wherein:

[Protease Inhibitor]

is a residue of a small molecule protease inhibitor;
(a) is an integer having a value of one to three, inclusive;
X, in each occurrence, is a stable linkage; and
POLY, in each occurrence, is a water-soluble, non-peptidic oligomer; and
(ii) optionally, a pharmaceutically acceptable excipient.

These and other objects, aspects, embodiments and features of the invention will become more fully apparent when read in conjunction with the following detailed description.

DETAILED DESCRIPTION OF THE INVENTION

As used in this specification, the singular forms "a," "an," and "the" include plural referents unless the context clearly dictates otherwise.

In describing and claiming the present invention, the following terminology will be used in accordance with the definitions described below.

"Water soluble, non-peptidic oligomer" indicates an oligomer that is at least 35% (by weight) soluble, preferably greater than 70% (by weight), and more preferably greater than 95% (by weight) soluble, in water at room temperature. Typically, an unfiltered aqueous preparation of a "water-soluble" oligomer transmits at least 75%, more preferably at least 95%, of the amount of light transmitted by the same solution after filtering. It is most preferred, however, that the water-soluble oligomer is at least 95% (by weight) soluble in water or completely soluble in water. With respect to being "non-peptidic," an oligomer is non-peptidic when it has less than 35% (by weight) of amino acid residues.

The terms "monomer," "monomeric subunit" and "monomeric unit" are used interchangeably herein and refer to one of the basic structural units of a polymer or oligomer. In the case of a homo-oligomer, a single repeating structural unit forms the oligomer. In the case of a co-oligomer, two or more structural units are repeated—either in a pattern or randomly—to form the oligomer. Preferred oligomers used in connection with present the invention are homo-oligomers. The water-soluble, non-peptidic oligomer typically comprises one or more monomers serially attached to form a chain of monomers. The oligomer can be formed from a single monomer type (i.e., is homo-oligomeric) or two or three monomer types (i.e., is co-oligomeric).

An "oligomer" is a molecule possessing from about 2 to about 50 monomers, preferably from about 2 to about 30 monomers. The architecture of an oligomer can vary. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" (also called an oligoethylene glycol) is one in which substantially all (and more preferably all) monomeric subunits are ethylene oxide subunits. The oligomer may, however, contain distinct end capping moieties or functional groups, e.g., for conjugation. Typically, PEG oligomers for use in the present invention will comprise one of the two following structures: "—(CH$_2$CH$_2$O)$_n$—" or "—(CH$_2$CH$_2$O)$_{n-1}$CH$_2$CH$_2$—," depending upon whether the terminal oxygen(s) has been displaced, e.g., during a synthetic transformation. For PEG oligomers, "n" varies from about 2 to 50, preferably from about 2 to about 30, and the terminal groups and architecture of the overall PEG can vary. When PEG further comprises a functional group, A, for linking to, e.g., a small molecule drug, the functional group when covalently attached to a PEG oligomer does not result in formation of (i) an oxygen-oxygen bond (—O—O—, a peroxide linkage), or (ii) a nitrogen-oxygen bond (N—O, O—N).

An "end capping group" is generally a non-reactive carbon-containing group attached to a terminal oxygen of a PEG oligomer. Exemplary end capping groups comprise a C$_{1-5}$ alkyl group, such as methyl, ethyl and benzyl), as well as aryl, heteroaryl, cyclo, heterocyclo, and the like. For the purposes of the present invention, the preferred capping groups have relatively low molecular weights such as methyl or ethyl. The end-capping group can also comprise a detectable label. Such labels include, without limitation, fluorescers, chemiluminescers, moieties used in enzyme labeling, colorimetric labels (e.g., dyes), metal ions, and radioactive moieties.

"Branched", in reference to the geometry or overall structure of an oligomer, refers to an oligomer having two or more polymers representing distinct "arms" that extend from a branch point.

"Forked" in reference to the geometry or overall structure of an oligomer, refers to an oligomer having two or more functional groups (typically through one or more atoms) extending from a branch point.

A "branch point" refers to a bifurcation point comprising one or more atoms at which an oligomer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof encompasses protected forms thereof.

A "physiologically cleavable" or "hydrolyzable" or "degradable" bond is a relatively labile bond that reacts with water (i.e., is hydrolyzed) under ordinary physiological conditions. The tendency of a bond to hydrolyze in water under ordinary physiological conditions will depend not only on the general type of linkage connecting two central atoms but also on the substituents attached to these central atoms. Such bonds are generally recognizable by those of ordinary skill in the art. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, and carbonates.

An "enzymatically degradable linkage" means a linkage that is subject to degradation by one or more enzymes under ordinary physiological conditions.

A "stable" linkage or bond refers to a chemical moiety or bond, typically a covalent bond, that is substantially stable in water, that is to say, does not undergo hydrolysis under ordinary physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under ordinary physiological conditions. Hydrolysis rates of representative chemical bonds can be found in most standard chemistry textbooks.

In the context of describing the consistency of oligomers in a given composition, "substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Monodisperse" refers to an oligomer composition wherein substantially all of the oligomers in the composition have a well-defined, single molecular weight and defined number of monomers, as determined by chromatography or mass spectrometry. Monodisperse oligomer compositions are in one sense pure, that is, substantially comprising molecules having a single and definable number of monomers rather than several different numbers of monomers (i.e., an oligomer composition having three or more different oligomer sizes). A monodisperse oligomer composition possesses a MW/Mn value of 1.0005 or less, and more preferably, a MW/Mn value of 1.0000. By extension, a composition comprised of monodisperse conjugates means that substantially all oligomers of all conjugates in the composition have a single and definable number (as a whole number) of monomers rather than a distribution and would possess a MW/Mn value of 1.0005, and more preferably, a MW/Mn value of 1.0000 if the oligomer were not attached to the residue of the small molecule protease inhibitor. A composition comprised of monodisperse conjugates can include, however, one or more nonconjugate substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a distribution, and whose distribution of molecular weights, when plotted as a number fraction versus molecular weight, appears as two separate identifiable peaks. Preferably, for a bimodal oligomer composition as described herein, each peak is generally symmetric about its mean, although the size of the two peaks may differ. Ideally, the polydispersity index of each peak in the bimodal distribution, Mw/Mn, is 1.01 or less, more preferably 1.001 or less, and even more preferably 1.0005 or less, and most preferably a MW/Mn value of 1.0000. By extension, a composition comprised of bimodal conjugates means that substantially all oligomers of all conjugates in the composition have one of two definable and different numbers (as whole numbers) of monomers rather than a large distribution and would possess a MW/Mn value of 1.01 or less, more preferably 1.001 or less and even more preferably 1.0005 or less, and most preferably a MW/Mn value of 1.0000 if the oligomer were not attached to the residue of the small molecule protease inhibitor agonist. A composition comprised of bimodal conjugates can include, however, one or more nonconjugate substances such as solvents, reagents, excipients, and so forth.

A "small molecule protease inhibitor" is broadly used herein to refer to an organic, inorganic, or organometallic compound typically having a molecular weight of less than about 1000 and having some degree of activity as a retroviral protease inhibitor. Small molecule protease inhibitors encompass oligopeptides and other biomolecules having a molecular weight of less than about 1000.

A "biological membrane" is any membrane, typically made from specialized cells or tissues, that serves as a barrier to at least some foreign entities or otherwise undesirable materials. As used herein a "biological membrane" includes those membranes that are associated with physiological protective barriers including, for example: the blood-brain barrier (BBB); the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, rectal mucosa, and so forth. Unless the context clearly dictates otherwise, the term "biological membrane" does not include those membranes associated with the middle gastro-intestinal tract (e.g., stomach and small intestines).

A "biological membrane crossing rate," as used herein, provides a measure of a compound's ability to cross a biological membrane (such as the membrane associated with the blood-brain barrier). A variety of methods can be used to assess transport of a molecule across any given biological membrane. Methods to assess the biological membrane crossing rate associated with any given biological barrier (e.g., the blood-cerebrospinal fluid barrier, the blood-placental barrier, the blood-milk barrier, the intestinal barrier, and so forth), are known in the art, described herein and/or in the relevant literature, and/or can be determined by one of ordinary skill in the art.

A "reduced rate of metabolism" in reference to the present invention, refers to a measurable reduction in the rate of metabolism of a water-soluble oligomer-small molecule drug conjugate as compared to rate of metabolism of the small molecule drug not attached to the water-soluble oligomer (i.e., the small molecule drug itself) or a reference standard material. In the special case of "reduced first pass rate of metabolism," the same "reduced rate of metabolism" is required except that the small molecule drug (or reference standard material) and the corresponding conjugate are administered orally. Orally administered drugs are absorbed from the gastro-intestinal tract into the portal circulation and must pass through the liver prior to reaching the systemic circulation. Because the liver is the primary site of drug metabolism or biotransformation, a substantial amount of drug can be metabolized before it ever reaches the systemic circulation. The degree of first pass metabolism, and thus, any reduction thereof, can be measured by a number of different approaches. For instance, animal blood samples can be collected at timed intervals and the plasma or serum analyzed by liquid chromatography/mass spectrometry for metabolite levels. Other techniques for measuring a "reduced rate of metabolism" associated with the first pass metabolism and other metabolic processes are known in the art, described herein and/or in the relevant literature, and/or can be determined by one of ordinary skill in the art. Preferably, a conjugate of the invention can provide a reduced rate of metabolism reduction satisfying at least one of the following values: at least about 30%; at least about 40%; at least about 50%; at least about 60%; at least about 70%; at least about 80%; and at least about 90%. A compound (such as a small molecule drug or conjugate thereof) that is "orally bioavailable" is one that preferably possesses a bioavailability when administered orally of greater than 25%, and preferably greater than 70%, where a compound's bioavailability is the fraction of administered drug that reaches the systemic circulation in unmetabolized form.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl when three or more carbon atoms are referenced. An "alkenyl" group is an alkyl of 2 to 20 carbon atoms with at least one carbon-carbon double bond.

The terms "substituted alkyl" or "substituted $C_{q-r}$ alkyl" where q and r are integers identifying the range of carbon atoms contained in the alkyl group, denotes the above alkyl groups that are substituted by one, two or three halo (e.g., F, Cl, Br, I), trifluoromethyl, hydroxy, $C_{1-7}$ alkyl (e.g., methyl, ethyl, n-propyl, isopropyl, butyl, t-butyl, and so forth), $C_{1-7}$ alkoxy, $C_{1-7}$ acyloxy, $C_{3-7}$ heterocyclic, amino, phenoxy, nitro, carboxy, carboxy, acyl, cyano. The substituted alkyl groups may be substituted once, twice or three times with the same or with different substituents.

"Lower alkyl" refers to an alkyl group containing from 1 to 6 carbon atoms, and may be straight chain or branched, as exemplified by methyl, ethyl, n-butyl, i-butyl, t-butyl. "Lower alkenyl" refers to a lower alkyl group of 2 to 6 carbon atoms having at least one carbon-carbon double bond.

"Non-interfering substituents" are those groups that, when present in a molecule, are typically non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, benzyl, etc.), preferably $C_1$-$C_7$.

"Pharmaceutically acceptable excipient" or "pharmaceutically acceptable carrier" refers to component that can be included in the compositions of the invention in order to provide for a composition that has an advantage (e.g., more suited for administration to a patient) over a composition lacking the component and that is recognized as not causing significant adverse toxicological effects to a patient.

The term "aryl" means an aromatic group having up to 14 carbon atoms. Aryl groups include phenyl, naphthyl, biphenyl, phenanthrenyl, naphthacenyl, and the like. "Substituted phenyl" and "substituted aryl" denote a phenyl group and aryl group, respectively, substituted with one, two, three, four or five (e.g. 1-2, 1-3 or 1-4 substituents) chosen from halo (F, Cl, Br, I), hydroxy, hydroxy, cyano, nitro, alkyl (e.g., $C_{1-6}$ alkyl), alkoxy (e.g., $C_{1-6}$ alkoxy), benzyloxy, carboxy, aryl, and so forth.

An "aromatic-containing moiety" is a collection of atoms containing at least aryl and optionally one or more atoms. Suitable aromatic-containing moieties are described herein.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g., $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S).

"Pharmacologically effective amount," "physiologically effective amount," and "therapeutically effective amount" are used interchangeably herein to mean the amount of a water-soluble oligomer-small molecule drug conjugate present in a composition that is needed to provide a threshold level of active agent and/or conjugate in the bloodstream or in the target tissue. The precise amount will depend upon numerous factors, e.g., the particular active agent, the components and physical characteristics of the composition, intended patient population, patient considerations, and the like, and can readily be determined by one skilled in the art, based upon the information provided herein and available in the relevant literature.

A "difunctional" oligomer is an oligomer having two functional groups contained therein, typically at its termini. When the functional groups are the same, the oligomer is said to be homodifunctional. When the functional groups are different, the oligomer is said to be heterobifunctional.

A basic reactant or an acidic reactant described herein include neutral, charged, and any corresponding salt forms thereof.

The term "patient," refers to a living organism suffering from or prone to a condition that can be prevented or treated by administration of a conjugate as described herein, typically, but not necessarily, in the form of a water-soluble oligomer-small molecule drug conjugate, and includes both humans and animals.

"Optional" or "optionally" means that the subsequently described circumstance may but need not necessarily occur, so that the description includes instances where the circumstance occurs and instances where it does not.

As indicated above, the present invention is directed to (among other things) a compound comprising a residue of a protease inhibitor covalently attached, either directly or through one or more atoms, via a stable linkage to a water-soluble, non-peptidic oligomer.

The present invention also provides a compound having the following structure:

wherein:

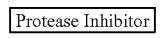

is a residue of a small molecule protease inhibitor;
(a) is an integer having a value of one to three, inclusive;
X, in each occurrence, is a stable linkage; and
POLY, in each occurrence, is a water-soluble, non-peptidic oligomer.

The compounds of the invention are conjugates of an oligomer and a protease inhibitor.

It is believed that an advantage of the conjugates of the present invention is their ability to retain some degree of protease activity while also exhibiting a decrease in metabolism. Although not wishing to be bound by theory, it is believed that the oligomer-containing conjugates described herein—in contrast to the unconjugated "original" protease inhibitor—are not metabolized as readily because the oligomer serves to reduce the overall affinity of the compound to substrates that can metabolize protease inhibitors.

As indicated above, the compounds of the invention include a residue of a small molecule protease inhibitor. The small molecule protease inhibitor is any small molecule that can reduce the activity of a retroviral protease. Assays for determining whether a compound (regardless of whether the compound is in conjugated form or not) is a protease inhibitor are described infra.

Known compounds that act as small molecule protease inhibitors include those selected from the following classes: azahexane derivatives; amino acid derivatives; non-peptidic derivatives; pyranone compounds; pentan-1-amine derivatives; hexan-2-ylcarbamate derivatives; sulfonamide derivatives; and tri-substituted phenyl derivatives. Other small molecule protease inhibitors not necessarily belonging to any of the foregoing classes can also be used.

With respect to azahexane derivatives that are small molecule protease inhibitors, preferred azahexane derivatives have the following formula:

(Formula I)

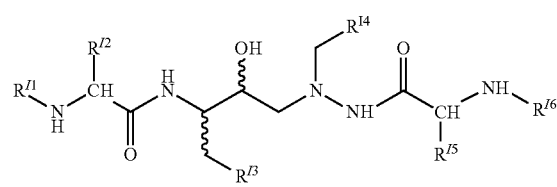

wherein:
$R^{I1}$ is lower alkoxycarbonyl;
$R^{I2}$ is secondary or tertiary lower alkyl or lower alkylthio-lower alkyl;

$R^{I3}$ is phenyl that is unsubstituted or substituted by one or more lower alkoxy radicals, or $C_{4-8}$ cycloalkyl;

$R^{I4}$ is phenyl or cyclohexyl, each substituted in the 4-position by unsaturated heterocyclyl that is bonded by way of a ring carbon atom, has from 5 to 8 ring atoms, contains from 1 to 4 hetero atoms selected from the group nitrogen, oxygen, sulfur, sulfinyl (—SO—), and sulfonyl (—SO$_2$—) and is unsubstituted or substituted by lower alkyl or by phenyl-lower alkyl;

$R^{I5}$ is secondary or tertiary lower alkyl or lower alkylthio-lower alkyl; and $R^{I6}$ is lower alkoxycarbonyl, and salts thereof.

A particularly preferred azahexane derivative is a compound of the following formula:

which is also known as atazanavir. Atazanavir and other azahexane derivatives, as well as methods for their synthesis, are described in U.S. Pat. No. 5,849,911.

With respect to amino acid derivatives that are small molecule protease inhibitors, preferred amino acid derivatives have the following formula:

(Formula II)

wherein:

$R^{II1}$ is benzyloxycarbonyl or 2-quinolylcarbonyl, and pharmaceutically acceptable acid addition salts thereof. A particularly preferred amino acid derivative is a compound of Formula II wherein $R^{II1}$ is 2-quinolylcarbonyl, also known as saquinavir. Such amino acid derivatives, as well as methods for their synthesis, are described in U.S. Pat. No. 5,196,438.

With respect to non-peptidic derivatives that are small molecule protease inhibitors, preferred non-peptidic derivatives have the following structure:

(Formula III)

wherein:

$R^{III1}$ and $R^{III2}$ are independently selected from hydrogen, and substituted and unsubstituted alkyl and aryl, and $R^{III1}$ and $R^{III2}$ may form a ring with G;

$R^{III3}$ is selected from mercapto and substituted and unsubstituted alkoxyl, aryloxyl, thioether, amino, alkyl, cycloalkyl, saturated and partially saturated heterocycle, and aryl;

$R^{III4}$, $R^{III5}$, $R^{III6}$, $R^{III7}$, and $R^{III8}$ are independently selected from hydrogen, hydroxyl, mercapto, nitro, halo, —O-J, wherein J is a substituted or unsubstituted hydrolyzable group, and substituted and unsubstituted alkoxyl, aryloxyl, thioether, acyl, sulfinyl, sulfonyl, amino, alkyl, cycloalkyl, saturated and partially saturated heterocycle and aryl, and further wherein any of $R^{III4}$, $R^{III5}$, $R^{III6}$, $R^{III7}$, and $R^{III8}$ may be a member of a spiro ring and any two of $R^{III4}$, $R^{III5}$, $R^{III6}$, $R^{III7}$, and $R^{III8}$ may together be members of a ring;

Y and G are independently selected from oxygen, —NH, —N-alkyl, sulfur, selenium, and two hydrogen atoms, D is a carbon or nitrogen;

E is a carbon or nitrogen;

$R^{III9}$ is selected from hydrogen, halo, hydroxyl, mercapto, and substituted and unsubstituted alkoxyl, aryloxyl, thioether, amino, alkyl, and aryl, wherein $R^{III9}$ may form part of a ring;

A is a carbocycle or heterocycle, which is optionally further substituted, and

B is a carbocycle or heterocycle, which is optionally further substituted, or a pharmaceutically acceptable salt thereof.

A particularly preferred non-peptidic derivative that is a small molecule protease inhibitor is a compound of the following formula:

which is also known as nelfinavir. Nelfinavir and other non-peptidic derivatives, as well as methods for their synthesis, are described in U.S. Pat. No. 5,484,926 and WO 95/09843.

With respect to pyranone compounds that are small molecule protease inhibitors, preferred pyranone compounds have the following structure:

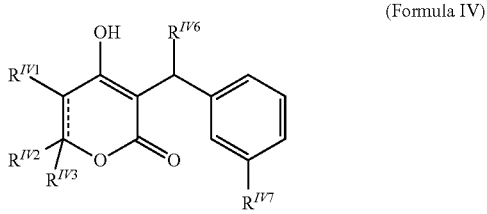

(Formula IV)

wherein:

$R^{IV4}$ is H; $R^{IV2}$ is $C_{3-5}$ alkyl, phenyl-$(CH_2)_2$—, heterocycyl-$SO_2NH$—$(CH_2)_2$—, cyclopropyl-$(CH_2)_2$—, F-phenyl-$(CH_2)_2$—, heterocycyl-$SO_2NH$-phenyl-, or $F_3C$—$(CH_2)_2$—; or $R^{IV1}$ and $R^{IV2}$ taken together are a double bond;

$R^{IV3}$ is $R^{IV4}$—$(CH_2)_n$—$CH(R^{IV5})$—, $H_3C$—[$O(CH_2)_2$]$_2$—$CH_2$—, $C_{3-5}$ alkyl, phenyl-$(CH_2)_2$—, heterocycyl-$SO_2NH$—$(CH_2)_2$—, $(HOCH_2)_3C$—$NH$—$C(O)$—$NH$—$(CH_2)_3$—, $(H_2C)(H_2N)CH$—$(CH_2)_2$—$C(O)$—$NH$—$(CH_2)_3$—, piperazin-1-yl-$C(O)$—$NH$—$(CH_2)_3$—, $HO_3S$—$(CH_2)_2$—$N(CH_3)$—$C(O)$—$(CH_2)_6$—$C(O)$—$NH$—$(CH_2)_3$—, cyclopropyl-$(CH_2)_2$—, F-phenyl-$(CH_2)_2$—, heterocycyl-$SO_2NH$-phenyl-, or $F_3$—$(CH_2)_2$—; n' is 0, 1 or 2; $R^{IV4}$ is phenyl, heterocycyl, cyclopropyl, $H_3C$—[O$(CH_2)_2$]$_2$—, heterocycyl-$SO_2NH$—, Br—, $N_3$—, or $HO_3S$—$(CH_2)_2$—$N(CH_3)$—$C(O)$—$(CH_2)_6$—$C(O)$—$NH$—; $R^{IV5}$ is —$CH_2$—$CH_3$, or —$CH_2$-cyclopropyl;

$R^{IV6}$ is cyclopropyl, $CH_3$—$CH_2$—, or t-butyl;

$R^{IV7}$ is —$NR^{IV8}SO_2$-heterocycyl, $NR^{IV8}SO_2$-phenyl, optionally substituted with $R^{IV9}$, or —$CH_2$—$SO_2$-phenyl, optionally substituted with $R^{IV9}$, or —$CH_2$—$SO_2$-heterocycyl; $R^{IV8}$ is H, or —$CH_3$; $R^{IV9}$ is —CN, —F, —OH, or —$NO_2$; wherein heterocycyl is a 5-, 6- or 7-membered saturated or unsaturated ring containing from one to three heteroatoms selected from the group consisting of nitrogen, oxygen and sulfur; and including any bicyclic group in which any of the above heterocyclic rings is fused to a benzene ring or another heterocycle, optionally substituted with —$CH_3$, —CN, —OH, —$C(O)OC_2H_5$, —$CF_3$, —$NH_2$, or —$C(O)$—$NH_2$; or a pharmaceutically acceptable salt thereof.

A particularly preferred pyranone compound that is a small molecule protease inhibitor is a compound of the following formula:

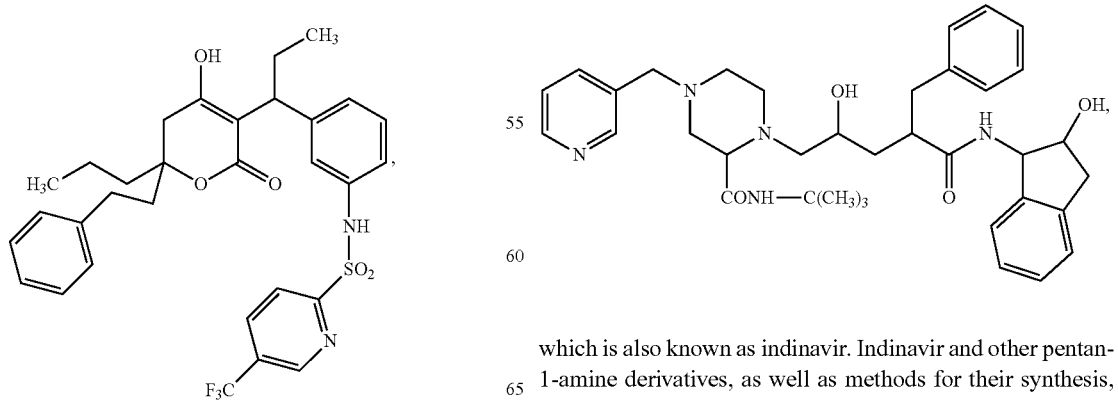

which is also known as tipranavir. Tipranavir and other non-peptidic derivatives, as well as methods for their synthesis, are described in U.S. Pat. Nos. 6,147,095, 6,231,887, and 5,484,926.

With respect to pentan-1-amine derivatives that are small molecule protease inhibitors, preferred pentan-1-amine derivatives have the following structure:

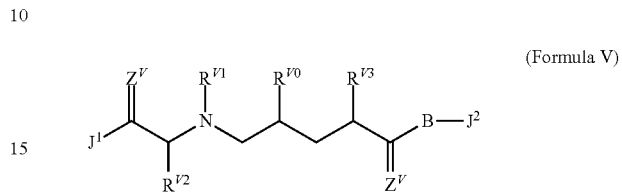

(Formula V)

wherein:

$R^{V0}$ is —OH or —$NH_2$;

$Z^V$, in each instance, is independently O, S, or NH;

$R^{V1}$ and $R^{V2}$ are independently hydrogen or optionally substituted $C_{1-4}$ alkyl, aryl, heterocycle, carbocyclic, —NH—$SO_2C_{1-3}$ alkyl, —O-aryl, —S-aryl, —NH-aryl, —O—$C(O)$-aryl, —S—$C(O)$-aryl, and —NH—$C(O)$-aryl, or $R^V1$ and $R^{V2}$ are joined together the form a monocyclic or bicyclic ring system;

$R^{V3}$ is hydrogen, $C_{1-4}$ alkyl, benzyl (substituted or unsubstituted);

$J^1$ and $J^2$ are independently —OH, —$NH_2$, or optionally substituted $C_{1-6}$ alkyl, aryl, heterocycle, and carbocyclic, and B is absent or selected from the group consisting of —NH—$CH(CH_3)_2$—$C(O)$—, —NH—$CH(CH_3)_2$—$C(S)$—, —NH—$CH(CH_3)_2$—$C(NH)$—, —NH—$CH(CH_3)(CH_2CH_3)$—$C(O)$—, —NH—$CH(CH_3)(CH_2CH_3)$—$C(S)$—, —NH—$CH(CH_3)(CH_2CH_3)$—$C(NH)$—, —NH—$CH(phenyl)$-$C(O)$—, —NH—$CH(phenyl)$-$C(S)$—, and —NH—$CH(phenyl)$-$C(NH)$—, and pharmaceutically acceptable salts thereof.

A particularly preferred pentan-1-amine derivative that is a small molecule protease inhibitor is a compound of the following formula:

which is also known as indinavir. Indinavir and other pentan-1-amine derivatives, as well as methods for their synthesis, are described in U.S. Pat. No. 5,413,999 and European Patent Application No. EP 541 168.

With respect to hexan-2-ylcarbamate derivatives that are small molecule protease inhibitors, preferred hexane derivatives have the following structure:

(Formula VI)

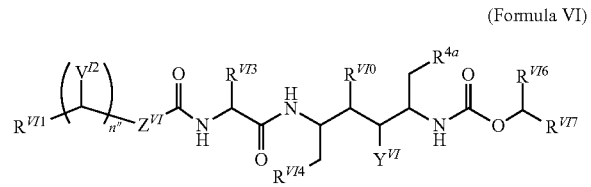

wherein:

$R^{VI1}$ is monosubstituted thiazolyl, monosubstituted oxazolyl, monosubstituted isoxazolyl or monosubstituted isothiazolyl wherein the substituent is selected from (i) lower alkyl, (ii) lower alkenyl, (iii) cycloalkyl, (iv) cycloalkylalkyl, (v) cycloalkenyl, (vi) cycloalkenylalkyl, (vii) heterocyclic wherein the heterocyclic is selected from aziridinyl, azetidinyl, pyrrolidinyl, piperidinyl, piperazinyl, morpholinyl, thiomorpholinyl, thiazolyl, oxazolyl, isoxazolyl, isothiazolyl, pyridinyl, pyrimidinyl, pyridazinyl and pyrazinyl and wherein the heterocyclic is unsubstituted or substituted with a substituent selected from halo, lower alkyl, hydroxy, alkoxy and thioalkoxy, (viii) (heterocyclic)alkyl wherein heterocyclic is defined as above, (ix) alkoxyalkyl, (x) thioalkoxyalkyl, (xi) alkylamino, (xii) dialkylamino, (xiii) phenyl wherein the phenyl ring is unsubstituted or substituted with a substituent selected from halo, lower alkyl, hydroxy, alkoxy and thioalkoxy, (xiv) phenylalkyl wherein the phenyl ring is unsubstituted or substituted as defined above, (xv) dialkylaminoalkyl, (xvi) alkoxy and (xvii) thioalkoxy;

n" is 1, 2 or 3;

$R^{VI2}$ is hydrogen or lower alkyl;

$R^{VI3}$ is lower alkyl;

$R^{VI4}$ and $R^{4a}$ are independently selected from phenyl, thiazolyl and oxazolyl wherein the phenyl, thiazolyl or oxazolyl ring is unsubstituted or substituted with a substituent selected from (i) halo, (ii) loweralkyl, (iii) hydroxy, (iv) alkoxy and (v) thioalkoxy;

$R^{VI6}$ is hydrogen or lower alkyl;

$R^{VI7}$ is thiazolyl, oxazolyl, isoxazolyl or isothiazolyl wherein the thiazolyl, oxazolyl, isoxazolyl or isothiazolyl ring is unsubstituted or substituted with lower alkyl;

$R^{VI0}$ is hydrogen and $Y^{VI}$ is —OH or $X^{VI}$ is —OH and $Y^{VI}$ is hydrogen, with the proviso that $X^{VI}$ is hydrogen and $Y^{VI}$ is —OH when $Z^{VI}$ is —N($R^{VI8}$)— and $R^{VI7}$ is unsubstituted and with the proviso that $X^{VI}$ is hydrogen and $Y^{VI}$ is —OH when $R^{VI3}$ is methyl and $R^{VI7}$ is unsubstituted; and $Z^{VI}$ is absent, —O—, —S—, —CH$^2$— or —N($R^{VI8}$)— wherein $R^{18}$ is lower alkyl, cycloalkyl, —OH or —NHR$^{8a}$ wherein $R^{8a}$ is hydrogen, lower alkyl or an amine-protecting group;

and pharmaceutically acceptable salts, esters or prodrug thereof.

A particularly preferred hexan-2-ylcarbamate derivative that is a small molecule protease inhibitor is a compound of the following formula:

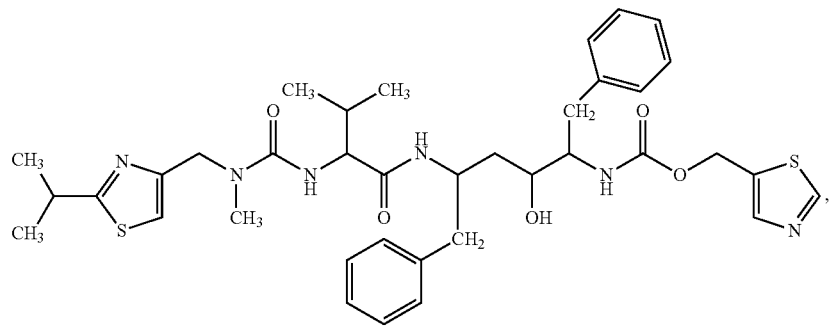 [SMILES: CC(C)c1nc(CN(C)C(=O)NC(C(=O)NC(Cc2ccccc2)CC(O)C(Cc2ccccc2)NC(=O)OCc2cncs2)C(C)C)cs1]

which is also known as ritonavir.

Another particularly preferred hexan-2-ylcarbamate derivative that is a small molecule protease inhibitor is a compound of the following formula:

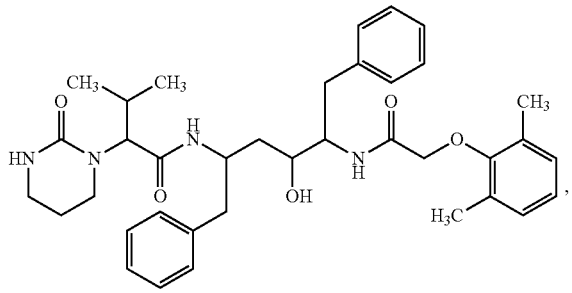 [SMILES: Cc1cccc(C)c1OCC(=O)NC(Cc1ccccc1)C(O)CC(Cc1ccccc1)NC(=O)C(C(C)C)N1CCCNC1=O]

which is also known as lopinavir. Ritonavir, lopinavir and other hexan-2-ylcarbamate derivatives, as well as methods for their synthesis, are described in U.S. Pat. No. 5,541,206 and WO 94/14436.

With respect to sulfonamide derivatives that are small molecule protease inhibitors, preferred sulfonamide derivatives have the following structure:

(Formula VII)

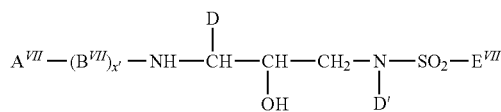

wherein:

$A^{VII}$ is selected from the group consisting of H, Het, —$R^{VII1}$-Het, —$R^{VII1}$—$C_{1-6}$ alkyl, which may be optionally substituted with one or more groups selected from the group consisting of hydroxy, $C_{1-4}$ alkoxy, Het, —O-Het, —$NR^{VII2}$—C(O)—N($R^{VII2}$)($R^{VII2}$) and —C(O)—N($R^{VII2}$)($R^{VII2}$); and —$R^{VII1}$—$C_{2-6}$ alkenyl, which may be optionally substituted with one or more groups selected from the group consisting of hydroxy, $C_{1-4}$ alkoxy, Het, —O-Het, —$NR^{VII2}$—C(O)N($R^{VII2}$)($R^{VII2}$) and —C(O)—N($R^{VII2}$)($R^{VII2}$);

each $R^{VII1}$ is independently selected from the group consisting of —C(O)—, —$SO_2$—, —C(O)C(O)—, —O—C(O)—, —$SO_2$, —$S(O)_2$—C(O)— and —$NR^{VII2}$C(O)— and —$NR^{VII2}$—C(O)—C(O)—;

each Het is independently selected from the group consisting of $C_{3-7}$ cycloalkyl;

$C_{5-7}$ cycloalkenyl; $C_{6-10}$ aryl; and 5-7 membered saturated or unsaturated heterocycle, containing one or more heteroatoms selected from N, N($R^{VII2}$), O, S and $S(O)_{n'''}$—, wherein said heterocycle may optionally be benzofused; and wherein any member of said Het may be optionally substituted with one or more substituents selected from the group consisting of oxo, —$OR^{VII2}$, —$R^{VII2}$, —N($R^{VII2}$), —$R^{VII2}$—OH, —CN, $CO_2R^{VII2}$, —C(O)N($R^{VII2}$)($R^{VII2}$), $SO_2$—N($R^{VII2}$)($R^{VII2}$)—N($R^{VII2}$)—C(O)—$R^{VII2}$, —C(O)—$R^{VII2}$, —$S(O)_{n'''}$—$R^{VII2}$, —$OCF_3$, —$S(O)_{n'''}$—Ar, methylenedioxy, —N($R^{VII2}$)—$SO_2$($R^{VII2}$), halo, —$CF_3$, —$NO_2$, Ar and —O—Ar;

each $R^{VII2}$ is independently selected from the group consisting of H and $C_{1-3}$ alkyl optionally substituted with Ar;

$B^{VII2}$ when present, is —N($R^{VII2}$)—C($R^{VII3}$)($R^{VII3}$)—C(O)—;

x' is 0 or 1;

each $R^{VII3}$ is independently selected from the group consisting of H, Het, $C_{1-6}$ alkyl, $C_{2-6}$ alkenyl, $C_{3-6}$ cycloalkyl and $C_{5-6}$ cycloalkenyl, wherein any member of said $R^{VII3}$, except H, may be optionally substituted with one or more substituents selected from the group consisting of —$OR^{VII2}$, —C(O)—NH—$R^{VII2}$, —$S(O)_{n'''}$—N($R^{VII2}$)($R^{VII2}$), Het, —CN, —$SR^{VII2}$, —$CO_2R^{VII2}$, $NR^{VII2}$—C(O)—$R^{VII2}$;

each n''' is independently 1 or 2;

D and D' are independently selected from the group consisting of Ar; $C_{1-4}$ alkyl, which may be optionally substituted with one or more groups selected from $C_{3-6}$ cycloalkyl, —$OR^{VII2}$, —$R^{VII3}$, —O—Ar and Ar; $C_{2-4}$ alkenyl, which may be optionally substituted with one or more groups selected from the group consisting of $C_{3-6}$ cycloalkyl, —$OR^{VII2}$, —$R^{VII3}$, —O—Ar and Ar; $C_{3-6}$ cycloalkyl, which may be optionally substituted with or fused with Ar; and $C_{5-6}$ cycloalkenyl, which may be optionally substituted with or fused with Ar;

each Ar is independently selected from the group consisting of phenyl; 3-6 membered carbocyclic ring and 5-6 membered heterocyclic ring containing one or more heteroatoms selected from O, N, S, $S(O)_{n'''}$ and N($R^{VII2}$), wherein said carbocyclic or heterocyclic ring may be saturated or unsaturated and optionally substituted with one or more groups selected from the group consisting of oxo, —$OR^{VII2}$, —$R^{VII2}$, —N($R^{VII2}$)($R^{VII2}$), —N($R^{VII2}$)—C(O)$R^{VII2}$, —$R^{VII2}$—OH, —CN, —$CO_2R^{VII2}$, —C(O)—N($R^{VII2}$)($R^{VII2}$), halo and —$CF_3$;

E is selected from the group consisting of Het; O-Het; Het-Het; —O—$R^{VII3}$; —$NR^{VII2}R^{VII3}$; $C_{1-6}$ alkyl, which may be optionally substituted with one or more groups selected from the group consisting of $R^{VII4}$ and Het; $C_{2-6}$ alkenyl, which may be optionally substituted with one or more groups selected from the group consisting of $R^{VII4}$ and Het; $C_{3-6}$ saturated carbocycle, which may optionally be substituted with one or more groups selected from the group consisting of $R^{VII4}$ and Het; and $C_{5-6}$ unsaturated carbocycle, which may optionally be substituted with one or more groups selected from the group consisting of $R^{VII4}$ and Het; and each $R^{VII4}$ is independently selected from the group consisting of —$OR^{VII2}$, —C(O)—$NHR^{VII2}$, $SO_2$—$NHR^{VII2}$, halo, —$NR^{VII2}$—C(O)—$R^{VII3}$ and —CN, and pharmaceutically acceptable salts, esters or prodrug thereof.

A particularly preferred sulfonamide derivative that is a small molecule protease inhibitor is a compound of the following formula:

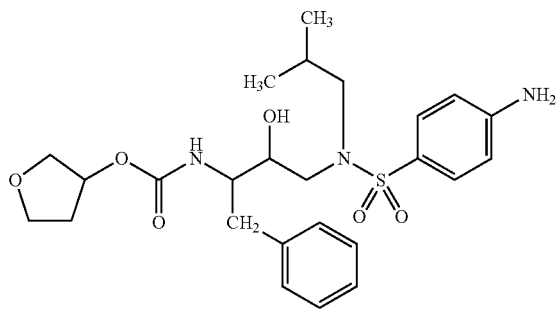 [SMILES: CC(C)CN(CC(O)C(Cc1ccccc1)NC(=O)OC1CCOC1)S(=O)(=O)c1ccc(N)cc1]

which is also known as amprenavir. Another particularly preferred sulfonamide derivative that is a small molecule protease inhibitor is a compound of the following formula:

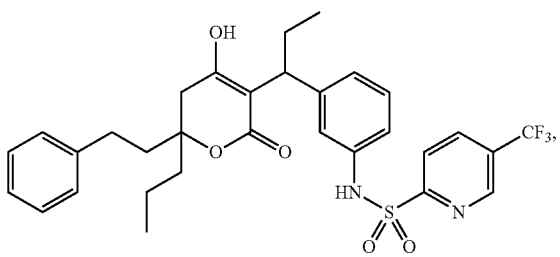

U-140690.

Amprenavir, U-140690 and other sulfonamide derivatives, as well as methods for their synthesis, are described in U.S. Pat. Nos. 5,732,490 and 5,585,397, WO 93/23368, and WO 95/30670.

A particularly preferred prodrug form of a sulfonamide derivative is the phosphonooxy-based prodrug of the following formula:

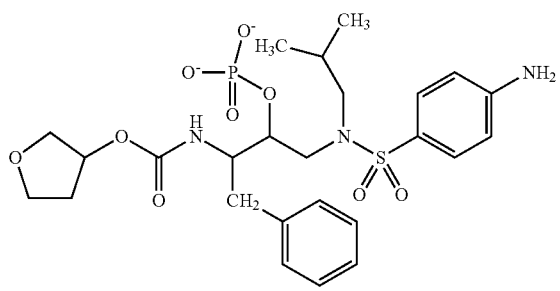 [SMILES: CC(C)CN(CC(OP(=O)([O-])[O-])C(Cc1ccccc1)NC(=O)OC1CCOC1)S(=O)(=O)c1ccc(N)cc1]

which is known as fosamprenavir and pharmaceutically acceptable salts thereof. Fosamprenavir and other sulfonamide derivatives, as well as methods for their synthesis, are described in U.S. Pat. Nos. 6,514,953 and 6,436,989.

With respect to tri-substituted phenyl derivatives that are small molecule protease inhibitors, preferred tri-substituted phenyl derivatives have the following structure:

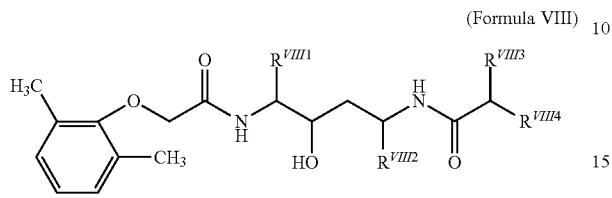

(Formula VIII)

wherein:
$R^{VIII1}$ is benzyl;
$R^{VIII2}$ is benzyl or lower alkyl;
$R^{VIII3}$ is lower alkyl; and
$R^{VIII5}$ is

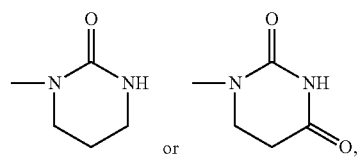

and pharmaceutically acceptable salts thereof. These and other small molecule protease inhibitors, as well as methods for their synthesis, are described in WO 97/21685.

As previously indicated, the small molecule protease inhibitor may not necessarily be categorized within one of the aforementioned classes. Such small molecule protease inhibitors, however, can still be conjugated to a water-soluble, non-peptidic oligomer as described herein. Nonlimiting additional small molecule protease inhibitors include the compounds:

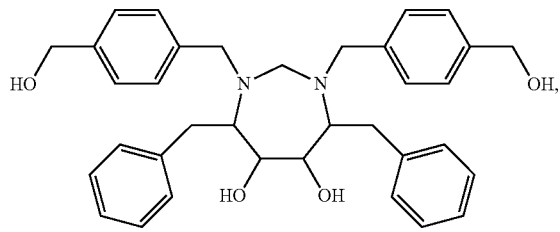

DMP-323;

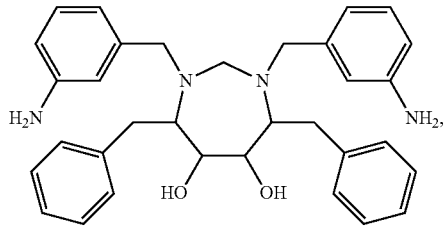

DMP-450;

and
related compounds, disclosed in WO 93/07128.

Still other small molecule protease inhibitors include:

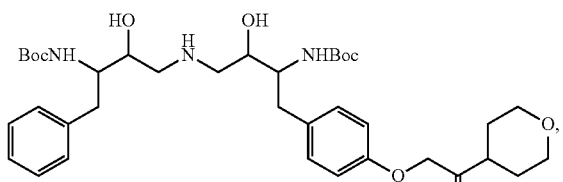

BMS 186,613;

and other others described in European Patent Application No. EP 580 402.

Still other small molecule protease inhibitors include:

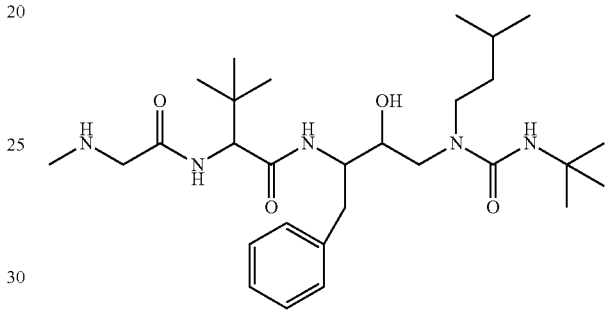

SC-55389a and other others described in WO 95/06061.

Still other small molecule protease inhibitors include:

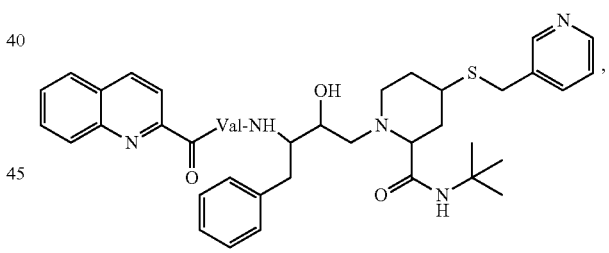

BILA 1096 BS;

and others described in EP 560268.

In some embodiments, it is preferred that the small molecule protease inhibitor is selected from the group selected from the group consisting of amprenavir, atazanavir, fosamprenavir, indinavir, lopinavir, saquinavir, nelfinavir, ritonavir, tipranovir and darunavir.

Each of these (and other) protease inhibitor can be covalently attached (either directly or through one or more atoms) to a water-soluble, non-peptidic oligomer.

Small molecule drugs useful in the invention generally have a molecular weight of less than 1000 Da. Exemplary molecular weights of small molecule drugs include molecular weights of: less than about 950; less than about 900; less than about 850; less than about 800; less than about 750; less than about 700; less than about 650; less than about 600; less than about 550; less than about 500; less than about 450; less than about 400; less than about 350; and less than about 300.

The small molecule drug used in the invention, if chiral, may be in a racemic mixture, or an optically active form, for example, a single optically active enantiomer, or any combination or ratio of enantiomers (i.e., scalemic mixture). In addition, the small molecule drug may possess one or more geometric isomers. With respect to geometric isomers, a composition can comprise a single geometric isomer or a mixture of two or more geometric isomers. A small molecule drug for use in the present invention can be in its customary active form, or may possess some degree of modification. For example, a small molecule drug may have a targeting agent, tag, or transporter attached thereto, prior to or after covalent attachment of an oligomer. Alternatively, the small molecule drug may possess a lipophilic moiety attached thereto, such as a phospholipid (e.g., distearoylphosphatidylethanolamine or "DSPE," dipalmitoylphosphatidylethanolamine or "DPPE," and so forth) or a small fatty acid. In some instances, however, it is preferred that the small molecule drug moiety does not include attachment to a lipophilic moiety.

The small molecule protease inhibitor for coupling to a water-soluble, non-peptidic oligomer possesses a free reactive group, such as a hydroxyl, amide, carboxyl, thio, amino group, or the like (i.e., "handle") suitable for covalent attachment to the oligomer. In addition, the small molecule protease inhibitor can be modified by introduction of a reactive group, preferably by conversion of one of its existing functional groups to a reactive group suitable for formation of a stable covalent linkage between the oligomer and the drug. Both approaches are illustrated in the Experimental section.

The water-soluble, non-peptidic oligomer typically comprises one or more monomers serially attached to form a chain of monomers. The oligomer can be formed from a single monomer type (i.e., is homo-oligomeric) or two or three monomer types (i.e., is co-oligomeric). Preferably, each oligomer is a co-oligomer of two monomers or, more preferably, is a homo-oligomer.

Accordingly, each oligomer is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; α-hydroxy acid, such as lactic acid or glycolic acid; phosphazene, oxazoline, amino acids, carbohydrates such as monosaccharides, saccharide or mannitol; and N-acryloylmorpholine. Preferred monomer types include alkylene oxide, olefinic alcohol, hydroxyalkyl methacrylamide or methacrylate, N-acryloylmorpholine, and α-hydroxy acid. Preferably, each oligomer is, independently, a co-oligomer of two monomer types selected from this group, or, more preferably, is a homo-oligomer of one monomer type selected from this group.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a small molecule is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

The water-soluble, non-peptidic oligomer (e.g., "POLY" in the conjugate formula

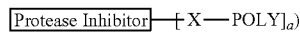

can have any of a number of different geometries. For example, the water-soluble, non-peptidic oligomer can be linear, branched, or forked. Most typically, the water-soluble, non-peptidic oligomer is linear or is branched, for example, having one branch point. Although much of the discussion herein is focused upon poly(ethylene oxide) as an illustrative oligomer, the discussion and structures presented herein can be readily extended to encompass any of the water-soluble, non-peptidic oligomers described above.

The molecular weight of the water-soluble, non-peptidic oligomer, excluding the linker portion, is generally relatively low. Exemplary values of the molecular weight of the water-soluble polymer include: below about 1500 Daltons; below about 1450 Daltons; below about 1400 Daltons; below about 1350 Daltons; below about 1300 Daltons; below about 1250 Daltons; below about 1200 Daltons; below about 1150 Daltons; below about 1100 Daltons; below about 1050 Daltons; below about 1000 Daltons; below about 950 Daltons; below about 900 Daltons; below about 850 Daltons; below about 800 Daltons; below about 750 Daltons; below about 700 Daltons; below about 650 Daltons; below about 600 Daltons; below about 550 Daltons; below about 500 Daltons; below about 450 Daltons; below about 400 Daltons; below about 350 Daltons; below about 300 Daltons; below about 250 Daltons; below about 200 Daltons; below about 150 Daltons; and below about 100 Daltons.

Exemplary ranges of molecular weights of the water-soluble, non-peptidic oligomer (excluding the linker) include: from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

Preferably, the number of monomers in the water-soluble, non-peptidic oligomer falls within one or more of the following ranges (end points for each range provided are inclusive): between about 1 and about 30; between about 1 and about 25; between about 1 and about 20; between about 1 and about 15; between about 1 and about 12; between about 1 and about 10. In certain instances, the number of monomers in series in the oligomer (and the corresponding conjugate) is one of 1, 2, 3, 4, 5, 6, 7, or 8. In additional embodiments, the oligomer (and the corresponding conjugate) contains 9, 10, 11, 12, 13, 14, 15, 16, 17, 18, 19, or monomers in series. In yet further embodiments, the oligomer (and the corresponding conjugate) possesses 21, 22, 23, 24, 25, 26, 27, 28, 29 or 30 monomers in series. Thus, for example, when the water-soluble, non-peptidic polymer includes $CH_3$—$(OCH_2CH_2)_n$—, "n" is an integer that can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and can fall within one or more of the following ranges: between about 1 and about 25; between about 1 and about 20; between about 1 and about 15; between about 1 and about 12; between about 1 and about 10.

When the water-soluble, non-peptidic oligomer has 1, 2, 3, 4, 5, 6, 7, 8, 9, or 10 monomers, these values correspond to a methoxy end-capped oligo(ethylene oxide) having a molecular weights of about 75, 119, 163, 207, 251, 295, 339, 383, 427, and 471 Daltons, respectively. When the oligomer has 11, 12, 13, 14, or 15 monomers, these values correspond to methoxy end-capped oligo(ethylene oxide) having molecular weights corresponding to about 515, 559, 603, 647, and 691 Daltons, respectively.

When the water-soluble, non-peptidic oligomer is attached to the small molecule protease inhibitor (in contrast to the step-wise addition of one or more monomers to effectively "grow" the oligomer onto the small molecule protease inhibitor), it is preferred that the composition containing an activated form of the water-soluble, non-peptidic oligomer be monodispersed. In those instances, however, where a bimodal composition is employed, the composition will possess a bimodal distribution centering around any two of the above numbers of monomers. Ideally, the polydispersity index of each peak in the bimodal distribution, Mw/Mn, is 1.01 or less, and even more preferably, is 1.001 or less, and even more preferably is 1.0005 or less. Most preferably, each peak possesses a MW/Mn value of 1.0000. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble, non-peptidic oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

It is preferred that the water-soluble, non-peptidic oligomer is obtained from a composition that is preferably unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials such as Sigma-Aldrich. Water-soluble, non-peptidic oligomers can be prepared as described in Chen Y., Baker, G. L., J. Org. Chem., 6870-6873 (1999), WO 02/098949, and U.S. Patent Application Publication 2005/0136031.

The linker or linkage (through which the water-soluble, non-peptidic polymer is attached to the small molecule protease inhibitor) at least includes a covalent bond, and often includes one or more atoms such as an oxygen, two atoms, or a number of atoms. A linker is typically but is not necessarily linear in nature. The linkage, "X" (in $$\boxed{\text{Protease Inhibitor}}-[X-POLY]_a),$$

is a stable linkage, and is preferably also enzymatically stable. Preferably, the linkage "X" is one having a chain length of less than about 12 atoms, and preferably less than about 10 atoms, and even more preferably less than about 8 atoms and even more preferably less than about 5 atoms, whereby length is meant the number of atoms in a single chain, not counting substituents. For instance, a urea linkage such as this, $R_{oligomer}$—NH—(C=O)—NH—$R'_{drug}$, is considered to have a chain length of 3 atoms (—NH—C(O)—NH—). In selected embodiments, the linkage does not comprise further spacer groups.

In some instances, the linker "X" comprises an ether, amide, urethane, amine, thioether, urea, or a carbon-carbon bond. Functional groups such as those discussed below, and illustrated in the examples, are typically used for forming the linkages. The linkage may less preferably also comprise (or be adjacent to or flanked by) spacer groups. Spacers are most useful in instances where the bioactivity of the conjugate is significantly reduced due to the positioning of the oligomer relatively close to the residue of the small molecule drug, wherein a spacer can serve to increase the distance between oligomer and the residue of the small molecule drug.

More specifically, in selected embodiments, a spacer moiety, X, may be any of the following: "—" (i.e., a covalent bond, that may be stable or degradable, between the residue of the small molecule protease inhibitor and the water-soluble, non-peptidic oligomer), —O—, —NH—, —S—, —C(O)—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—

CH$_2$—NH—C(O)—CH$_2$—, bivalent cycloalkyl group, —N(R$^6$)—, R$^6$ is H or an organic radical selected from the group consisting of alkyl, substituted alkyl, alkenyl, substituted alkenyl, alkynyl, substituted alkynyl, aryl and substituted aryl.

For purposes of the present invention, however, a group of atoms is not considered a spacer moiety when it is immediately adjacent to an oligomer segment, and the group of atoms is the same as a monomer of the oligomer such that the group would represent a mere extension of the oligomer chain.

The linkage "X" between the water-soluble, non-peptidic oligomer and the small molecule is typically formed by reaction of a functional group on a terminus of the oligomer (or one or more monomers when it is desired to "grow" the oligomer onto the protease inhibitor) with a corresponding functional group within the protease inhibitor. Illustrative reactions are described briefly below. For example, an amino group on an oligomer may be reacted with a carboxylic acid or an activated carboxylic acid derivative on the small molecule, or vice versa, to produce an amide linkage. Alternatively, reaction of an amine on an oligomer with an activated carbonate (e.g. succinimidyl or benzotriazyl carbonate) on the drug, or vice versa, forms a carbamate linkage. Reaction of an amine on an oligomer with an isocyanate (R—N=C=O) on a drug, or vice versa, forms a urea linkage (R—NH—(C=O)—NH—R'). Further, reaction of an alcohol (alkoxide) group on an oligomer with an alkyl halide, or halide group within a drug, or vice versa, forms an ether linkage. In yet another coupling approach, a small molecule having an aldehyde function is coupled to an oligomer amino group by reductive amination, resulting in formation of a secondary amine linkage between the oligomer and the small molecule.

A particularly preferred water-soluble, non-peptidic oligomer is an oligomer bearing an aldehyde functional group. In this regard, the oligomer will have the following structure: CH$_3$O—(CH$_2$—CH$_2$—O)$_n$—(CH$_2$)$_p$—C(O)H, wherein (n) is one of 1, 2, 3, 4, 5, 6, 7, 8, 9 and 10 and (p) is one of 1, 2, 3, 4, 5, 6 and 7. Preferred (n) values include 3, 5 and 7 and preferred (p) values 2, 3 and 4. In addition, the carbon atom alpha to the —C(O)H moiety can optionally be substituted with alkyl.

Typically, the terminus of the water-soluble, non-peptidic oligomer not bearing a functional group is capped to render it unreactive. When the oligomer does include a further functional group at a terminus other than that intended for formation of a conjugate, that group is either selected such that it is unreactive under the conditions of formation of the linkage "X," or it is protected during the formation of the linkage "X."

As stated above, the water-soluble, non-peptidic oligomer includes at least one functional group prior to conjugation. The functional group typically comprises an electrophilic or nucleophilic group for covalent attachment to a small molecule, depending upon the reactive group contained within or introduced into the small molecule. Examples of nucleophilic groups that may be present in either the oligomer or the small molecule include hydroxyl, amine, hydrazine (—NHNH$_2$), hydrazide (—C(O)NHNH$_2$), and thiol. Preferred nucleophiles include amine, hydrazine, hydrazide, and thiol, particularly amine. Most small molecule drugs for covalent attachment to an oligomer will possess a free hydroxyl, amino, thio, aldehyde, ketone, or carboxyl group.

Examples of electrophilic functional groups that may be present in either the oligomer or the small molecule include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, is 2-thiazolidine thione, etc., as well as hydrates or protected derivatives of any of the above moieties (e.g. aldehyde hydrate, hemiacetal, acetal, ketone hydrate, hemiketal, ketal, thioketal, thioacetal).

An "activated derivative" of a carboxylic acid refers to a carboxylic acid derivative which reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form —(CO)O—N[(CO)—]$_2$; for example, N-hydroxysuccinimidyl (NHS) esters or N-hydroxyphthalimidyl esters. Also preferred are imidazolyl esters and benzotriazole esters. Particularly preferred are activated propionic acid or butanoic acid esters, as described in co-owned U.S. Pat. No. 5,672,662. These include groups of the form —(CH$_2$)$_{2-3}$C(=O)O-Q, where Q is preferably selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g. hydroxy, thio, or amino groups, to produce various bond types. Preferred for the present invention are reactions which favor formation of a hydrolytically stable linkage. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the most hydrolytically stable. Carbonates, including succinimidyl, imidazolyl, and benzotriazole carbonates, react with amino groups to form carbamates. Isocyanates (R—N=C=O) react with hydroxyl or amino groups to form, respectively, carbamate (RNH—C(O)—OR') or urea (RNH—C(O)—NHR') linkages. Aldehydes, ketones, glyoxals, diones and their hydrates or alcohol adducts (i.e. aldehyde hydrate, hemiacetal, acetal, ketone hydrate, hemiketal, and ketal) are preferably reacted with amines, followed by reduction of the resulting imine, if desired, to provide an amine linkage (reductive amination).

Several of the electrophilic functional groups include electrophilic double bonds to which nucleophilic groups, such as thiols, can be added, to form, for example, thioether bonds. These groups include maleimides, vinyl sulfones, vinyl pyridine, acrylates, methacrylates, and acrylamides. Other groups comprise leaving groups that can be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Reactions involving complementary reactive groups such as those noted above on the oligomer and the small molecule are utilized to prepare the conjugates of the invention.

In some instances the protease inhibitor may not have a functional group suited for conjugation. In this instance, it is possible to modify the "original" protease inhibitor so that it does have the desired functional group. For example, if the protease inhibitor has an amide group, but an amine group is desired, it is possible to modify the amide group to an amine group by way of a Hofmann rearrangement, Curtius rearrangement (once the amide is converted to an azide) or Lossen rearrangement (once amide is concerted to hydroxamide followed by treatment with tolyene-2-sulfonyl chloride/base).

It is possible to prepare a conjugate of small molecule protease inhibitor bearing a carboxyl group wherein the carboxyl group-bearing small molecule protease inhibitor is coupled to an amino-terminated oligomeric ethylene glycol, to provide a conjugate having an amide group covalently linking the small molecule protease inhibitor agonist to the oligomer. This can be performed, for example, by combining the carboxyl group-bearing small molecule protease inhibitor with the amino-terminated oligomeric ethylene glycol in the presence of a coupling reagent, (such as dicyclohexylcarbodiimide or "DCC") in an anhydrous organic solvent.

Further, it is possible to prepare a conjugate of a small molecule protease inhibitor bearing a hydroxyl group wherein the hydroxyl group-bearing small molecule protease inhibitor is coupled to an oligomeric ethylene glycol halide to result in an ether (—O—) linked small molecule conjugate. This can be performed, for example, by using sodium hydride to deprotonate the hydroxyl group followed by reaction with a halide-terminated oligomeric ethylene glycol.

In another example, it is possible to prepare a conjugate of a small molecule protease inhibitor bearing a ketone group by first reducing the ketone group to form the corresponding hydroxyl group. Thereafter, the small molecule protease inhibitor now bearing a hydroxyl group can be coupled as described herein.

In still another instance, it is possible to prepare a conjugate of a small molecule protease inhibitor bearing an amine group. In one approach, the amine group-bearing small molecule protease inhibitor and an aldehyde-bearing oligomer are dissolved in a suitable buffer after which a suitable reducing agent (e.g., NaCNBH$_3$) is added. Following reduction, the result is an amine linkage formed between the amine group of the amine group-containing small molecule protease inhibitor and the carbonyl carbon of the aldehyde-bearing oligomer.

In another approach for preparing a conjugate of a small molecule protease inhibitor bearing an amine group, a carboxylic acid-bearing oligomer and the amine group-bearing small molecule protease inhibitor are combined, typically in the presence of a coupling reagent (e.g., DCC). The result is an amide linkage formed between the amine group of the amine group-containing small molecule protease inhibitor and the carbonyl of the carboxylic acid-bearing oligomer.

Exemplary conjugates of the small molecule protease inhibitors of Formula I include those having the following structures:

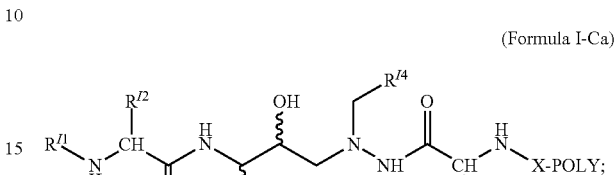
(Formula I-Ca)

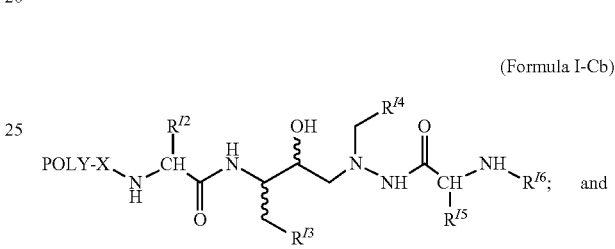
(Formula I-Cb)

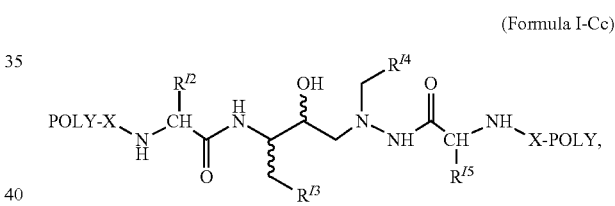
(Formula I-Cc)

wherein for each of Formula I-Ca, Formula I-Cb and Formula I-Cc: X is a stable linkage; POLY is a water-soluble, non-peptidic oligomer; and each of $R^{I1}$, $R^{I2}$, $R^{I3}$, $R^{I4}$, $R^{I5}$ and $R^{I6}$ is as defined with respect to Formula I.

Preferred conjugates of small molecule protease inhibitors include those having the following structures:

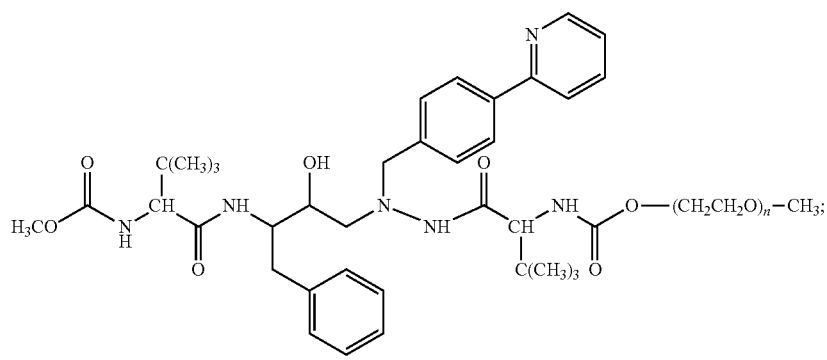

-continued

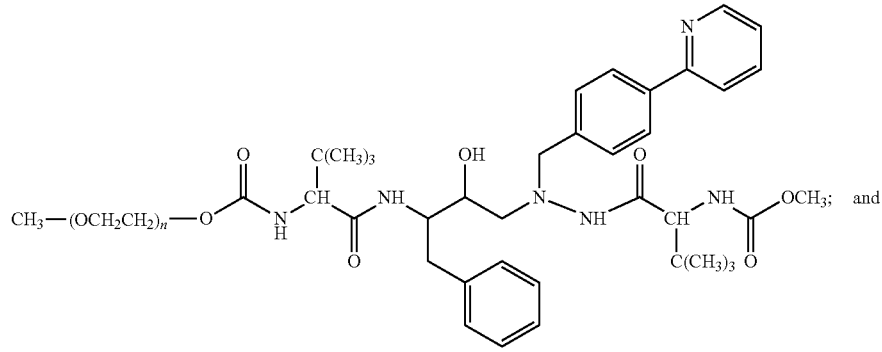

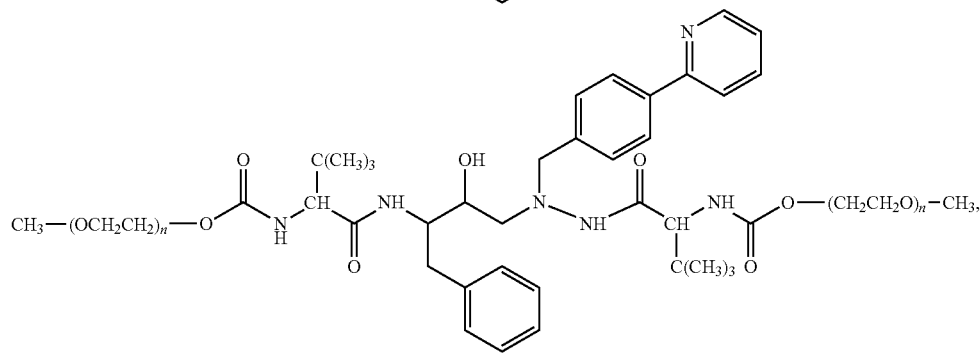

wherein, in each instance where it appears, n is an integer from 2 to 30.

Exemplary conjugates of small molecule protease inhibitors of Formula II include those having the following structures:

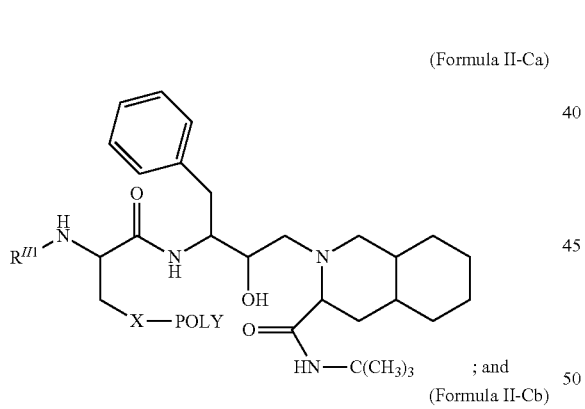

(Formula II-Ca)

; and (Formula II-Cb)

wherein, in each instance in which it appears: X is a stable linkage; POLY is a water-soluble, non-peptidic oligomer; and $R^{III}$ is benzyloxycarbonyl or 2-quinolylcarbonyl.

Preferred conjugates of small molecule protease inhibitors include those having the following structures:

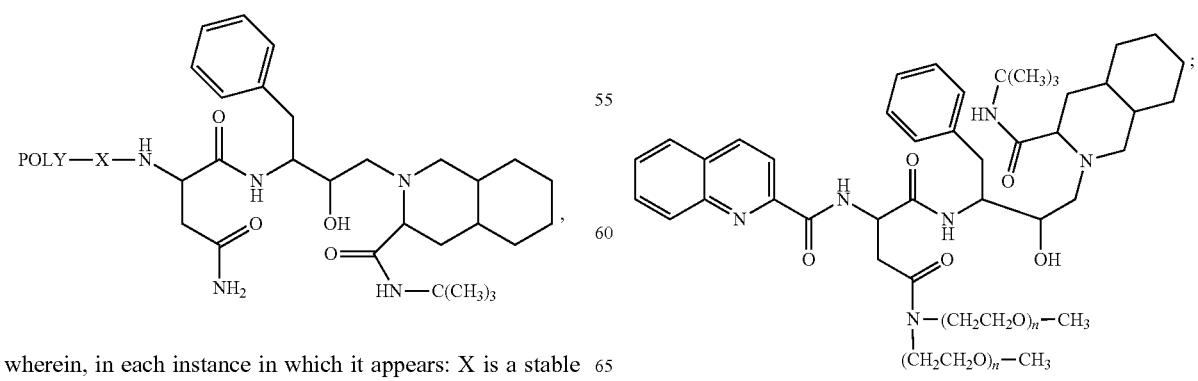

-continued

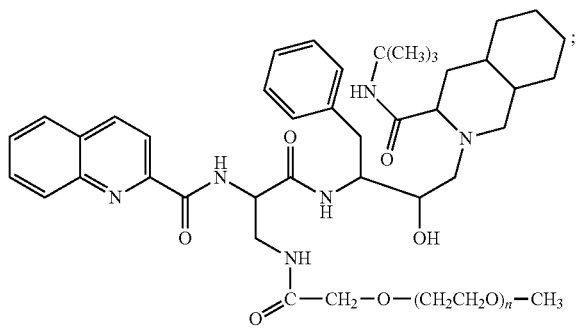

Exemplary conjugates of the small molecule protease inhibitors of Formula III include those having the following structures:

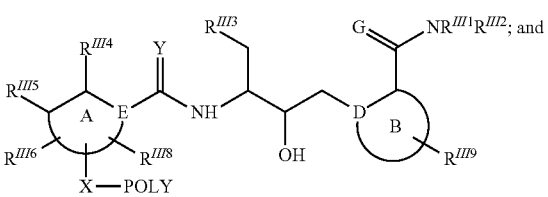

(Formula III-Ca)

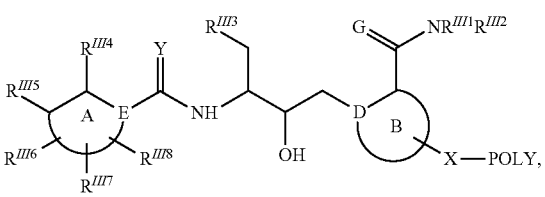

(Formula III-Cb)

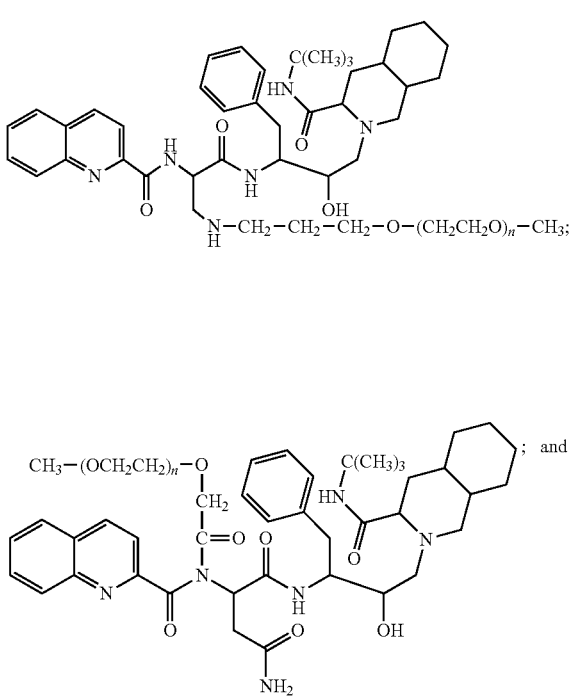

wherein, in each instance in where it appears: X is a stable linkage; POLY is a water-soluble, non-peptidic oligomer; and each of $R^{III1}$, $R^{III2}$, $R^{III3}$, $R^{III4}$, $R^{III5}$, $R^{III6}$, $R^{III7}$, $R^{III8}$, Y, G, D, E, $R^{III9}$, A and B is as defined with respect to Formula III.

Preferred conjugates of small molecule protease inhibitors include those having the following structure:

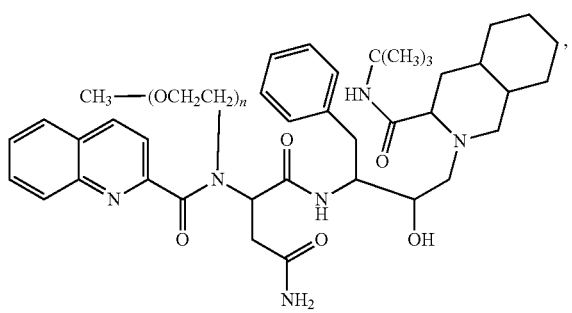

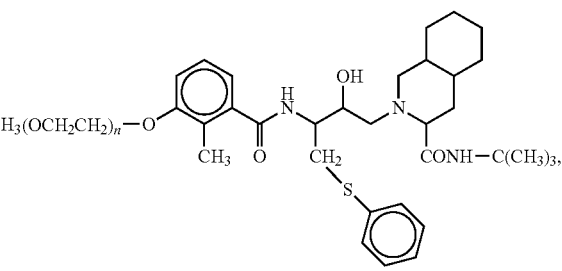

wherein, in each instance where it appears, n is an integer from 2 to 30.

wherein, in each instance where it appears, n is an integer from 2 to 30.

Exemplary conjugates of the small molecule protease inhibitors of Formula IV include those having the following structure:

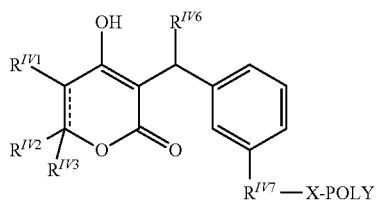

(Formula IV-C)

wherein: X is a stable linkage; POLY is a water-soluble, non-peptidic oligomer; and $R^{IV1}$, $R^{IV2}$, $R^{IV3}$, $R^{IV6}$ and $R^{IV7}$ is as defined with respect to Formula IV.

Preferred conjugates of small molecule protease inhibitors include those having the following structure:

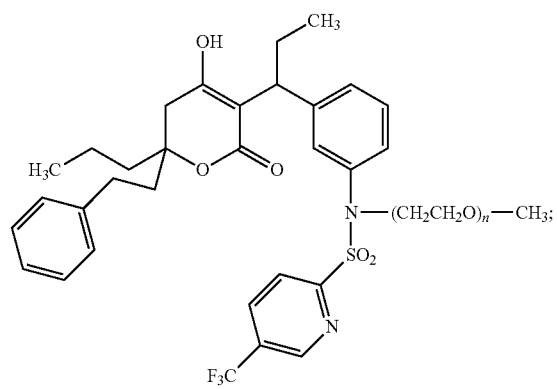

wherein, in each instance where it appears, n is an integer from 2 to 30.

Exemplary conjugates of the small molecule protease inhibitors of Formula V include those having the following structure:

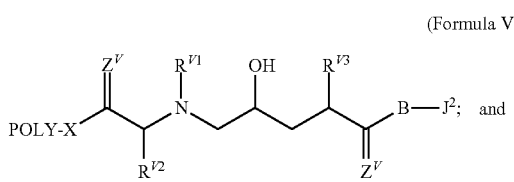

(Formula V-Ca)

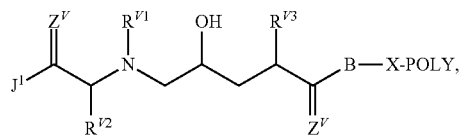

(Formula V-Cb)

wherein, in each instance where it appears: X is a stable linkage; POLY is a water-soluble, non-peptidic oligomer; and each of $Z^V$, $R^{V1}$, $R^{V2}$, $R^{V3}$, $J^1$, $J^2$ and B is as defined with respect to Formula V.

Preferred conjugates of small molecule protease inhibitors include those having the following structure:

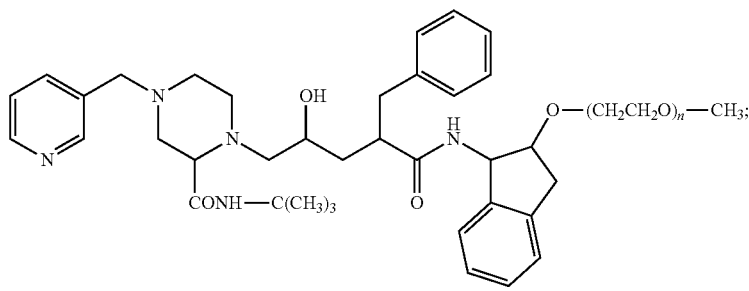

wherein, in each instance where it appears, n is an integer from 2 to 30.

Exemplary conjugates of the small molecule protease inhibitors of Formula VI include those having the following structure:

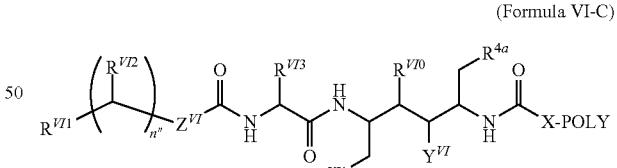

(Formula VI-C)

wherein: X is a stable linkage; POLY is a water-soluble, non-peptidic oligomer; $R^{VI0}$ is H; and each of $R^{VI1}$, n″, $R^{VI2}$, $R^{VI3}$, $R^{VI4}$, $R^{4a}$ and $Z^{VI}$ is as defined with respect to Formula VI.

Preferred conjugates of small molecule protease inhibitors include those having the following structures:

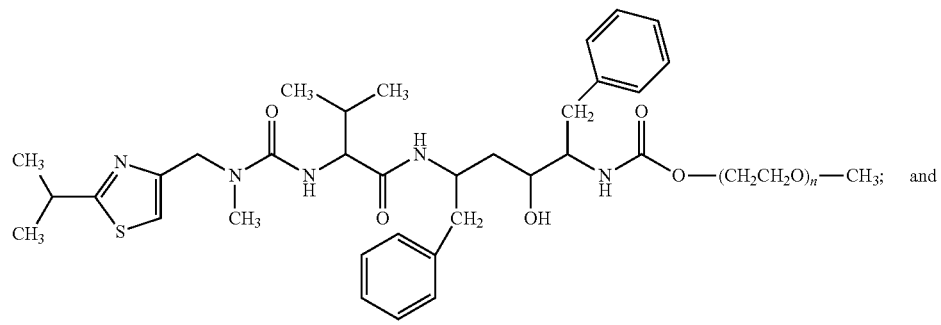

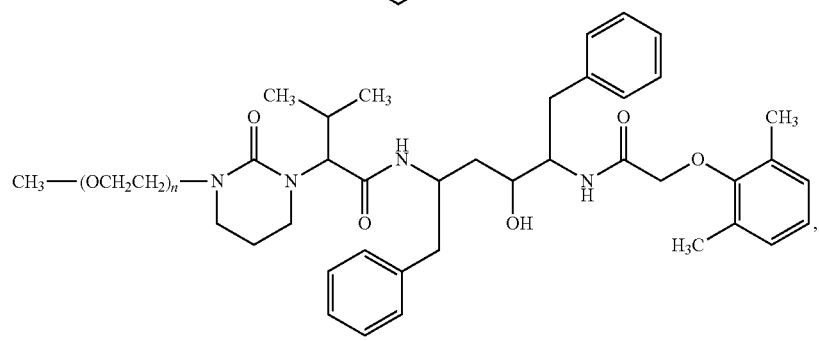

wherein, in each instance where it appears, n is an integer from 2 to 30.

Exemplary conjugates of the small molecule protease inhibitors of Formula VII include those having the following structure:

(Formula VII-C)

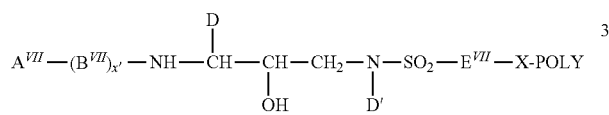

wherein: X is a stable linkage; POLY is a water-soluble, non-peptidic oligomer; and each of $A^{VII}$, $B^{VII}$, x', D, D' and $E^{VII}$ is as defined with respect to Formula VII.

Preferred conjugates of small molecule protease inhibitors include those having the following structures:

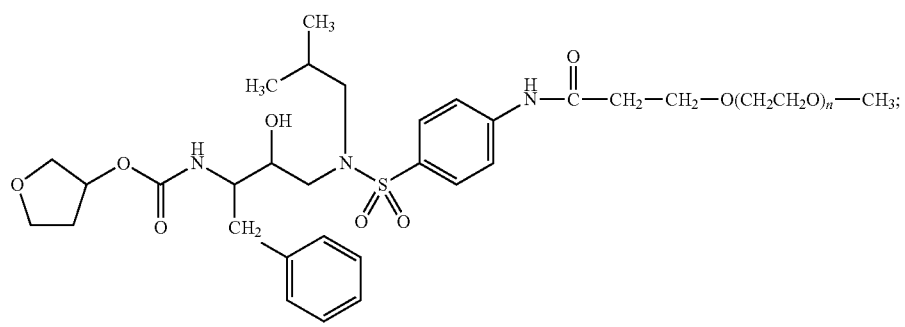

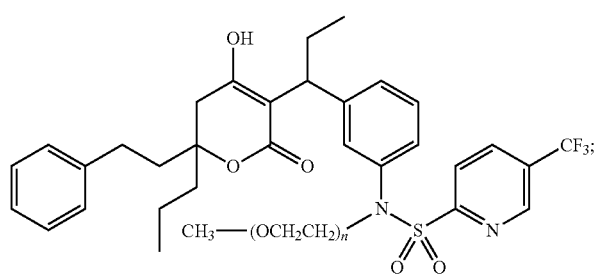

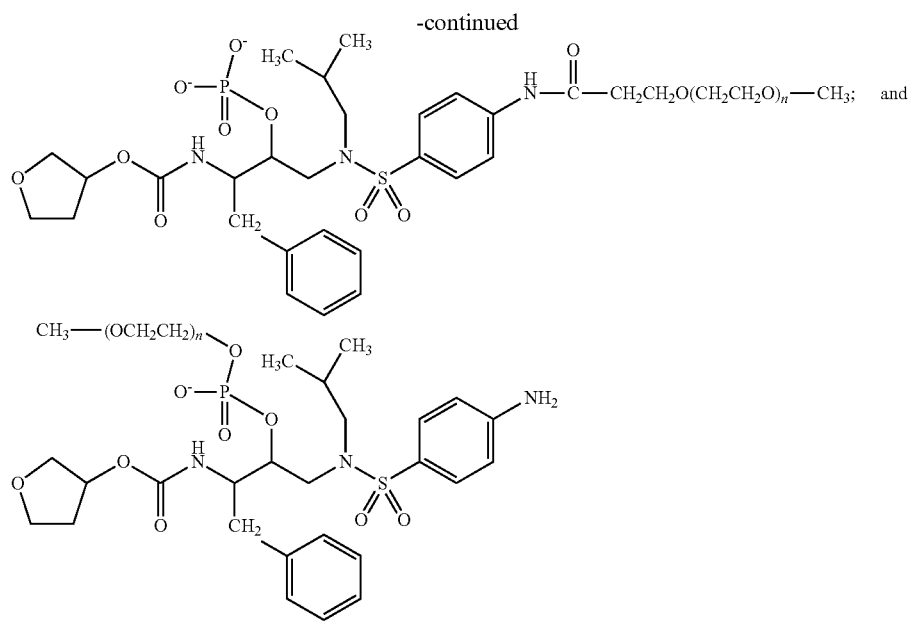

wherein, in each instance where it appears, n is an integer from 2 to 30.

Exemplary conjugates of the small molecule protease inhibitors of Formula VIII include those having the following structures:

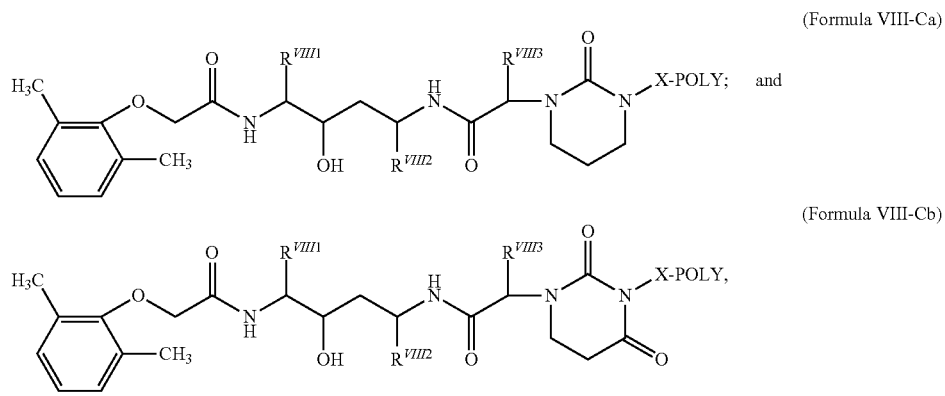

(Formula VIII-Ca)

(Formula VIII-Cb)

wherein: X is a stable linkage; POLY is a water-soluble, non-peptidic oligomer; and each of $R^{VIII1}$, $R^{VIII2}$ and $R^{VIII3}$ is as defined with respect to Formula VIII.

Still further exemplary conjugates include those having the following structures (wherein, with respect to each structure, X is a stable linkage and POLY is a water-soluble, non-peptidic oligomer):

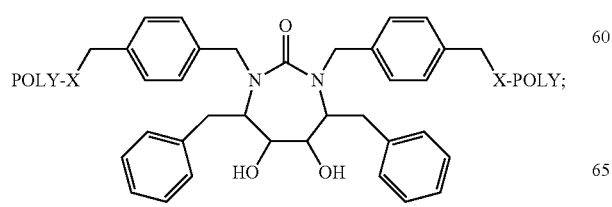

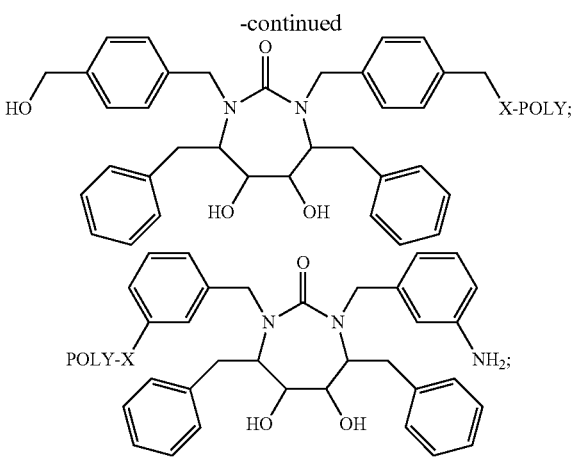

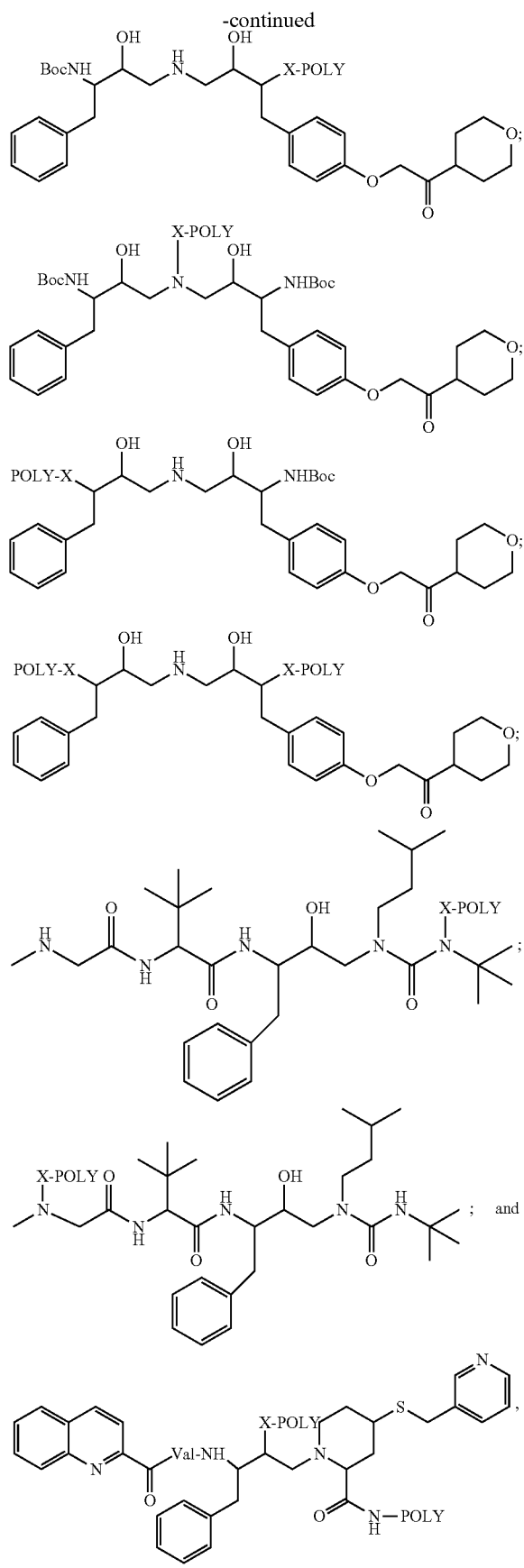

wherein, in each instance in which it appears, X is a stable linkage, POLY is a water-soluble, non-peptidic oligomer, and Val is a residue of valine.

One of ordinary skill in the art, using routine experimentation, can determine a best suited molecular size and linkage for reducing metabolism by first preparing a series of oligomers with different weights and functional groups and then obtaining the necessary clearance profiles by administering the conjugates to a patient and taking periodic blood and/or urine sampling and testing for the presence and amount of metabolites. Once a series of metabolism profiles have been obtained for each tested conjugate, a suitable conjugate can be identified.

To determine whether the small molecule protease inhibitor or the conjugate of a small molecule protease inhibitor and a water-soluble non-peptidic polymer has anti-HIV activity, it is possible to test such compounds. Anti-HIV activity can be tested as described in the Experimental. In addition, Anti-HIV activity can be tested in a human T-cell line by, for example, the method disclosed in Kempf et al. (1991) *Antimicrob. Agents Chemother.* 35(11):2209-2214, HIV-$1_{3B}$ stock ($10^{4.7}$ 50% tissue culture infection doses per ml) can be diluted 100-fold and incubated with MT-4 cells at $4 \times 10^5$ cells per ml for one hour at 37° C. (multiplicity of infection, 0.001 50% tissue culture infective dose per cell). The resulting culture is then washed twice, resuspended to $10^5$ cells per ml of medium, seeded in a volume of 1% dimethyl sulfoxide solution of compound in a series of half-log-unit dilutions in medium in triplicate. The virus control culture can be treated in an identical manner, except that no compound is added to the medium. The cell control is incubated in the absence of compound or virus. Optical density (OD) is then measured at day 5 by using 3-(4,5-dimethylthiazol-2-yl)-2,5-diphenyltetrazolium bromide (MTT) in a colorimetric assay. See Pauwels et al. (1988) *J. Virol Methods* 20:309-321. Virus and control OD values are averaged over six determinations. Percent inhibition of HIV cytopathic effect (CPE) is calculated by the following formula: [(average OD−virus control OD/(cell control OD−virus control OD)]×100. Cytotoxicity is determined by the incubation in duplicate with serial dilutions of compound in the absence of virus. Percent cytotoxicity is determined according to the following formula: (average OD/cell control OD)×100. The $EC_{50}$ represents the concentration of compound that gave 50% inhibition of the cytopathic effect. The $CCIC_{50}$ is the concentration of compound which gives a 50% cytotoxic effect. It is noted that when conjugation of the water-soluble, non-peptidic oligomer occurs at the hydroxyl group located at 26 position of saquinavir, no anti-HIV activity is measured. See Table 1, Example 3. While not wishing to be bound by theory, it appears that the availability of this hydroxyl group is required for activity (a "binding hydroxyl group"). As a consequence, it is preferred in some embodiments that the conjugate lacks attachment of the water-soluble, non-peptidic oligomer at a binding hydroxyl group. A "binding hydroxyl group" for any given protease inhibitor can be determined by one of ordinary skill in the art by, for example, experimental testing and/or by comparing the structure of the protease inhibitor of interest with the structure of saquinavir and determining which hydroxyl group in the protease inhibitor corresponds to the "binding hydroxyl group" at position 26 in saquinavir.

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition will vary depending on a number of factors, but will optimally be a therapeutically effective dose when the composition is stored in a unit dose container. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical compositions can take any number of forms and the invention is not limited in this regard. Exemplary preparations are most preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (typically as a lyophilizate or precipitate, which can be in the form of a powder or cake), as well as formulations prepared for injection, which are typically liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, each typically being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The conjugate can also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure can contain a single reservoir, or it can contain multiple reservoirs.

The conjugate can also be formulated into a suppository for rectal administration. With respect to suppositories, the conjugate is mixed with a suppository base material which is (e.g., an excipient that remains solid at room temperature but softens, melts or dissolves at body temperature) such as coca butter (theobroma oil), polyethylene glycols, glycerinated gelatin, fatty acids, and combinations thereof. Suppositories can be prepared by, for example, performing the following steps (not necessarily in the order presented): melting the suppository base material to form a melt; incorporating the conjugate (either before or after melting of the suppository base material); pouring the melt into a mold; cooling the melt (e.g., placing the melt-containing mold in a room temperature environment) to thereby form suppositories; and removing the suppositories from the mold.

The invention also provides a method for administering a conjugate as provided herein to a patient suffering from a condition that is responsive to treatment with the conjugate. The method comprises administering, generally orally, a therapeutically effective amount of the conjugate (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

In instances where parenteral administration is utilized, it may be necessary to employ somewhat bigger oligomers than those described previously, with molecular weights ranging from about 500 to 30K Daltons (e.g., having molecular weights of about 500, 1000, 2000, 2500, 3000, 5000, 7500, 10000, 15000, 20000, 25000, 30000 or even more).

The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature and/or can be determined experimentally. Generally, a therapeutically effective amount is an amount within one or more of the following ranges: from 0.001 mg/day to 10000 mg/day; from 0.01 mg/day to 7500 mg/day; from 0.10 mg/day to 5000 mg/day; from 1 mg/day to 4000 mg/day; and from 10 mg/day to 2000 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

One advantage of administering the conjugates of the present invention is that a reduction in first pass metabolism may be achieved relative to the parent drug. Such a result is advantageous for many orally administered drugs that are substantially metabolized by passage through the gut. In this way, clearance of the conjugate can be modulated by selecting the oligomer molecular size, linkage, and position of covalent attachment providing the desired clearance properties. One of ordinary skill in the art can determine the ideal molecular size of the oligomer based upon the teachings herein. Preferred reductions in first pass metabolism for a conjugate as compared to the corresponding nonconjugated small drug molecule include: at least about 10%, at least about 20%, at least about 30; at least about 40; at least about 50%; at least about 60%, at least about 70%, at least about 80% and at least about 90%.

Thus, the invention provides a method for reducing the metabolism of an active agent. The method comprises the steps of: providing monodisperse or bimodal conjugates, each conjugate comprised of a moiety derived from a small molecule drug covalently attached by a stable linkage to a water-soluble oligomer, wherein said conjugate exhibits a reduced rate of metabolism as compared to the rate of metabolism of the small molecule drug not attached to the water-soluble oligomer; and administering the conjugate to a patient. Typically, administration is carried out via one type of administration selected from the group consisting of oral administration, transdermal administration, buccal administration, transmucosal administration, vaginal administration, rectal administration, parenteral administration, and pulmonary administration.

Although useful in reducing many types of metabolism (including both Phase I and Phase II metabolism) can be reduced, the conjugates are particularly useful when the small molecule drug is metabolized by a hepatic enzyme (e.g., one or more of the cytochrome P450 isoforms) and/or by one or more intestinal enzymes.

All articles, books, patents, patent publications and other publications referenced herein are incorporated by reference in their entireties. In the event of an inconsistency between the teachings of this specification and the art incorporated by reference, the meaning of the teachings in this specification shall prevail.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

All chemical reagents referred to in the appended examples are commercially available unless otherwise indicated. The preparation of PEG-mers is described in, for example, U.S. Patent Application Publication No. 2005/0136031. All oligo (ethylene glycol) methyl ethers employed in the Examples below were monodisperse and chromatographically pure, as determined by reverse phase chromatography.

Example 1

Synthesis of PEG-Saquinavir Conjugates;
Conjugation at the Saquinavir Hydroxyl Group at $C_{26}$ Position

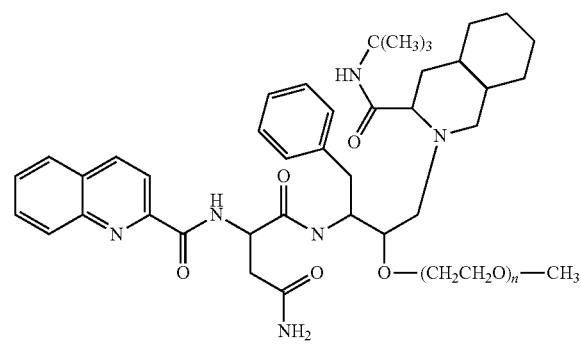

A. Synthesis of 26-m-PEG-3-O-Saquinavir (n=3)

NaH (60% in mineral oil, 72 mg, 1.8 mmole) was added into a solution of saquinavir free base (170 mg, 0.30 mmole) in dimethylformamide (5 ml). The mixture was stirred at room temperature under $N_2$ for 15 minutes, followed by the addition of Br—$(CH_2CH_2O)_3$—$CH_3$ (273 mg, 1.2 mmole) in dimethylformamide (1 ml). The resulting solution was then heated at 50° C. under $N_2$ in an oil bath for four hours. All solvents were then removed by using a rotary evaporator. Pure 26-m-PEG-3-O-Saquinavir was obtained by reverse phase preparative HPLC separation (76 mg, 0.093 mmole, 31% isolated yield).

Synthesis of 26-m-PEG-7-O-Saquinavir (n=7)

NaH (60% in mineral oil, 108 mg, 2.7 mmole) was added into a solution of saquinavir free base (300 mg, 0.45 mmole) in dimethylformamide (10 ml). The mixture was stirred at room temperature under $N_2$ for 15 minutes, followed by the addition of Br—$(CH_2CH_2O)_7$—$CH_3$ (724 mg, 1.8 mmole) in dimethylformamide (1 ml). The resulting solution was then heated at 50° C. under $N_2$ in an oil bath for four hours. All solvents were then removed by using a rotary evaporator. Pure 26-m-PEG-7-O-Saquinavir was obtained by reverse phase preparative HPLC separation (100 mg, 0.10 mmole, 22% isolated yield).

Example 2

Synthesis of PEG-Saquinavir Conjugates;
Conjugation at the Saquinavir Amide Group at $C_{15}$ Position

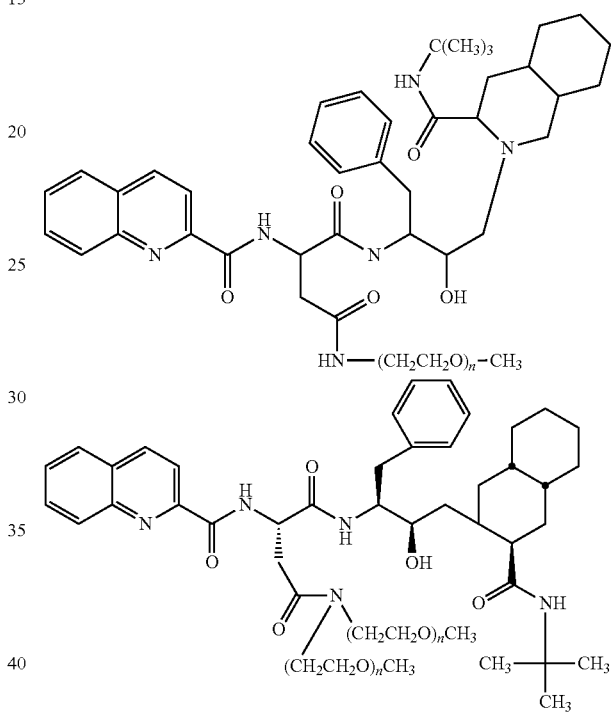

Synthesis of 15-m-PEG-7-NHCO-Saquinavir and 15-di-m-PEG-7-NCO-Saquinavir (n=7).

Synthesis of 26-MEM-O-Saquinavir. To an anhydrous tetrahydrofuran (~30 mL) solution of saquinavir free base (530 mg, 0.79 mmol) at −30° C. under $N_2$, butyl lithium (1.58 mmol, 0.63 mL, 2.5 M in hexane) was added through a syringe. After stirred at −30° C. for 5 minutes, MEMCl (118 mg, 0.95 mmol) in ~1 mL of anhydrous tetrahydrofuran was added. The reaction solution was slowly warmed up to room temperature and kept overnight (18 hours). HPLC showed that almost all free saquinavir was gone and 26-MEM-O-Saquinavir was formed in ~90% yield. After separation by a reverse phase preparative HPLC, pure 26-MEM-O-Saquinavir was obtained as a colorless solid.

Synthesis of 26-MEM-O-15-m-PEG-7-NHCO-Saquinavir. To a dimethylformamide (~8 mL) solution of 26-MEM-O-Saquinavir (50 mg, 0.066 mmole) was added sodium hydride (21 mg, 0.53 mmole, 60% in mineral oil). After stirring at room temperature for 15 minutes, Br—$(CH_2CH_2O)_7$—$CH_3$ (159 mg, 0.40 mmole) in ~1 mL of dimethylformamide was added. The reaction mixture was stirred at room temperature under nitrogen for two days. HPLC showed that 26-MEM-O-15-m-PEG-7-NHCO-Saquinavir was formed in ~50% yield. The reaction was then stopped by the addition of 0.1N hydrochloric acid solution (~3 mL) to destroy excess sodium hydride. All the solvents were removed by a rotary evaporator at 50° C. to give a sticky solid. The product was not purified and was used as such in the next synthetic step.

Synthesis of 15-m-PEG-7-NHCO-Saquinavir. The reaction mixture of 26-MEM-O-15-m-PEG-7-NHCO-Saquinavir was dissolved in ~10 mL of 2N hydrochloric acid methanol solution. The solution was stirred at room temperature for four days. HPLC showed that all MEM protection groups were removed and 15-m-PEG-7-NHCO-Saquinavir was formed in ~50% yield. After the reverse phase preparative HPLC separation, pure 15-m-PEG-7-NHCO-Saquinavir was obtained (35 mg, 0.035 mmole, 53% isolated yield), LC-MS: Calc: 993.2. Found: 993.5.

Synthesis of 26-MEM-O-15-di-m-PEG-7-NCO-Saquinavir. To a dimethylformamide (~5 mL) solution of 26-MEM-O-Saquinavir (30 mg, 0.040 mmole) was added sodium hydride (26 mg, 0.64 mmole, 60% in mineral oil). After stirring at room temperature for 15 minutes, Br—$(CH_2CH_2O)_7$—$CH_3$ (96 mg, 0.24 mmole) in ~1 mL of dimethylformamide was added. The reaction mixture was stirred at room temperature under nitrogen for two days. HPLC showed that 26-MEM-O-15-di-m-PEG-7-NCO-Saquinavir was formed in ~23% yield. The reaction was then stopped by the addition of 0.1N hydrochloric acid solution (~3 mL) to destroy excess sodium hydride. All the solvents were removed by a rotary evaporator at 50° C. to give a sticky solid. The product was not purified and was used as such for the next synthetic step.

Synthesis of 15-di-m-PEG-7-NCO-Saquinavir. The reaction mixture of 26-MEM-O-di-15-m-PEG-7-NCO-Saquinavir was dissolved in ~10 mL of 2N hydrochloric acid methanol solution. The solution was stirred at room temperature overnight. HPLC showed that all MEM protection groups were removed and 15-di-m-PEG-7-NCO-Saquinavir was formed in ~37% yield. After the reverse phase preparative HPLC separation, pure 15-di-m-PEG-7-NCO-Saquinavir was obtained (11 mg, 0.0084 mmole, 21% isolated yield), LC-MS: Calc: 1315.6. Found: 1315.6.

Synthesis of 15-m-PEG-3-NHCO-Saquinavir (n=3)
Synthesis of 26-MEM-O-15-m-PEG-3-NHCO-Saquinavir. To a dimethylformamide (~20 mL) solution of 26-MEM-O-Saquinavir (88 mg, 0.12 mmole) was added sodium hydride (37 mg, 0.92 mmole, 60% in mineral oil). After stirring at room temperature for 15 minutes, Br—$(CH_2CH_2O)_3$—$CH_3$ (158 mg, 0.70 mmole) in ~1 mL of dimethylformamide was added. The reaction mixture was stirred at room temperature under nitrogen overnight (~23 hours). HPLC showed that 26-MEM-O-15-m-PEG-3-NHCO-Saquinavir was formed in ~47% yield. The reaction was then stopped by the addition of 0.1N hydrochloric acid solution (~3 mL) to destroy excess sodium hydride. All the solvents were removed by a rotary evaporator at 50° C. to give a sticky solid. The product was not purified and was used as such for the next synthetic step.

Synthesis of 15-m-PEG-3-NHCO-Saquinavir. The crude 26-MEM-O-15-m-PEG-3-NHCO-Saquinavir product was dissolved in ~30 mL of 2N hydrochloric acid methanol solution. The solution was stirred at room temperature for four hours. HPLC showed that all MEM protection groups were removed and 15-m-PEG-3-NHCO-Saquinavir was formed in ~41% yield. After the reverse phase preparative HPLC separation, pure 15-m-PEG-3-NHCO-Saquinavir was obtained (20 mg, 0.024 mmole, 20% isolated yield), LC-MS: Calc: 817.0. Found: 817.5.

Synthesis of 15-m-PEG-5-NHCO-Saquinavir (n=5)
Synthesis of 26-MEM-O-15-m-PEG-5-NHCO-Saquinavir. To a dimethylformamide (~30 mL) solution of 26-MEM-O-Saquinavir (140 mg, 0.18 mmole) was added sodium hydride (59 mg, 1.48 mmole, 60% in mineral oil). After stirring at room temperature for 15 minutes, Br—$(CH_2CH_2O)_5$—$CH_3$ (349 mg, 1.11 mmole) in ~1 mL of dimethylformamide was added. The reaction mixture was stirred at room temperature under nitrogen for two days. HPLC showed that 26-MEM-O-15-m-PEG-5-NHCO-Saquinavir was formed in ~52% yield. The reaction was then stopped by the addition of 0.1N hydrochloric acid solution (~3 mL) to destroy excess sodium hydride. All the solvents were removed by a rotary evaporator at 50° C. to give a sticky solid. The product was not purified and was used as such for the next synthetic step.

Synthesis of 15-m-PEG-5-NHCO-Saquinavir. The reaction mixture of 26-MEM-O-15-m-PEG-5-NHCO-Saquinavir was dissolved in ~15 mL of 2N hydrochloric acid methanol solution. The solution was stirred at room temperature for four hours. HPLC showed that all MEM protection groups were removed and 15-m-PEG-5-NHCO-Saquinavir was formed in ~50% yield. After the reverse phase preparative HPLC separation, pure 15-m-PEG-5-NHCO-Saquinavir was obtained (32 mg, 0.035 mmole, 20% isolated yield), LC-MS: Calc: 905.1. Found: 905.5.

Example 3

Evaluation for Anti-HIV-1 Efficacy in CEM-SS Cells

Compounds were tested at a 1.0 µM high-test concentration in DMSO. CEM-SS cells were passaged in T-75 flasks prior to use in the antiviral assay. On the day preceding the assay, the cells were split 1:2 in order to assure they were in exponentional growth phase at the time of infection. Total cell and viability quantification was performed using a hemacytometer and trypan blue exclusion. Cell viability was greater than 95% for the cells to be utilized in the assay. The cells were resuspended at $5 \times 10^4$ cells/mL in tissue culture medium and added to the drug-containing microtiter plates in a volume of 50 µL.

The virus used was the lymphocytropic virus strain HIV-$1_{RF}$. This virus was obtained from the NIH AIDS research and Reference Reagent Program and was grown in CEM-SS cells for the production of stock virus pools. For each assay, a pre-titered aliquot of virus was removed from the freezer and allowed to thaw slowly to room temperature in a biological safety cabinet. The virus was resuspended and diluted into tissue culture medium such that the amount of virus added to each well in a volume of 50 µL was the amount determined to give approximately 90% cell killing in six days post-infection. $TCID_{50}$ calculations by endpoint titration in CEM-SS cells indicated that the multiplicity of infection in these assays was approximately 0.01.

Each plate contains cell control wells (cells only), virus control wells (cells plus virus), compound cytotoxicity wells (cells plus compound only), compound colorimetric control wells (compound only), as well as experimental wells (compound plus cells plus virus). Samples were evaluated with triplicate measurements for antiviral efficacy and duplicate measurements for cytotoxicity. Six concentrations at half-log dilutions were used in order to determine the $IC_{50}$ values and to measure cellular cytotoxicity, if detectable.

At assay termination, the assay plates were stained with the soluble tetrazolium-based dye MTS (CellTiter Reagent, Promega) to determine cell viability and quantify compound cytotoxicity. MTS is metabolized by the mitochondrial enzymes of metabolically active cells to yield a soluble formazan product, allowing the rapid quantitative analysis of cell viability and compound cytotoxicity. The MTS is a stable solution that does not require preparation before use. At termination of the assay, 20 μL of MTS reagent was added per well. The wells were incubated for four to six hours at 37° C. Adhesive plate sealers were used in place of the lids, the seal plate was inverted several times to mix the soluble formazan product and the plate was read spectrophotometrically at 490/650 nm with a Molecular Devices Vmax plate reader.

Using a computer program (Southern Research Institute, Frederick Md.), various values were determined including $IC_{50}$ (50%, inhibition of virus replication), $TC_{50}$ (50% reduction in cell viability), and an antiviral index (antiviral index=$TC_{50}/IC_{50}$). Values are provided in Table 1, below.

TABLE 1

Anti-HIV-1 Efficacy in CEM-SS Cells

| Property | Saquinavir | 26-m-PEG-3-O-Saquinavir | 26-m-PEG-7-O-Saquinavir | 15-m-PEG-7-NHCO-Saquinavir | di-15-m-PEG-7-NCO-Saquinavir |
|---|---|---|---|---|---|
| In vitro Activity $IC_{50}$ (μM) | 0.002 | no activity | no activity | 0.05 | 0.56 |
| Cytotoxicity $TC_{50}$ (μM) | >0.10 | >1.00 | >1.00 | >1.00 | >1.00 |
| Antiviral Index | >26.3 | — | — | >19.6 | >1.8 |

Example 4

Synthesis of PEG-Atazanavir

PEG-atazanavir was prepared. Schematically, the approach followed for this example is shown below (compound numbers in bold in the schematic correspond to the compound numbers provided in the text of this Example 4 alone).

Schematic for Synthesizing the Reagent

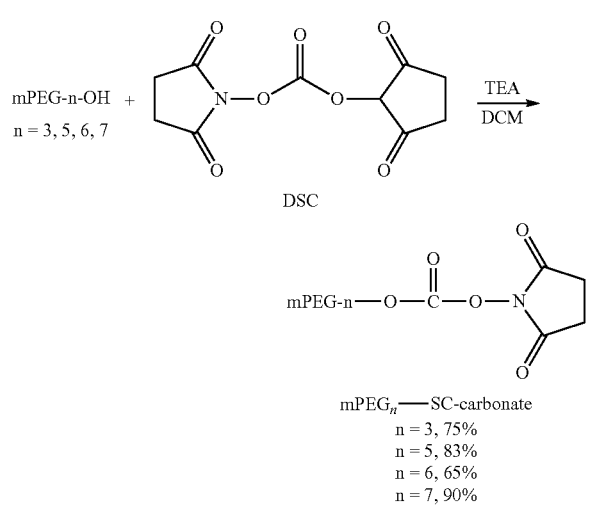

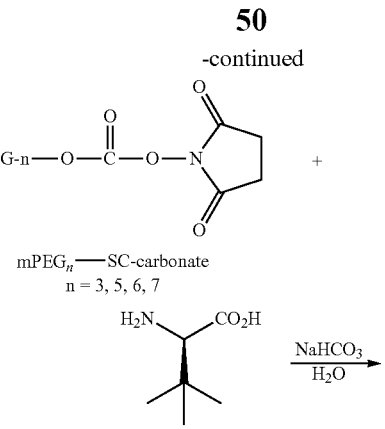

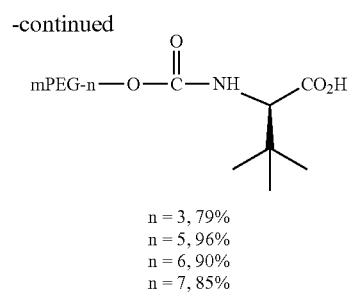

n = 3, 79%
n = 5, 96%
n = 6, 90%
n = 7, 85%

$mPEG_3$-SC-carbonate

Into a 100 mL flask was placed $mPEG_3$-OH (2.0 g, 12.1 mmol) and anhydrous dichloromethane (25 mL). The clear solution was cooled to 0° C., and then triethylamine (1.86 mL, 13.4 mmol, 1.1 equivalents) was added slowly. The solution was stirred for 15 minutes at 0° C., and then was added to a second flask containing a suspension of DSC (3.1 g, 12.1 mmol) in dichloromethane (20 mL). The reaction mixture was allowed to equilibrate to room temperature. After approximately 18 hours, the light-yellow reaction mixture was diluted with dichloromethane (60 mL), transferred to a separatory funnel, and partitioned with deionized water (100 mL). The aqueous layer was extracted with dichloromethane (4×80 mL). The combined organics were washed with water, saturated sodium bicarbonate, and saturated sodium chloride. The dried organic layer was filtered, concentrated under reduced pressure and dried overnight under high vacuum, to give 2.79 g (75%) of $mPEG_3$-SC-carbonate as a light yellow oil. $^1H$ NMR ($CDCl_3$) δ 4.40 (m, 2H), 3.80 (m, 2H), 3.70 (bs, 6H), 3.60 (m, 2H), 3.35 (s, 3H), 2.80 (s, 4H); LC/MS=306 (M+1).

$mPEG_5$-SC-carbonate

Into a 100 mL flask was placed $mPEG_5$-OH (2.0 g, 7.92 mmol) and anhydrous dichloromethane (15 mL). The clear solution was cooled to 0° C., and then triethylamine (1.32 mL, 9.51 mmol, 1.2 equivalents) was added slowly. The solution was stirred for 15 minutes at 0° C., and then was added to a second flask containing a suspension of DSC (2.02 g, 7.92 mmol) in dichloromethane (15 mL). The reaction mixture was allowed to equilibrate to room temperature. After approximately 18 hours, the light-yellow reaction mixture was diluted with dichloromethane (40 mL), transferred to a separatory funnel, and partitioned with deionized water (80 mL). The aqueous layer was extracted with dichloromethane (4×50 mL). The combined organics were washed with water, saturated sodium bicarbonate, and saturated sodium chloride. The dried organic layer was filtered, concentrated under reduced pressure and dried overnight under high vacuum, to give 2.59 g (83%) of mPEG$_5$-SC-carbonate as a light yellow oil. $^1$H NMR (CDCl$_3$) δ 4.45 (m, 2H), 3.75 (m, 2H), 3.68 (bs, 16H), 3.55 (m, 2H), 3.34 (s, 3H), 2.80 (s, 4H); LC/MS=394 (M+1).

mPEG$_6$-SC-carbonate

Into a 100 mL flask was placed mPEG$_6$-OH (2.0 g, 6.74 mmol) and anhydrous dichloromethane (12 mL). The clear solution was cooled to 0° C., and then triethylamine (1.12 mL, 8.10 mmol, 1.2 equivalents) was added slowly. The solution was stirred for 15 minutes at 0° C., and then was added to a second flask containing a suspension of DSC (1.73 g, 6.74 mmol) in dichloromethane (15 mL). The reaction mixture was allowed to equilibrate to room temperature. After approximately 18 hours, the light-yellow reaction mixture was diluted with dichloromethane (50 mL), transferred to a separatory funnel, and partitioned with deionized water (80 mL). The aqueous layer was extracted with dichloromethane (4×50 mL). The combined organics were washed with water, saturated sodium bicarbonate, and saturated sodium chloride. The dried organic layer was filtered, concentrated under reduced pressure and dried overnight under high vacuum, to give 1.92 g (65%) of mPEG$_6$-SC-carbonate as a light yellow oil. $^1$H NMR (CDCl$_3$) δ 4.48 (m, 2H), 3.78 (m, 2H), 3.68 (bs, 20H), 3.58 (m, 2H), 3.38 (s, 3H), 2.84 (s, 4H); LC/MS=438 (M+1).

mPEG$_7$-SC-carbonate

Into a 100 mL flask was placed mPEG$_7$-OH (2.0 g, 5.87 mmol) and anhydrous dichloromethane (15 mL). The clear solution was cooled to 0° C., and then triethylamine (1.22 mL, 8.81 mmol, 1.5 equivalents) was added slowly. The solution was stirred for 15 minutes at 0° C., and then was added to a second flask containing a suspension of DSC (2.25 g, 8.81 mmol) in dichloromethane (15 mL). The reaction mixture was allowed to equilibrate to room temperature. After approximately 18 hours, the light-yellow reaction mixture was diluted with dichloromethane (50 mL), transferred to a separatory funnel, and partitioned with deionized water (80 mL). The aqueous layer was extracted with dichloromethane (4×50 mL). The combined organics were washed with water, saturated sodium bicarbonate, and saturated sodium chloride. The dried organic layer was filtered, concentrated under reduced pressure and dried overnight under high vacuum, to give 2.82 g (90%) of mPEG$_7$-SC-carbonate as a light yellow oil. $^1$H NMR (CDCl$_3$) δ 4.45 (m, 2H), 3.78 (m, 2H), 3.65 (bs, 24H), 3.58 (m, 2H), 3.39 (s, 3H), 2.85 (s, 4H); LC/MS=482 (M+1).

mPEG$_3$-L-tert-Leucine

Into a 125 mL flask was placed L-tert-Leucine (0.43 g, 3.27 mmol) and deionized water (12 mL). The solution was stirred for 30 minutes until clear, followed by the addition of solid sodium bicarbonate (1.27 g, 15.0 mmol, 4.6 equivalents). The cloudy solution was stirred at room temperature, under nitrogen. In a second flask the mPEG$_3$-SC-carbonate (1.24 g, 4.09 mmol, 1.25 equiv.) was taken up in deionized water (12 mL) and this solution was added all at once to the basic L-tert-Leucine solution. The cloudy light-yellow reaction mixture was stirred at room temperature, under nitrogen. After approximately 20 hours, the clear mixture was cooled to 0° C., and carefully acidified with 2 N HCl to pH 1 (20 mL). The acidic mixture was transferred to a separatory funnel and partitioned with dichloromethane (50 mL) and additional water (50 mL). The aqueous layer was extracted with dichloromethane (4×50 mL). The combined organic layers were washed with water and saturated sodium chloride, and dried over sodium sulfate. The dried organic layer was filtered, concentrated under reduced pressure and dried under high vacuum overnight, to give 0.83 g (79%) of mPEG$_3$-L-tert-Leucine as a pale yellow oil. $^1$H NMR (CDCl$_3$) δ 5.45 (d, 1H), 4.26-4.35 (m, 2H), 4.14 (m, 1H), 3.70 (bs, 17H), 3.65 (m, 2H), 3.32 (s, 3H), 0.96 (s, 9H); LC/MS=322 (M+1).

mPEG$_5$-L-tert-Leucine

Into a 250 mL flask was placed L-tert-Leucine (0.68 g, 5.21 mmol) and deionized water (20 mL). The solution was stirred for 30 minutes until clear, followed by the addition of solid sodium bicarbonate (1.96 g, 23.3 mmol, 4.5 equivalents). The cloudy solution was stirred at room temperature, under nitrogen. In a second flask the mPEG$_5$-SC-carbonate (3) was taken up in deionized water (20 mL) and this solution was added all at once to the basic L-tert-Leucine solution. The cloudy light-yellow reaction mixture was stirred at room temperature, under nitrogen. After approximately 18 hours, the clear mixture was cooled to 0° C., and carefully acidified with 2 N HCl to pH 1 (18 mL). The acidic mixture was transferred to a separatory funnel and partitioned with dichloromethane (50 mL) and additional water (50 mL). The aqueous layer was extracted with dichloromethane (4×50 mL). The combined organic layers were washed with water and saturated sodium chloride, and dried over sodium sulfate. The dried organic layer was filtered, concentrated under reduced pressure and dried under high vacuum overnight, to give 2.04 g (96%) of mPEG$_5$-L-tert-Leucine as a pale yellow oil. $^1$H NMR (CDCl$_3$) δ 5.45 (d, 1H), 4.26-4.35 (m, 2H), 4.14 (m, 1H), 3.70 (bs, 17H), 3.65 (m, 2H), 3.38 (s, 3H), 1.02 (s, 9H); LC/MS=410 (M+1).

mPEG$_6$-L-tert-Leucine

Into a 250 mL flask was placed L-tert-Leucine (0.45 g, 3.47 mmol) and deionized water (15 mL). The solution was stirred for 30 minutes until clear, followed by the addition of solid sodium bicarbonate (1.31 g, 15.6 mmol, 4.5 equivalents). The cloudy solution was stirred at room temperature, under nitrogen. In a second flask the mPEG$_6$-SC-carbonate (1.9 gm, 4.34 mmol, 1.25 equiv.) was taken up in deionized water (15 mL) and this solution was added all at once to the basic L-tert-Leucine solution. The cloudy light-yellow reaction mixture was stirred at room temperature, under nitrogen. After approximately 18 hours, the clear mixture was cooled to 0° C., and carefully acidified with 2 N HCl to pH 1 (10 mL). The acidic mixture was transferred to a separatory funnel and partitioned with dichloromethane (50 mL) and additional water (50 mL). The aqueous layer was extracted with dichloromethane (4×50 mL). The combined organic layers were washed with water and saturated sodium chloride, and dried over sodium sulfate. The dried organic layer was filtered, concentrated under reduced pressure and dried under high vacuum overnight, to give 1.39 g (90%) of mPEG$_6$-L-tert-Leucine as a pale yellow oil. $^1$H NMR (CDCl$_3$) δ 5.47 (d, 1H), 4.10-4.30 (m, 2H), 4.14 (m, 1H), 3.70 (bs, 20H), 3.65 (m, 2H), 3.38 (s, 3H), 1.02 (s, 9H); LC/MS=454 (M+1).

mPEG$_7$-L-tert-Leucine

Into a 250 mL flask was placed L-tert-Leucine (0.31 g, 2.32 mmol) and deionized water (15 mL). The solution was stirred for 30 min until clear, followed by the addition of solid sodium bicarbonate (0.89 g, 10.6 mmol, 4.5 equivalents). The cloudy solution was stirred at room temperature, under nitrogen. In a second flask the mPEG$_7$-SC-carbonate (1.4 gm, 2.91 mmol, 1.25 equiv.) was taken up in deionized water (15 mL) and this solution was added all at once to the basic L-tert-Leucine solution. The cloudy light-yellow reaction mixture was stirred at room temperature, under nitrogen. After approximately 18 hours, the clear mixture was cooled to 0° C., and carefully acidified with 2 N HCl to pH 1 (8 mL). The acidic mixture was transferred to a separatory funnel and partitioned with dichloromethane (50 mL) and additional water (50 mL). The aqueous layer was extracted with dichloromethane (4×50 mL). The combined organic layers were washed with water and saturated sodium chloride, and dried over sodium sulfate. The dried organic layer was filtered, concentrated under reduced pressure and dried under high vacuum overnight, to give 1.0 g (85%) of mPEG$_7$-L-tert-Leucine as a pale yellow oil. $^1$H NMR (CDCl$_3$) δ 5.46 (d, 1H), 4.10-4.25 (m, 2H), 4.14 (m, 1H), 3.70 (bs, 24H), 3.65 (m, 2H), 3.38 (s, 3H), 1.02 (s, 9H); LC/MS=498 (M+1).

Schematic for Synthesizing PEG-Atazanavir

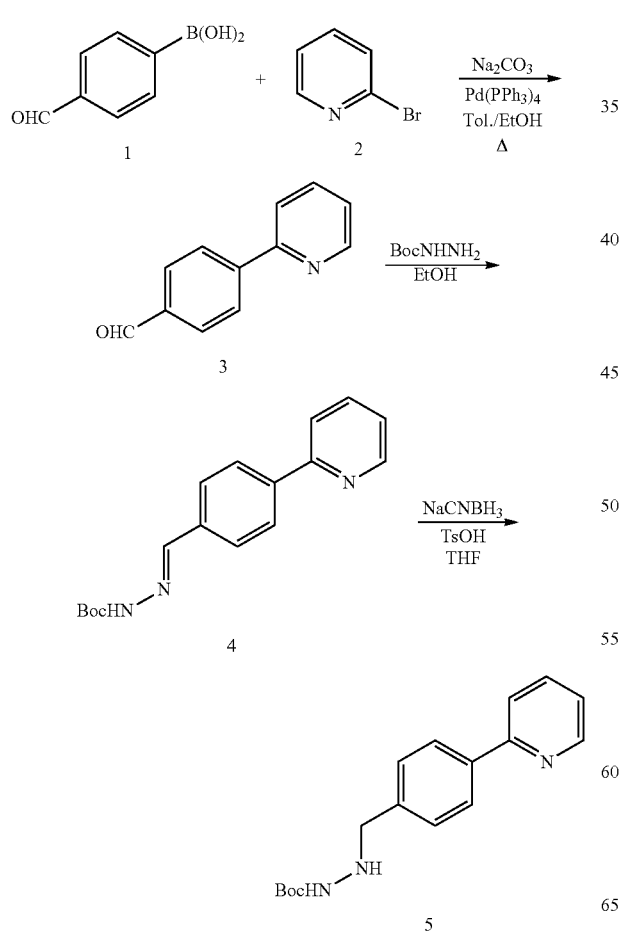

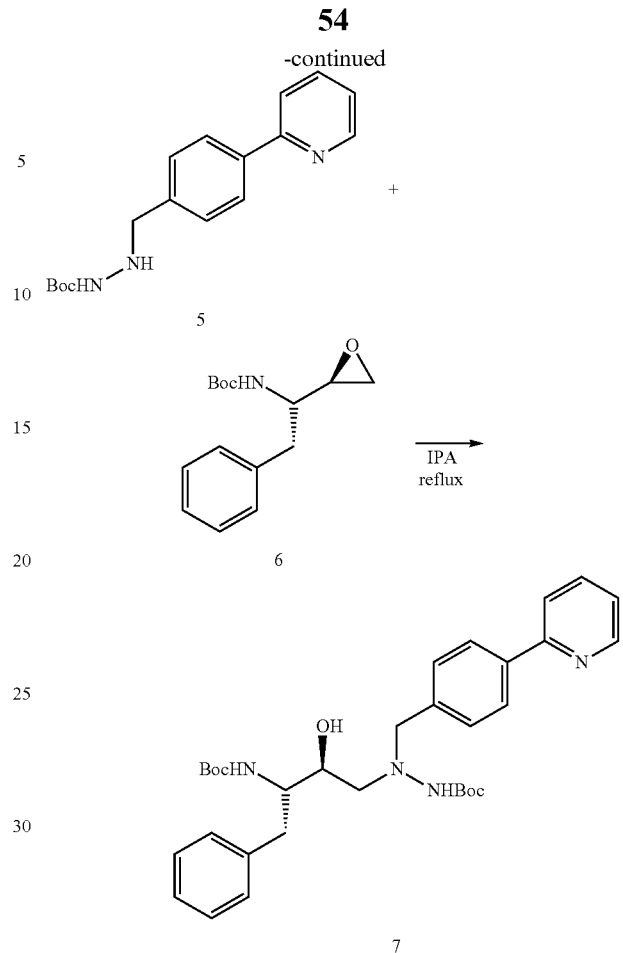

Methods

All reactions with air- or moisture-sensitive reactants and solvents were carried out under nitrogen atmosphere. In general, reagents and solvents (except PEG-based reagents) were used as purchased without further purification. Analytical thin-layer chromatography was performed on silica F$_{254}$ glass plates (Biotage). Components were visualized by UV light of 254 nm or by spraying with phosphomolybdic acid. Flash chromatography was performed on Biotage SP4 system. $^1$H NMR spectra: Bruker 300 MHz; chemical shifts of signals are expressed in parts per million (ppm) and are referenced to the deuterated solvents used. MS spectra: rapid resolution Zorbax C18 column; 4.6×50 mm; 1.8 μm. HPLC method had the following parameters: column, Betasil C18, 5-μm (100×2.1 mm); flow, 0.5 mL/minute; gradient, 0-23 minutes, 20% acetonitrile/0.1% TFA in water/0.1% TFA to 100% acetonitrile/0.1% TFA; detection, 230 nm. t$_R$ refers to the retention time. Abbreviations: TPTU, O-(1,2-Dihydro-2-oxo-1-pyridyl)-N,N,N',N'-tetramethyluroniumtetrafluoroborate; DIPEA, N,N'-Diisopropylethylamine.

4-Pyridin-2-yl-benzaldehyde (3)

A mixture of 4-formyl-phenylboronic acid (5.0 g, 33.0 mmol) and 2-bromopyridine (5.53 g, 35.0 mmol, 1.05 equiv.) in 265 mL of 4:3 toluene/95% ethanol was degassed with nitrogen for 30 minutes and then heated under a nitrogen atmosphere, resulting in a clear solution. A slurry of Pd(PPh$_3$)$_4$ (0.77 g) in 50 mL of a 4:4 mixture of toluene and 95% ethanol was added, followed by 50 mL of 3M aqueous Na$_2$CO$_3$. The resulting mixture was gently refluxed at 77° C. After 16 hours, the reaction mixture was cooled to room temperature, and the solid removed by filtration. The filtrate was transferred to a separatory funnel, and the layers separated. The aqueous layer was extracted with toluene (3×50 mL). The combined organics were washed with water, then saturated sodium chloride, and dried over sodium sulfate. The solution was filtered, and the filtrate concentrated under reduced pressure to give a yellow oil. Purification by Biotage chromatography (40+M cartridge; gradient, 0 to 5% methanol/dichloromethane) gave 4.13 g (68%) of (3) as a light-yellow solid. TLC R$_f$ (hexane/ethyl acetate, 2:1)=0.25; $^1$H NMR (CDCl$_3$) δ 10.1 (s, HCO), 8.77 (d, 1H), 8.20 (d, 2H), 8.00 (d, 2H), 7.81 (m, 2H), 7.31 (q, 1H); MS (M)$^+$=184; HPLC t$_R$ 1.2 minutes.

N-1-(tert-Butyloxycarbonyl)-N-2-[4-(pyridine-2-yl)benzylidene]-hydrazone (4)

To a 100 mL flask was added (3) (0.50 g, 2.73 mmol), tert-butyl carbazate (0.36 g, 2.73 mmol), 2-propanol (3.0 mL) and toluene (3.0 mL). The mixture was heated to reflux (85° C.) under inert atmosphere for two hours, cooled to room temperature gradually and stirred overnight under nitrogen. After 16 hours the reaction mixture was filtered, and the filter cake was washed with a cold mixture of toluene and hexane (1:3; 100 mL). The cake was dried under vacuum to afford 0.73 g (90%) of (4) as an off-white solid. TLC R$_f$ (hexane/ethyl acetate, 1:2)=0.38; $^1$H NMR (CDCl$_3$) δ 8.70 (d, 1H), 8.02 (m, 3H), 7.87 (s, 1H), 7.81 (s, 1H), 7.76 (m, 3H), 7.25 (m, 1H), 1.55 (s, 9H); MS (M)$^+$=298; HPLC t$_R$ 2.1 minutes.

N'-(4-Pyridin-2-yl-benzyl)-hydrazinecarboxylic acid tert-butyl ester (5)

Into a 100 mL flask was placed (4) (0.45 g, 1.50 mmol) in THF (3.0 mL). To this solution was added 99% sodium cyanoborohydride (0.12 g, 1.80 mmol, 1.2 equivalents), followed by a solution of p-TsOH (0.35 g, 1.80 mmol, 1.2 equivalents) in THF (3.0 mL). After 1.5 hours, additional p-TsOH (0.35 g, 1.80 mmol, 1.2 equivalents) in THF (3.0 mL) was added. After 16 hours at room temperature, the THF was removed under reduced pressure. The white residue was partitioned between ethyl acetate (35 mL) and water (35 mL). The aqueous layer was extracted with ethyl acetate (3×35 mL). The combined organics were washed with water, then saturated sodium chloride, and then dried over sodium sulfate. After filtration, concentration under reduced pressure, and drying under high vacuum for 6 h, 0.41 g (91%) of (5) was obtained as a white solid. TLC R$_f$ (hexane/ethyl acetate, 1:2)=0.30; $^1$H NMR (DMSO-d$_6$) δ 8.64 (d, 1H), 8.26 (sb, HN), 8.02 (d, 2H), 7.93 (d, 1H), 7.85 (dd, 1H), 7.42 (d, 2H), 7.32 (dd, 1H), 4.80 (m, HN), 3.92 (d, 2H), 1.38 (s, 9H); MS (M)=300; HPLC t$_R$ 7.0 minutes.

N'-(3-tert-Butoxycarbonylamino-2-hydroxy-4-phenyl-butyl)-N'-(4-pyridin-2-yl-benzyl)-hydrazinecarboxylic acid tert-butyl ester (7)

Into a 100 mL flask was placed (5) (1.0 g, 3.34 mmol), (6) (2S,3S)-1,2-epoxy-3-(Boc-amino)-4-phenylbutane (2.78 g, 10.5 mmol, 3.16 equivalents), and 2-propanol (15 mL). The reaction was heated to reflux. After approximately 61 hours of refluxing, the heat was removed, and the mixture cooled to room temperature. To the cooled mixture was added water/ice (50 mL). To the aqueous mixture was added dichloromethane (50 mL) and then transferred to a separatory funnel. The aqueous layer was extracted with dichloromethane (3×50 mL). The combined organics were washed with water, then saturated sodium chloride, and then dried over sodium sulfate. The dried organic solution was filtered, and the filtrate was concentrated under reduced pressure, and then dried under high vacuum overnight. The yellow foam was purified by Biotage chromatography (40+M cartridge; 0 to 5% methanol/dichloromethane over 25 CV) to give 1.24 g (66%) of (7) as a white solid. TLC R$_f$ (hexane/ethyl acetate, 1:2)=0.45; $^1$H NMR (CD$_3$OD) δ 8.60 (d, 1H), 7.88 (m 4H), 7.50 (d, 2H), 7.36 (m, 1H), 7.25 (m, 4H), 7.18 (m, 1H), 3.93 (m, 2H), 3.70 (m, 2H), 3.0-2.6 (m, 4H), 1.33 (s, 9H), 1.30 (s, 9H); MS (M)$^+$=563; HPLC t$_R$ 9.6 minutes.

3-Amino-4-phenyl-1-[N-(4-pyridin-2-yl-benzyl)-hydrazino]-butan-2-ol trihydrochloride (8)

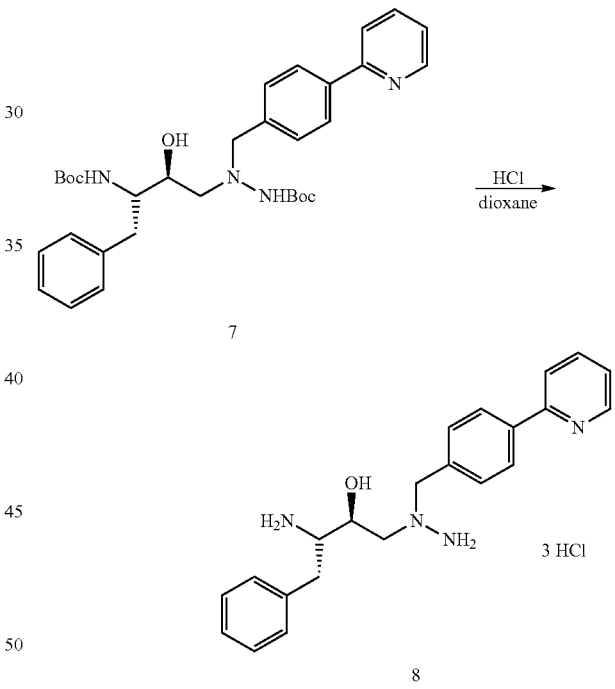

The Boc-aza-isostere (7) (1.2 g, 2.1 mmol) was taken up in 1,4-dioxane (16 mL), and stirred at room temperature, under nitrogen. After five minutes, 4N HCl (12 mL) was added via syringe. There was immediate precipitate formation, and the mixture was stirred at room temperature, under nitrogen. After approximately 18 hours, the dioxane was removed under reduced pressure. The yellow residue was azeotroped with toluene (3×25 mL), and then dried under high vacuum. After 6 hours under high vacuum, 0.92 g (91%) of (8) was obtained as a yellow solid. $^1$H NMR (CD$_3$OD) δ 8.87 (d, 1H), 8.69 (m, 1H), 8.42 (d, 1H), 8.06 (m, 3H), 7.80 (d, 2H), 7.28 (m, 6H), 4.25 (m, 3H), 3.13 (m, 2H), 2.88 (d, 2H); MS (M)$^+$=472.

Synthesis of di-mPEG$_n$-Atazanavir

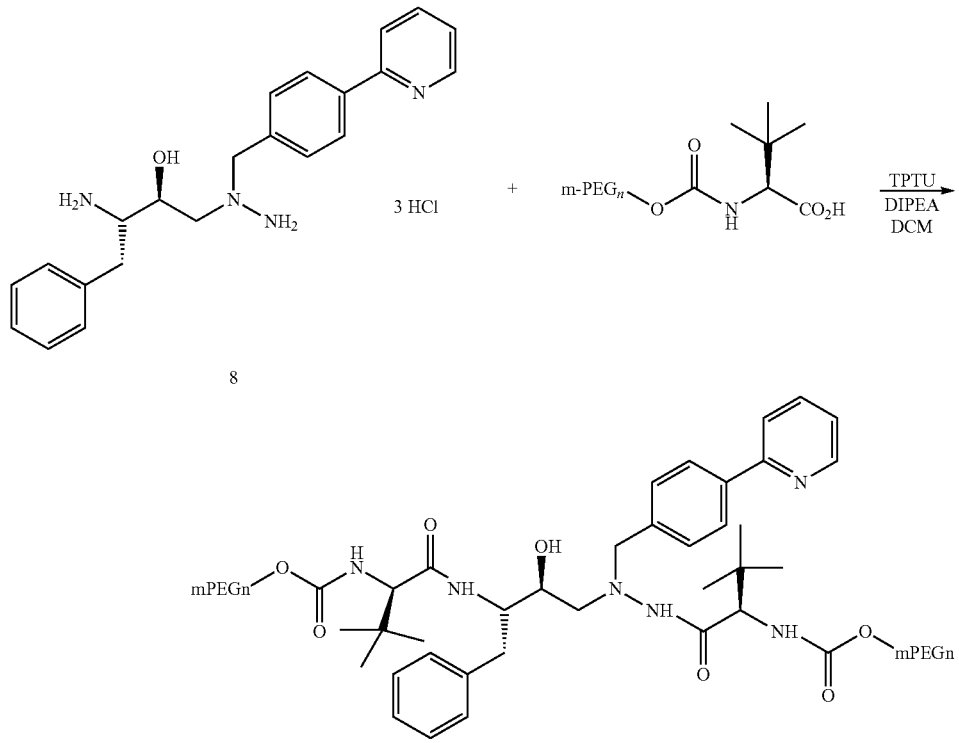

8

Synthesis of di-mPEG$_3$-Atazanavir

Into a 100 mL flask was placed mPEG$_3$-tert-Leucine (0.34 gm, 1.05 mmol, 3.0 equivalents) in anhydrous dichloromethane (3 mL) and cooled to 0° C. Next, TPTU (0.31 gm, 1.05 mmol, 3.0 equiv.), and Hunigs base (0.36 mL, 2.11 mmol, 6.0 equiv.) were added. The cloudy solution was stirred at 0° C. for 15 minutes, and then the diamino backbone trihydrochloride (8) (0.16 gm, 0.35 mmol) was added, as a solid, followed by a dichloromethane rinse (3 mL). The ice bath was removed and the reaction mixture allowed to equilibrate to room temperature. After approximately 20 hours, the reaction mixture was diluted with dichloromethane (20 mL). The mixture was transferred to a separatory funnel, and partitioned with deionized water (50 mL). The aqueous layer was extracted with dichloromethane (4×30 mL). The combined organics were washed with water, saturated sodium bicarbonate, and saturated sodium chloride. The organic layer was dried over sodium sulfate. The drying agent was filtered off, and the filtrate concentrated under reduced pressure to give a yellow oil. Purification was performed using Biotage (40+M cartridge; gradient elution: 0 to 5% methanol/dichloromethane) to give 0.14 gm (45%) of di-mPEG$_3$-Atazanavir as a clear oil. TLC R$_f$ (5% methanol/dichloromethane)=0.22; $^1$H NMR (CDCl$_3$) δ 8.71 (d, 1H), 7.98 (d, 2H), 7.81 (m, 2H), 7.45 (d, 2H), 7.10-7.30 (m, 10H), 6.22 (d, 1H), 5.35 (d, 1H), 4.25 (m, 4H), 4.01 (m, 4H), 3.50-3.80 (m, 24H), 3.38 (s, 3H), 2.70-3.0 (m, 4H), 0.85 (d, 18H); MS (M)$^+$=969; HPLC t$_R$ 7.85 minutes. (96% purity).

di-mPEG$_5$-Atazanavir

Into a 100 mL flask was placed m-PEG$_5$-tert-Leucine (2.0 gm, 4.88 mmol, 4.6 equiv.) in anhydrous dichloromethane (10 mL) and cooled to 0° C. Then added TPTU (1.45 gm, 4.88 mmol, 4.6 equiv.), and Hunigs base (1.85 mL, 10.6 mmol, 10.0 equiv.) The cloudy solution was stirred at 0° C. for 15 minutes, and then the diamino backbone trihydrochloride (8) (0.50 gm, 1.06 mmol) was added, as a solid, followed by a dichloromethane rinse (10 mL). The ice bath was removed and the reaction mixture allowed to equilibrate to room temperature. After approximately 20 hours, the reaction mixture was diluted with dichloromethane (40 mL). The mixture was transferred to a separatory funnel, and partitioned with deionized water (60 mL). The aqueous layer was extracted with dichloromethane (4×50 mL). The combined organics were washed with water, saturated sodium bicarbonate, and saturated sodium chloride. The organic layer was dried over sodium sulfate. The drying agent was filtered off, and the filtrate concentrated under reduced pressure to give a yellow oil. Purification was performed using Biotage (40+M cartridge; gradient elution: 0 to 5% methanol/dichloromethane) to give 0.70 gm (58%) of di-mPEG$_5$-Atazanavir as a light-yellow oil. TLC R$_f$ (5% methanol/dichloromethane)=0.23; $^1$H NMR (CDCl$_3$) δ 8.60 (d, 1H), 7.88 (d, 2H), 7.65 (m, 2H), 7.38 (d, 2H), 7.10-7.25 (m, 8H), 6.18 (d, 1H), 5.30 (m, 2H), 4.15 (m, 4H), 3.92 (m, 3H), 3.45-3.65 (m, 40H), 3.30 (s, 3H), 2.65-2.90 (m, 4H), 0.80 (d, 18H); MS (M)$^+$=1146; HPLC t$_R$ 7.72 minutes. (98% purity).

di-mPEG$_6$-Atazanavir

Into a 100 mL flask was placed mPEG$_6$-tert-Leucine (0.81 gm, 1.78 mmol, 3.0 equiv.) in anhydrous dichloromethane (3 mL) and cooled to 0° C. Next, EDC (0.34 gm, 1.78 mmol, 3.0 equiv.) and HOBT (0.24 gm, 1.78 mmol, 3.0 equiv.) were added. The cloudy solution was stirred at 0° C. for 15 minutes, and then the diamino backbone trihydrochloride (8) was added (0.28 gm, 0.59 mmol), as a solid, followed by a dichloromethane rinse (5 mL). The ice bath was removed and the reaction mixture allowed to equilibrate to room temperature. After approximately 28 hours, the reaction mixture was diluted with dichloromethane (35 mL). The mixture was transferred to a separatory funnel, and partitioned with deionized water (60 mL). The aqueous layer was extracted with dichloromethane (4×50 mL). The combined organics were washed with water, saturated sodium bicarbonate, and saturated sodium chloride. The organic layer was dried over sodium sulfate. The drying agent was filtered off, and the filtrate concentrated under reduced pressure to give a yellow oil. Purification was performed using Biotage (40+M cartridge; gradient elution: 0 to 5% methanol/dichloromethane) to give 0.27 gm (40%) of di-mPEG$_6$-Atazanavir as a clear oil. TLC R$_f$ (5% methanol/dichloromethane)=0.17; $^1$H NMR (CDCl$_3$) δ 8.75 (d, 1H), 78.02 (d, 2H), 7.85 (m, 2H), 7.50 (d, 2H), 7.10-7.25 (m, 6H), 6.22 (d, 1H), 5.40 (m, 2H), 4.20 (m, 4H), 4.15 (m, 3H), 3.52-3.70 (m, 48H), 3.38 (s, 3H), 2.75-2.92 (m, 4H), 0.85 (d, 18H); MS (M)$^+$=1234; HPLC t$_R$ 7.70 min. (96% purity).

di-mPEG$_7$-Atazanavir:

Into a 100 mL flask was placed mPEG$_7$-tert-Leucine (2.13 gm, 4.29 mmol, 4.6 equiv.) in anhydrous dichloromethane (10 mL) and cooled to 0° C. Then added TPTU (1.28 gm, 4.29 mmol, 4.6 equiv.), and Hunigs base (1.14 mL, 6.53 mmol, 7.0 equiv.) The cloudy solution was stirred at 0° C. for 15 minutes, and then the diamino backbone trihydrochloride (0.44 gm, 0.93 mmol) was added, as a solid, followed by a dichloromethane rinse (10 mL). The ice bath was removed and the reaction mixture allowed to equilibrate to room temperature. After approximately 22 hours, the reaction mixture was diluted with dichloromethane (30 mL). The mixture was transferred to a separatory funnel, and partitioned with deionized water (50 mL). The aqueous layer was extracted with dichloromethane (4×50 mL). The combined organics were washed with water, saturated sodium bicarbonate, and saturated sodium chloride. The organic layer was dried over sodium sulfate. The drying agent was filtered off, and the filtrate concentrated under reduced pressure to give a yellow oil. Purification was performed using Biotage (40+M cartridge; gradient elution: 0 to 5% methanol/dichloromethane) to give 0.47 gm (38%) of di-mPEG$_7$-Atazanavir as a light-yellow oil. $^1$H NMR (CDCl$_3$) δ 8.60 (d, 1H), 7.90 (d, 2H), 7.70 (m, 2H), 7.35 (d, 2H), 7.10-7.25 (m, 8H), 6.12 (d, 1H), 5.30 (m, 2H), 4.10 (m, 4H), 3.92 (m, 3H), 3.50-3.70 (m, 56H), 3.28 (s, 3H), 2.62-2.90 (m, 4H), 0.78 (d, 18H); MS (M)$^+$=1321; HPLC t$_R$ 7.69 min. (96% purity).

Example 5

Synthesis of PEG-Darunavir—"Approach A"

PEG-darunavir was prepared using a first approach. Schematically, the approach followed for this example is shown below (compound numbers in bold in the schematic correspond to the compound numbers provided in the text of this Example 5 alone).

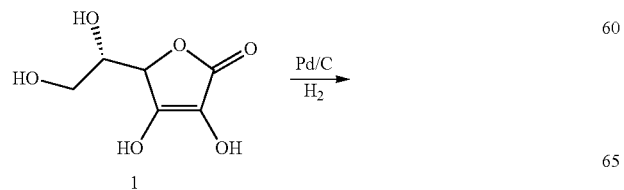

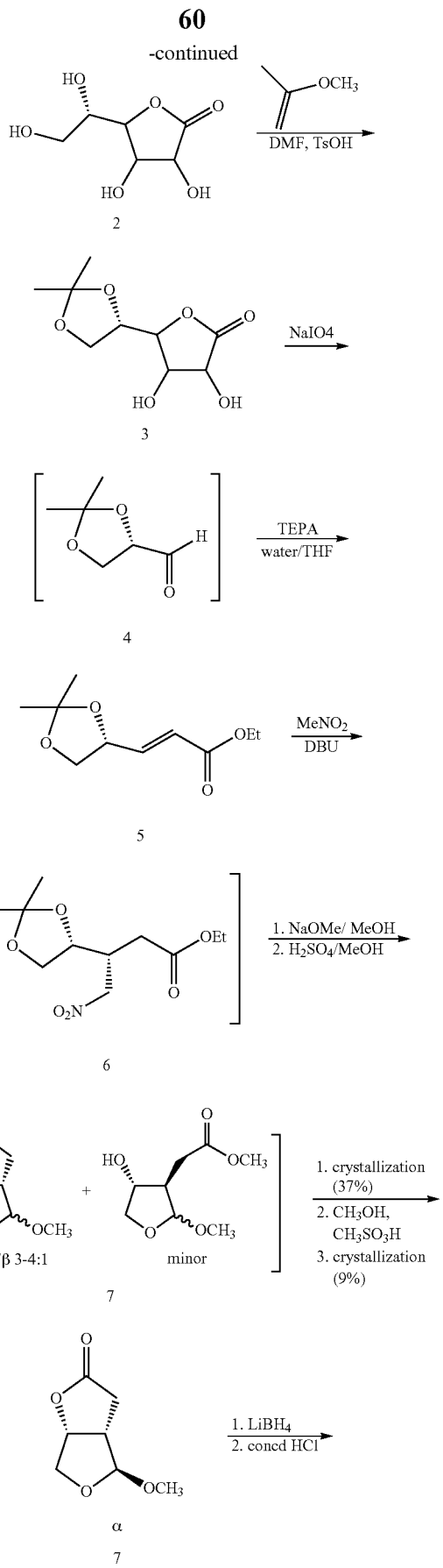

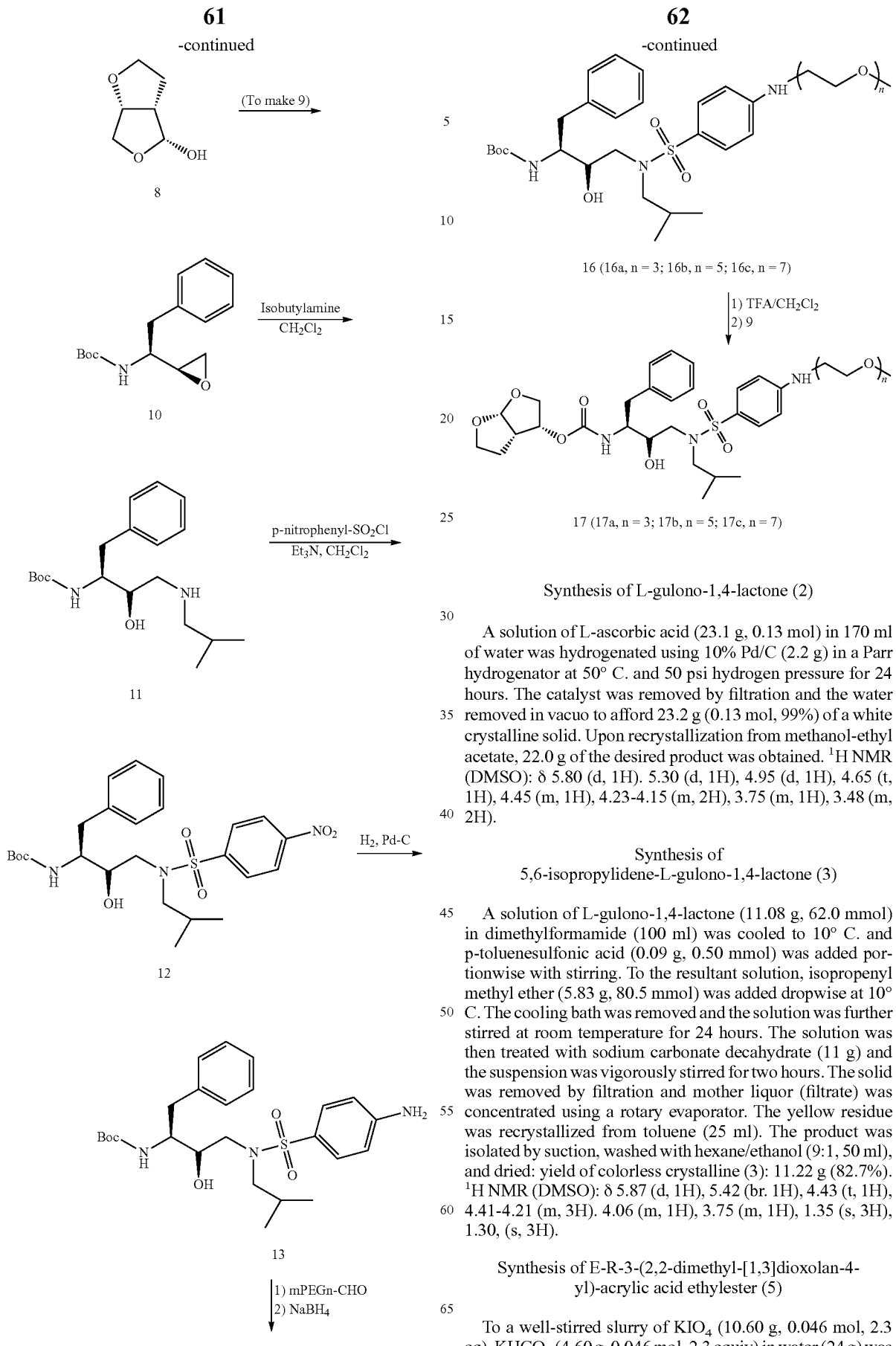

Synthesis of L-gulono-1,4-lactone (2)

A solution of L-ascorbic acid (23.1 g, 0.13 mol) in 170 ml of water was hydrogenated using 10% Pd/C (2.2 g) in a Parr hydrogenator at 50° C. and 50 psi hydrogen pressure for 24 hours. The catalyst was removed by filtration and the water removed in vacuo to afford 23.2 g (0.13 mol, 99%) of a white crystalline solid. Upon recrystallization from methanol-ethyl acetate, 22.0 g of the desired product was obtained. $^1$H NMR (DMSO): δ 5.80 (d, 1H). 5.30 (d, 1H), 4.95 (d, 1H), 4.65 (t, 1H), 4.45 (m, 1H), 4.23-4.15 (m, 2H), 3.75 (m, 1H), 3.48 (m, 2H).

Synthesis of 5,6-isopropylidene-L-gulono-1,4-lactone (3)

A solution of L-gulono-1,4-lactone (11.08 g, 62.0 mmol) in dimethylformamide (100 ml) was cooled to 10° C. and p-toluenesulfonic acid (0.09 g, 0.50 mmol) was added portionwise with stirring. To the resultant solution, isopropenyl methyl ether (5.83 g, 80.5 mmol) was added dropwise at 10° C. The cooling bath was removed and the solution was further stirred at room temperature for 24 hours. The solution was then treated with sodium carbonate decahydrate (11 g) and the suspension was vigorously stirred for two hours. The solid was removed by filtration and mother liquor (filtrate) was concentrated using a rotary evaporator. The yellow residue was recrystallized from toluene (25 ml). The product was isolated by suction, washed with hexane/ethanol (9:1, 50 ml), and dried: yield of colorless crystalline (3): 11.22 g (82.7%). $^1$H NMR (DMSO): δ 5.87 (d, 1H), 5.42 (br. 1H), 4.43 (t, 1H), 4.41-4.21 (m, 3H). 4.06 (m, 1H), 3.75 (m, 1H), 1.35 (s, 3H), 1.30, (s, 3H).

Synthesis of E-R-3-(2,2-dimethyl-[1,3]dioxolan-4-yl)-acrylic acid ethylester (5)

To a well-stirred slurry of KIO$_4$ (10.60 g, 0.046 mol, 2.3 eq), KHCO$_3$ (4.60 g, 0.046 mol, 2.3 equiv) in water (24 g) was added dropwise a solution of L-5,6-O-isopropylidene-gulono-1,4-lactone (4.37 g, 0.020 mol) in water (2.70 g) and THF (22.90 g) during three hours at 32-34° C. The reaction mixture was stirred for 4.5 hours at 32° C. The reaction mixture was cooled to 5° C. and kept at this temperature for 14 hours. The solids were removed by filtration and the cake was washed with THF (3.0 mL) and with another portion of THF (4.0 mL) by reslurrying. To the filtrate was added dropwise under stirring triethyl phosphonoacetate (TEPA, 3.90 g, 0.017 mol) during 25 minutes at 13-17° C. Subsequently, $K_2CO_3$ (16.80 g) was added portionwise during 30 minutes at 17-25° C. The reaction mixture was stirred for another 17 hours at 20° C. The aqueous and THF phases were separated and the aqueous phase extracted twice with 100 mL of toluene. The combined THF and toluene phases were concentrated in vacuo giving 2.80 g of a light yellow liquid. $^1$H NMR indicated the presence of E-R-3-(2,2-dimethyl-[1,3]dioxolan-4-yl)-acrylic acid ethylester (5, 78%). Thus, the crude yield of (5) was 70% yield based on (3). Of the above residue, 0.50 g was purified by flash chromatography on silica gel using 3/7 (v/v) ethyl acetate/n-heptane as the eluent. This gave 0.37 g of (5) with a purity of 96%. $^1$H NMR (300 MHz, $CDCl_3$) δ 6.79 (1H, dd, J=16.0, 5.3 Hz), 6.01 (1H, dd, J=16.0, 0.9 Hz), 4.58 (1H, q, J=6.0 Hz), 4.16-4.06 (3H, m), 3.58 (1H, t, J=7.6 Hz), 1.35 (3H, s), 1.31 (3H, s), 1.20 (3H, t, J=7.0 Hz). $^{13}$C NMR (75 MHz, $CDCl_3$) δ 166.0 (C), 144.7 (CH), 122.4 (CH), 110.2 (C), 75.0 (CH), 68.8 ($CH_2$), 60.6 ($CH_2$), 26.5 ($CH_3$), 25.8 ($CH_3$), 14.2 ($CH_3$). LC-MS, calculated for $C_{10}H_{17}O_4$ (M+H$^+$) 201.1. found 201.1.

(3aS,4S,6aR)-4-Methoxy-tetrahydro-furo[3,4-b]furan-2(3H)-one (α-7)

To 1.75 g of non-chromatographed (5) (78 wt % pure, 1.37 g, 6.80 mmol) was added to nitromethane (458 mg, 7.50 mmol) in 5.0 mL of methanol and the solution was cooled to 10° C. Subsequently, DBU (1.03 g, 6.80 mmol) was added dropwise during 35 minutes at 10-21° C. After stirring for 18 hours at 20° C. the resulting dark-red solution was cooled to 0° C. and NaOMe (15 mL of 0.50 M solution in methanol, 7.50 mmol) was added dropwise over 30 minutes at 0° C. After 30 minutes stirring at 0° C. the reaction mixture was quenched into a solution of $H_2SO_4$ (2.43 g, 96%, 23.80 mmol) in methanol (2.43 g) at 0-5° C. by dropwise addition during three hours under vigorous stirring. After two hours stirring at 0-2° C. the reaction mixture was quenched into a stirred slurry of $KHCO_3$ (3.53 g) in water (6.80 mL) at 0-6° C. by dropwise addition during one hour. The pH was adjusted to 4.1 with $H_2SO_4$ (96%) at 0° C. After heating up to 20° C. the salts were removed by filtration and washed with ethyl acetate (3×3.75 mL). The wash liquor was used later on in the extractions. The mother liquor of the filtration was concentrated in vacuo to remove the methanol. To the resulting residue was added water (0.80 g) and the pH was adjusted to 4.1 with $H_2SO_4$ (96%). The resulting aqueous solution was extracted with ethyl acetate (7.0 mL, 4×5.0 mL). The combined organic phases were concentrated in vacuo at 35-40° C. The volatiles were coevaporated with isopropanol (3×1.40 g) giving a residue (1.46 g) consisting of a crude mixture of (α-7) and (β-7), which was dissolved in isopropanol (2.02 g) at 70° C. The insoluble material was removed and the filtrate was cooled resulting in spontaneous crystallization of (α-7). The crystals were isolated by filtration, washed with isopropanol (2×1.0 mL, 0° C.) and dried in vacuo at 40° C. until a constant weight was achieved giving (α-7) as an off-white crystalline product [390 mg, 37% yield based on (5)]. The purity was >99%. The mother liquor and wash liquors of the first (α-7) crystallization were concentrated in vacuo, methanol (1.20 mL) was added and the resulting mixture concentrated in vacuo. Methanol (1.20 mL) was added once more and the mixture concentrated in vacuo again. To the residue was added methanol (0.45 g) and methanesulfonic acid ($MeSO_3H$, 0.027 g, 0.28 mmol) and the solution was heated to reflux. After one hour at reflux (60-65° C.), the solution was cooled to 33° C., neutralized with triethylamine (0.029 g, 1.05 equiv based on $MeSO_3H$) and concentrated in vacuo. To the resulting residue was added isopropanol (1.20 mL) and the mixture was concentrated in vacuo to give 0.88 g of crude product. The residue was dissolved in isopropanol (0.37 g) at 47° C. The resulting solution was cooled down to 2° C. during 2.5 hours. The crystalline product was isolated by filtration, washed with isopropanol (3×0.20 mL, 0° C.) and dried in vacuo at 40° C. until a constant weight was achieved giving a second crop of (α-7) as an off-white crystalline product (0.098 g). The purity was >99%. Thus, the total yield of the first and second crop of (α-7) based on (5) was 46%.

The GC assay for compounds (α-7) and (β-7) was performed with an Agilent 6890 GC (EPC) and a CP-Sil 5 CB column (part number CP7680 (Varian) or equivalent) of 25 mm and with a film thickness of 5 μm using a column head pressure of 5.1 kPa, a split flow of 40 mL/minute and an injection temperature of 250° C. The used ramp was: initial temperature 50° C. (5 minutes), rate 10° C./minute, final temperature 250° C. (15 minutes). Detection was performed with an FID detector at a temperature of 250° C. The retention times were as follows: chlorobenzene (internal standard) 17.0 minutes, (α-7) 24.9 minutes, (β-7) 25.5 minutes. The retention time of (β-7) was determined by epimerizing pure (α-7) (as prepared above) to an approximately 3:1 mixture of (α-7) (β-7) in methanol using 0.2 equiv $MeSO_3H$ at ambient temperature during 16 hours ($^1$H NMR and GC-MS confirmed that only (β-7) had been formed). For the quantification of (β-7) it was assumed that the response factor of (β-7) was identical to that of (α-7). $^1$H NMR (300 MHz, $CDCl_3$) δ 5.15 (1H, dd, J=7.4, 3.8 Hz), 4.88 (1H, s), 4.10 (1H, d, J=11.1 Hz), 3.96 (1H, dd, J=10.9, 3.8 Hz), 3.33 (3H, s), 3.10-2.99 (1H, m), 2.84 (1H, dd, J=18.2, 11.0 Hz), 2.51 (1H, dd, J=18.3, 3.7 Hz). $^{13}$C NMR (75 MHz, $CDCl_3$) δ175.9 (C), 110.0 (CH), 83.0 (CH), 70.6 ($CH_2$), 54.5 ($CH_3$), 45.1 (CH), 31.7 ($CH_2$). LC-MS: calculated for $C_7H_{11}O_4$ (M+H$^+$) 159.06. found 159.06. e.e. >99% (as determined by GC).

(3R,3aS,6aR)-Hexahydro-furo[2,3-b]furan-3-ol (8)

To a solution of (α-7) (1.42 g, 9.0 mmol) in THF (8.0 g) was added dropwise during 30 minutes a 10% solution of $LiBH_4$ (2.16 g, 1.1 equiv) and the reaction mixture was stirred at 50° C. for 2.5 hours. The obtained suspension was cooled to −10° C. and a 32% aqueous HCl solution (1.36 g, 0.012 mol, 1.3 equiv based on $LiBH_4$) was added dropwise over a period of four hours keeping the temperature <−5° C. After stirring for an additional two hours at −10° C., triethylamine (1.325 g, 0.013 mol, 1.1 equiv based on HCl) was added dropwise over one hour keeping the temperature <0° C. The reaction mixture was warmed up and concentrated at atmospheric pressure to a residual weight of approximately 5.0 g, the residue taken up in ethyl acetate (18.0 g) and concentrated once more at atmospheric pressure to a residual weight of approximately 5.0 g. The residue was taken up in ethyl acetate (18.0 g), stirred at reflux for 15 minutes and cooled to 0° C. The salts were removed by filtration and washed with cold (0° C.) ethyl acetate (2×1.5 g). The combined filtrates were concentrated in vacuo at <40° C. to a colorless oil containing 0.94 g of (8) [7.23 mmol, 80% based on (α-7), purity 87 wt % based on $^1$H NMR]. The oil was purified by flash chromatography on silica gel using ethyl acetate as the eluent ($R_f$=0.56). This gave 0.89 g (6.85 mmol) of (8) with a purity of >99% which corresponds to 76% yield based on (α-7). $^1$H NMR (300 MHz, DMSO-$d_6$) δ 5.52 (1H, d, J=4.8 Hz), 5.14 (1H, d, J=4.5 Hz), 4.27-4.17 (1H, m), 3.84-3.74 (2H, m), 3.72-3.62 (1H, m), 3.33 (1H, dd, J=22.6, 14.1 Hz), 2.77-2.66 (1H, m), 2.24-2.14 (1H, m), 1.75-1.59 (1H, m). $^{13}$C NMR (75 MHz, DMSO-$d_6$) δ 108.8 (CH), 72.1 ($CH_2$), 69.4 (CH), 68.8 ($CH_2$), 45.8 (CH), 24.6 ($CH_2$). $^1$H NMR (300 MHz, $CDCl_3$) δ 5.62 (1H, d, J=4.9 Hz), 4.36 (1H, q, J=7.2 Hz), 3.94-3.77 (3H, m), 3.52 (1H, dd, J=8.9, 7.1 Hz), 3.20 (1H, s), 2.84-2.73 (1H, m), 2.30-2.20 (1H, m), 1.87-1.72 (1H, m). $^{13}$C NMR (75 MHz, $CDCl_3$) δ 109.3 (CH), 72.7 ($CH_2$), 70.4 (CH), 69.7 ($CH_2$), 46.3 (CH), 24.7 ($CH_2$). GC-MS: calculated for $C_6H_{11}O_3$ (M+H+) 131.0. found 131.0. e.e. >99% (as determined by GC). The e.e. determination of 8 was performed with an HP 5890 GC and a Supelco 24305 Betadex column of 60 mm and an internal diameter of 0.25 mm and with a film thickness of 0.25 μm using a column head pressure of 30 psi, a column flow of 1.4 mL/minute, a split flow of 37.5 mL/minute and an injection temperature of 250° C. The used ramp was: initial temperature 80° C. (1 minute), rate 4° C./minute, final temperature 180° C. (5 minutes). Detection was performed with an FID detector at a temperature of 250° C. The retention times were as follows: (8) 27.1 min, (3S,3aR,6aS)-hexahydro-furo[2,3-b]furan-3-ol [the enantiomer of (8)]27.3 minutes. Racemic (8) required for the e.e. determination was prepared according to the same procedure as described above for optically active (8) except that racemic (α-7) was used as the starting material.

Synthesis of Compound (9)

A solution of compound (8) (500 mg, 3.85 mmol) and N,N-disuccinimidyl (1.47 g, 5.75 mmol) in 20 mL of $CH_3CN$ was added triethyl amine (1.10 mL, 10.40 mmol). The resulting solution was stirred at room temperature for 7 hours. The reaction mixture was concentrated under reduced pressure. The resulting residue was treated with 20 mL of saturated $KHCO_3$ and then extracted with ethyl acetate (150 mL×3). The organic phase was washed with water (150 mL×3) and dried over $Na_2SO_4$. Compound (9) (827 mg, yield 79%) was obtained after removing the solvent and dried under vacuum. $^1$H NMR (300 MHz, $CDCl_3$) δ 2.00 (m, 1H). 2.15 (m, 1H), 2.87 (br., 4H), 3.14 (m, 1H), 3.96 (m, 2H), 4.03 (m, 1H), 4.12 (m, 1H) 5.28 (m, 1H), 5.76 (d, 1H).

Synthesis of Compound (11)

To a stirred solution of compound (10) (962 mg, 3.65 mmol) in 2-propanol (40 mL) at room temperature was added isobutyl amine (1.60 g, 21.92 mmol). The resulting mixture was reacted at 75° C. for six hours. After this period, the reaction mixture was concentrated under reduced pressure. The resulting residue was dissolved in 5 ml of 2-propanol and concentrated again under reduced pressure. The desired product was obtained (1.17 g, yield: 95%) as a white solid; $^1$H NMR (300 MHz, $CDCl_3$) δ 0.91 (d, 3H), 0.93 (d, 3H), 1.37 (s, 9H), 1.72 (m, 1H), 2.42 (d, 2H), 2.70 (d, 2H), 2.86 (m, 1H), 3.01 (dd, 1H), 3.48 (m, 1H), 3.84 (br., 1H), 4.74 (d, 1H), 7.20-7.33 (m, 5H); LC-MS (m/z) calcd. 336.25. found 337.25 [M+H]+.

Synthesis of Compound (12)

To a stirred solution of the amine prepared above (1.16 g, 3.48 mmol) in a mixture of $CH_2Cl_2$ (30 mL) and saturated aqueous sodium bicarbonate (20 mL) at 23° C. was added 4-nitrobenzenesulfonyl chloride (1.16 g, 5.21 mmol). The resulting mixture was stirred at room temperature for 16 hours. The mixture was then extracted with $CH_2Cl_2$ and dried over anhydrous $Na_2SO_4$. Removal of solvent under reduced pressure, followed by column chromatography over silica gel (3% EtOAc in $CH_2Cl_2$ as the eluent), yielded compound (12) (1.29 g, 72%) as a white amorphous solid: $^1$H NMR (300 MHz, $CDCl_3$) δ 0.86 (d, 3H), 0.87 (d, 3H), 1.36 (s, 9H), 1.84-1.92 (m, 1H), 2.86-2.95 (m, 2H), 2.98 (d, 2H), 3.19 (d, 2H), 3.75-3.82 (m, 2H), 4.64 (d, 1H), 7.22-7.32 (m, 5H), 7.95 (d, 2H), 8.32 (d, 2H); LC-MS (m/z) calcd., 521.22. found, 544.3 [M+Na]+.

Synthesis of Compound (13)

To a solution of compound (12) (1.28 g, 2.40 mmol) in EtOAc (20 mL) was added Pd/C (100 mg). The mixture was stirred at room temperature under an $H_2$ (15 psi) for 10 h. The reaction mixture was filtered over Celite, and the filter cake was washed with EtOAc. Removal of solvent under reduced pressure, followed by column chromatography on silica gel (7% EtOAc in $CHCl_3$ as the eluent) afforded the corresponding aromatic amine (1.16 g, 98%) as a white solid: $^1$H NMR (300 MHz, $CDCl_3$) δ 0.86 (d, 3H), 0.89 (d, 3H), 1.34 (s, 9H), 1.86 (m, 1H), 2.77 (dd, 1H), 2.89-3.15 (m, 5H), 3.85 (br., 2H), 4.05 (br., 1H), 4.17 (s, 2H), 4.65 (br., 1H), 6.71 (d, 2H), 7.19-7.30 (m, 5H), 7.58 (d, 2H); LC-MS (m/z) calcd., 491.3. found: 492.3 $[M+H]^+$, 514.23. $[M+Na]^+$.

Synthesis of Compound (16) (General Procedure for 16a, 16b and 16c)

A solution of compound (13) (98 mg, 0.20 mmol) and mPEG$_n$-CHO (n=3, 5 or 7, run separately) (0.30 mmol) in $CH_3OH$ (10 mL) was stirred at 85° C. under azeotropic conditions for 90 minutes (4.0 ml of $CH_3OH$ was removed). After this period, the reaction mixture was cooled to room temperature and sodium borohydride (20 eq.) was added in portions. The mixture was stirred at 50° C. for two hours, and then the reaction was quenched with sodium bicarbonate. 150 ml of DCM was added. The solution was washed with $H_2O$ (3×150 ml). The organic phase was dried over sodium sulfate and was then concentrated under reduced pressure. The residue was purified by column chromatography over silica gel (2% MeOH in $CHCl_3$ as the eluent) to provide compound (16a), (16b) or (16c) respectively (yield, 70-80%) as colorless oil. Compound (16a) (n=3), $^1$H NMR (300 MHz, $CDCl_3$) δ 0.86 (d, 3H), 0.89 (d, 3H), 1.33 (s, 9H), 1.82 (m, 1H), 2.77 (dd, 1H), 2.89-2.92 (m, 2H), 2.99-3.11 (m, 3H), 3.75-3.80 (m, 2H), 3.32 (m, 2H), 3.38 (s, 3H), 3.57 (m, 2H), 3.60-3.90 (m, 11H), 4.04 (br., 1H), 4.62 (d, 1H), 4.85 (t, 1H), 6.60 (d, 2H), 7.19-7.30 (m, 5H), 7.54 (d, 2H); LC-MS (m/z) calcd. 637.3. found: 638.3 $[M+H]^+$. Compound (16b) (n=5), $^1$H NMR (300 MHz, $CDCl_3$) δ 0.86 (d, 3H), 0.89 (d, 3H), 1.34 (s, 9H), 1.80-1.86 (m, 1H), 2.77 (dd, 1H), 2.89-2.92 (m, 3H), 2.99-3.11 (m, 2H), 3.32 (m, 2H), 3.36 (s, 3H), 3.54 (m, 2H), 3.58-3.90 (m, 19H), 4.65 (d, 1H), 4.98 (t, 1H), 6.59 (d, 2H), 7.19-7.30 (m, 5H), 7.54 (d, 2H). Compound (16c) (n=7), $^1$H NMR (300 MHz, $CDCl_3$) δ 0.86 (d, 3H), 0.89 (d, 3H), 1.34 (s, 9H), 1.80-1.86 (m, 1H), 2.77 (dd, 1H), 2.89-3.11 (m, 5H), 3.32 (m, 2H), 3.36 (s, 3H), 3.54 (m, 2H), 3.58-3.90 (m, 27H), 4.65 (d, 1H), 4.98 (t, 1H), 6.59 (d, 2H), 7.19-7.30 (m, 5H), 7.54 (d, 2H).

Synthesis of Compound (17) (General Procedure for 17a, 17b and 17c)

A solution of compound (17a), (17b) or (17c) (each run separately) (0.151 mmol) in a mixture of 30% trifluoroacetic acid in CH₂Cl₂ (4 mL) was stirred for 60 min. After this period, the reaction mixture was concentrated under reduced pressure and the resulting residue was redissolved in CH₂Cl₂ (5.0 mL). To this solution were added compound 9 (45 mg, 0.17 mmol) and triethylamine (0.155 mL, 1.51 mmol). The resulting mixture was stirred for 2 h. The reaction mixture was then concentrated under reduced pressure, and the residue was purified by column chromatography over silica gel (2% MeOH in CHCl₃ as the eluent) to provide compound (17a), (17b), and (17c), respectively (yield: 80-89%) as an oil. Compound (17a) (n=3), ¹H NMR (300 MHz, CDCl₃) δ 0.87 (d, 3H), 0.93 (d, 3H), 1.42-1.46 (m, 1H), 1.57-1.65 (m, 1H), 1.79-1.85 (m, 1H), 2.75-2.81 (m, 2H), 2.87-2.98 (m, 3H), 3.05-3.16 (m, 2H), 3.34 (m, 2H), 3.38 (s, 3H), 3.58 (m, 2H), 3.64-3.74 (m, 10H), 3.82-4.00 (m, 5H), 4.97-5.01 (m, 2H), 5.63 (d, 1H), 6.67 (d, 2H), 7.18-7.28 (m, 5H), 7.53 (d, 2H); LC-MS (m/z) calcd: 693.3. found 694.3 [M+H]⁺. Compound (17b) (n=5), ¹H NMR (300 MHz, CDCl₃) δ 0.87 (d, 3H), 0.93 (d, 3H), 1.46 (m, 1H), 1.60 (m, 1H), 1.82 (m, 1H), 2.75-2.81 (m, 2H), 2.87-2.98 (m, 3H), 3.05-3.16 (m, 2H), 3.32 (m, 2H), 3.36 (s, 3H), 3.54 (m, 2H), 3.64-3.74 (m, 18H), 3.82-3.92 (m, 5H), 4.97-5.01 (m, 2H), 5.63 (d, 1H), 6.67 (d, 2H), 7.18-7.28 (m, 5H), 7.54 (d, 2H); LC-MS (m/z) calcd. 781.4. found 782.5 [M+H]⁺. Compound (17c) (n=7), ¹H NMR (300 MHz, CDCl₃) δ 0.87 (d, 3H), 0.92 (d, 3H), 1.46 (m, 1H), 1.60 (m, 1H), 1.82 (m, 1H), 2.75-2.81 (m, 2H), 2.87-2.98 (m, 3H), 3.05-3.16 (m, 2H), 3.30 (m, 2H), 3.36 (s, 3H), 3.54 (m, 2H), 3.64-3.74 (m, 26H), 3.82-3.92 (m, 5H), 4.97-5.05 (m, 3H), 5.63 (d, 1H), 6.62 (d, 2H), 7.18-7.28 (m, 5H), 7.53 (d, 2H); LC-MS (m/z) calcd: 869.4. found 870.3 [M+H]⁺.

Example 6

Synthesis of PEG-Darunavir—"Approach B"

PEG-darunavir was prepared using a second approach. Schematically, the approach followed for this example is shown below (compound numbers in bold in the schematic correspond to the compound numbers provided in the text of this Example 6 alone).

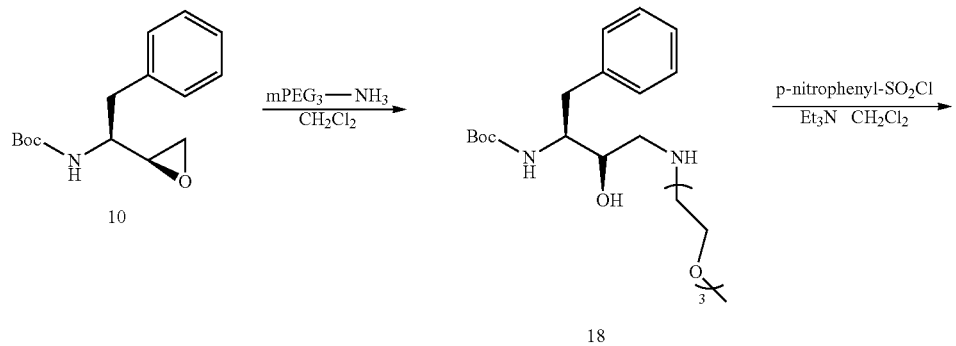

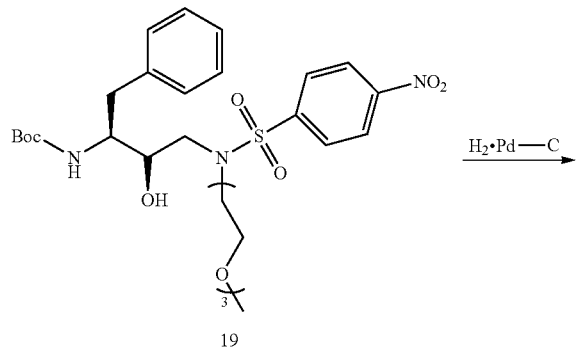

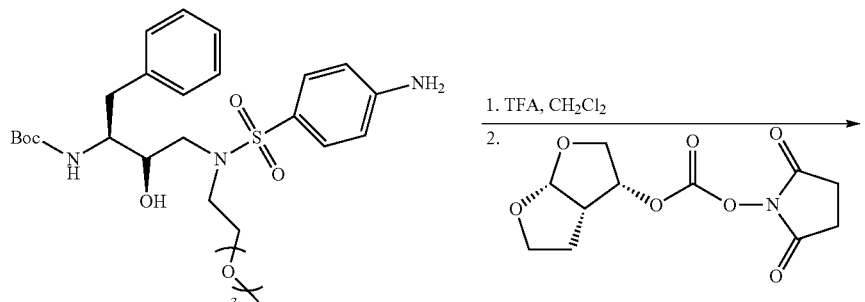

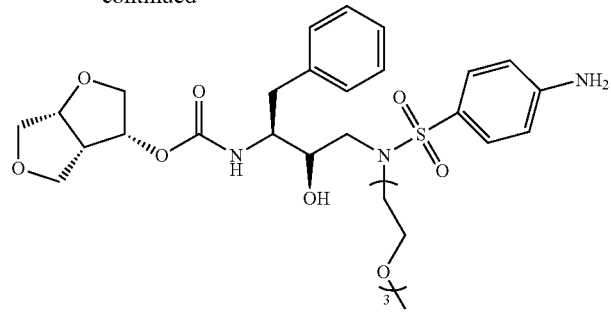

21

Synthesis of Compound (18)

To a stirred solution of compound (10) (264 mg, 1.0 mmol) [prepared in accordance with the procedure for synthesizing compound (10) in Example 12] in 2-propanol (10 mL) at 23° C. was added mPEG$_3$-NH$_2$ (489 mg, 3.0 mmol). The resulting mixture was stirred at 75° C. for six hours. After this period, the reaction mixture was concentrated under reduced pressure. The residue was purified by column chromatography on silica gel (biotage, CH$_3$OH/DCM, 4-15% CH$_3$OH, 20 CV). 390 mg of corresponding amine (18) was obtained (yield, 91.5%) as sticky oil. $^1$H NMR (300 MHz, CDCl$_3$) δ 1.35 (s, 9H), 1.85-1.89 (m, 1H), 2.70 (m, 1H), 2.86 (m, 4H), 3.00 (dd, 1H), 3.35 (s, 3H), 3.54-3.75 (m, 10H), 3.85 (m, 1H), 4.70 (d, 1H), 7.10-7.40 (m, 5H); LC-MS (m/z) calcd., 426.3. found 427.2 [M+H]$^+$.

Synthesis of Compound (19)

To a stirred solution of above prepared amine (18) (390 mg, 0.92 mmol) in a mixture of CH$_2$Cl$_2$ (15 mL) and saturated aqueous sodium bicarbonate (10 mL) at 23° C. was added 4-nitrobenzenesulfonyl chloride (304 mg, 1.38 mmol). The resulting mixture was stirred at room temperature for 16 hours. The mixture was then extracted with CH$_2$Cl$_2$ and dried over anhydrous Na$_2$SO$_4$. Removal of solvent under reduced pressure, followed by column chromatography over silica gel (biotage, DCM/CH$_3$OH, CH$_3$OH: 1-6%, 20 CV) gave the desired product (19) (455 mg, 81%) as sticky oil: $^1$H NMR (300 MHz, CDCl$_3$) δ 1.37 (s, 9H), 2.85 (m, 1H), 3.10 (m, 2H), 3.30 (m, 1H), 3.41 (m, 2H), 3.38 (s, 3H), 3.50-3.85 (m, 11H), 3.90 (m, 1H), 4.45 (d, 1H), 4.95 (d, 1H), 7.22-7.32 (m, 5H), 7.95 (d, 2H), 8.32 (d, 2H). LC-MS (m/z) calcd., 611.3. found, 612.3 [M+H]$^+$.

Synthesis of Compound (20)

To a solution of compound (19) (455 mg, 0.74 mmol) in EtOAc (10 mL) was added Pd/C (40 mg, 10%). The mixture was stirred at room temperature under an H$_2$ atmosphere (30 psi) for 4.0 hours. The reaction mixture was filtered over Celite, and the filter cake was washed with EtOAc. Removal of solvent under reduced pressure afforded the corresponding aromatic amine (420 mg, 98%) as a white solid: $^1$H NMR (300 MHz, CDCl$_3$) δ 1.36 (s, 9H), 2.90-3.10 (m, 3H), 3.10-3.30 (m, 3H), 3.37 (s, 3H), 3.56 (m, 2H), 3.63-3.90 (m, 11H), 4.54 (br., 1H), 4.88 (d, 1H), 6.65 (d, 2H), 7.19-7.30 (m, 5H), 7.53 (d, 2H); LC-MS (m/z), calcd., 581.3. found: 582.3 [M+H]$^+$.

Synthesis of Compound (21)

A solution of compound (20) (116 mg, 0.2 mmol) in a mixture of 30% trifluoroacetic acid in CH$_2$Cl$_2$ (4 mL) was stirred at room temperature for 1.0 hour. After this period, the reaction mixture was concentrated under reduced pressure and the residue was redissolved in CH$_2$Cl$_2$ (5.0 mL). To this solution were added (3R,3aS,6aR)-3 hydroxyhexahydrofuro[2,3-b]furanyl succinimidyl carbonate [compound (9)](54 mg, 0.2 mmol) and triethylamine (0.5 mL). The resulting mixture was stirred for two hours. At which point, the solution was concentrated under reduced pressure. The resulting residue was purified by column chromatography (biotage, DCM/CH$_3$OH, CH$_3$OH: 2-6%, 20 CV) to provide compound (21) (102 mg, 80%) as a oil. $^1$H NMR (300 MHz, CDCl$_3$) δ 1.40-1.60 (m, 1H), 1.60-1.80 (m, 1H), 1.90 (br., 1H), 2.75 (m, 1H), 2.90 (m, 1H), 3.00-3.15 (m, 2H), 3.15-3.30 (m, 3H), 3.37 (s, 3H), 3.50-3.85 (m, 12H), 3.85-3.98 (m, 4H), 4.23 (br., 2H), 4.50 (br., 1H), 5.02 (m, 1H), 5.40 (d, 1H), 5.64 (d, 1H), 6.67 (d, 2H, J) 8.6 Hz), 7.18-7.28 (m, 5H), 7.51 (d, 2H); LC-MS (m/z), calcd., 637.2. found, 638.2 [M+H]$^+$.

Example 7

Synthesis of PEG-Darunavir—"Approach C"

PEG-darunavir was prepared using a third approach. Schematically, the approach followed for this example is shown below (compound numbers in bold in the schematic correspond to the compound numbers provided in the text of this Example 7 alone).

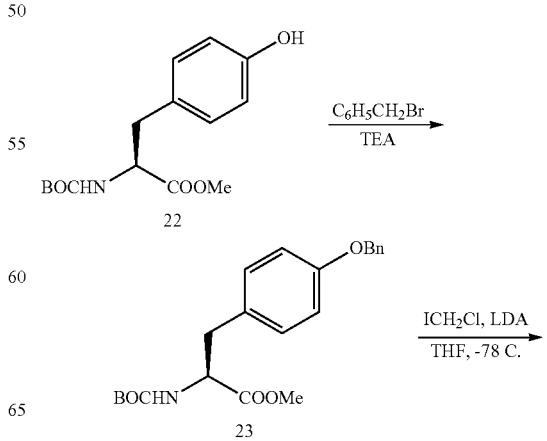

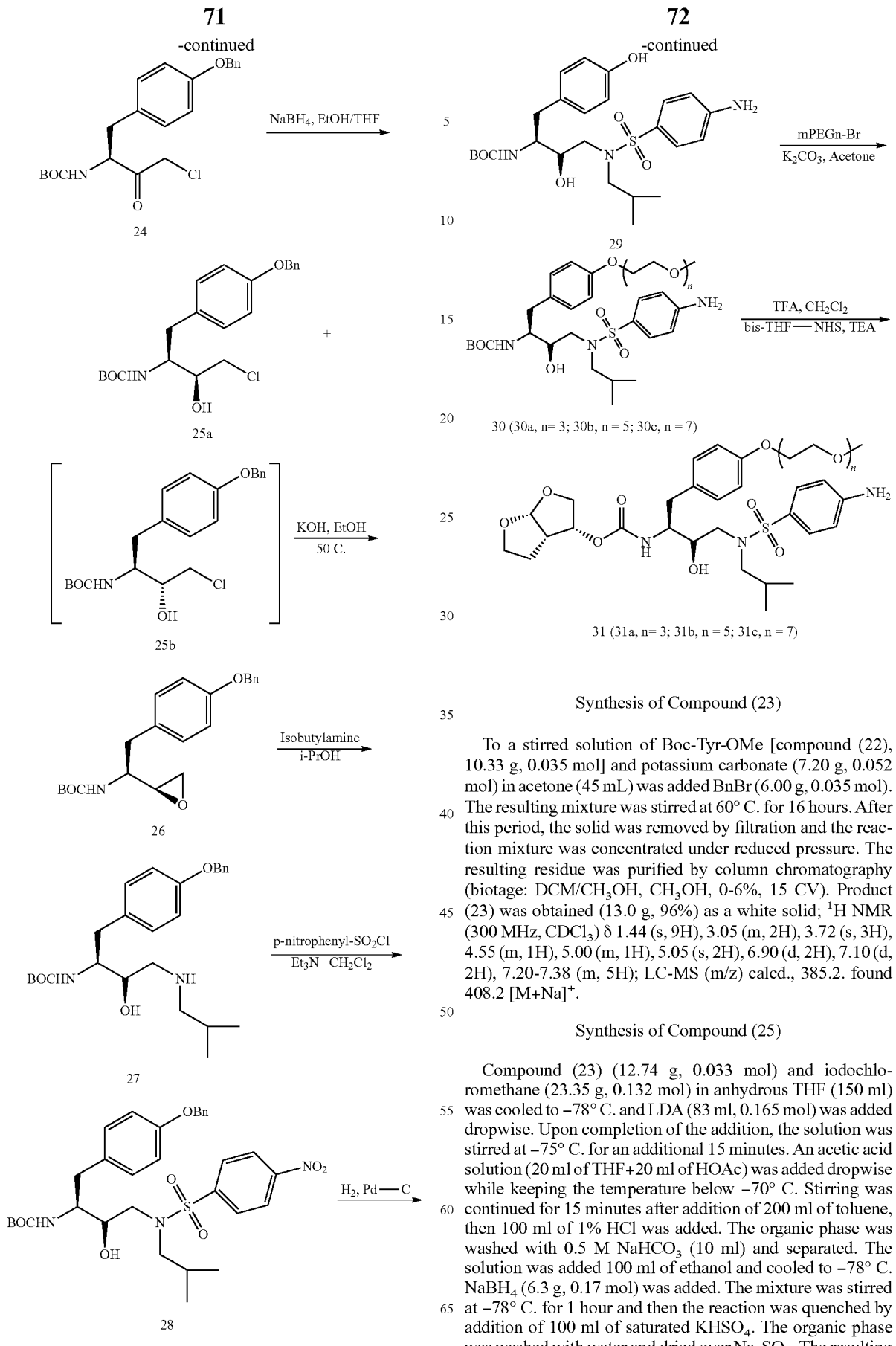

Synthesis of Compound (23)

To a stirred solution of Boc-Tyr-OMe [compound (22), 10.33 g, 0.035 mol] and potassium carbonate (7.20 g, 0.052 mol) in acetone (45 mL) was added BnBr (6.00 g, 0.035 mol). The resulting mixture was stirred at 60° C. for 16 hours. After this period, the solid was removed by filtration and the reaction mixture was concentrated under reduced pressure. The resulting residue was purified by column chromatography (biotage: DCM/CH$_3$OH, CH$_3$OH, 0-6%, 15 CV). Product (23) was obtained (13.0 g, 96%) as a white solid; $^1$H NMR (300 MHz, CDCl$_3$) δ 1.44 (s, 9H), 3.05 (m, 2H), 3.72 (s, 3H), 4.55 (m, 1H), 5.00 (m, 1H), 5.05 (s, 2H), 6.90 (d, 2H), 7.10 (d, 2H), 7.20-7.38 (m, 5H); LC-MS (m/z) calcd., 385.2. found 408.2 [M+Na]$^+$.

Synthesis of Compound (25)

Compound (23) (12.74 g, 0.033 mol) and iodochloromethane (23.35 g, 0.132 mol) in anhydrous THF (150 ml) was cooled to −78° C. and LDA (83 ml, 0.165 mol) was added dropwise. Upon completion of the addition, the solution was stirred at −75° C. for an additional 15 minutes. An acetic acid solution (20 ml of THF+20 ml of HOAc) was added dropwise while keeping the temperature below −70° C. Stirring was continued for 15 minutes after addition of 200 ml of toluene, then 100 ml of 1% HCl was added. The organic phase was washed with 0.5 M NaHCO$_3$ (10 ml) and separated. The solution was added 100 ml of ethanol and cooled to −78° C. NaBH$_4$ (6.3 g, 0.17 mol) was added. The mixture was stirred at −78° C. for 1 hour and then the reaction was quenched by addition of 100 ml of saturated KHSO$_4$. The organic phase was washed with water and dried over Na$_2$SO$_4$. The resulting solid, after solvent removal, was washed with hexane and then recrystallized from ethyl acetate. Compound (25a) [3.5 g, 30% based on compound (23)] was obtained as yellow solid. $^1$H NMR (300 MHz, CDCl$_3$) δ 1.39 (s, 9H), 2.91 (m, 2H), 3.17 (br., 1H), 3.57 (m, 1H), 3.67 (m, 1H), 3.84 (m, 2H), 4.57 (m, 1H), 5.05 (s, 2H), 6.92 (d, 2H), 7.13 (d, 2H), 7.20-7.38 (m, 5H); LC-MS (m/z) calcd., 405.2. found 428.2 [M+Na]+.

Synthesis of Compound (26)

Compound (25a) (2.18 g, 5.38 mmol) was suspended in a 0.1 N solution of potassium hydroxide in methanol (5.92 mmol, 59.2 ml). The resulting mixture was stirred at 50° C. for 1.5 hours. The solvent was removed under reduced pressure and the solid was dissolved in 100 ml DCM, which was subsequently washed with water (100 mL×3). The solution was dried and solvent was removed under reduced pressure. The desired product was obtained as a yellow solid (1.74 g, 88%) was obtained. $^1$H NMR (300 MHz, CDCl$_3$) δ 1.40 (s, 9H), 2.77 (m, 3H), 2.92 (m, 2H), 3.65 (br., 1H), 4.44 (br., 1H), 5.05 (s, 2H), 6.92 (d, 2H), 7.15 (d, 2H), 7.26-7.38 (m, 5H); LC-MS (m/z) calcd., 369.2. found, 370.2 [M+H]+, 392.2 [M+Na]$^+$.

Synthesis of Compounds (27) & (28)

To a stirred solution of compound (26) (1.74 g, 4.80 mmol) in 2-propanol (60 mL) at 23° C. was added isobutyl amine (2.20 g, 30 mmol). The resulting mixture was reacted at 75° C. for 6 hours. After this period, the reaction mixture was concentrated under reduced pressure. The residue was dissolved in 5 ml of 2-propanol and concentrated again under reduced pressure. Compound (27) was obtained (1.97 g) as a yellow solid, which was used in next reaction without further purification.

To a stirred solution of compound (27) (1.97 g, 4.45 mmol) in a mixture of CH$_2$Cl$_2$ (40 mL) and saturated aqueous sodium bicarbonate (30 mL) at 23° C. was added 4-nitrobenzenesulfonyl chloride (1.48 g, 6.67 mmol). The resulting mixture was stirred at room temperature for 16 hours. The mixture was then extracted with CH$_2$Cl$_2$ (150 mL×2). The organic phase was washed with water (150 mL×3) and dried over anhydrous Na$_2$SO$_4$. Removal of solvent under reduced pressure, followed by column chromatography (biotage: DCM/CH$_3$OH, CH$_3$OH, 1-6%, 15CV, 6-8% 5CV), yielded compound (28) (2.14 g, 77%) as a white amorphous solid: $^1$H NMR (500 MHz, CDCl$_3$) δ 0.87 (d, 3H), 0.89 (d, 3H), 1.37 (s, 9H), 1.87 (m, 1H), 2.86 (m, 2H), 2.99 (d, 2H), 3.19 (d, 2H), 3.72 (m, 1H), 3.79 (m, 2H), 4.61 (d, 1H), 5.05 (s, 2H), 6.90 (d, 2H), 7.14 (d, 2H), 7.35 (m, 1H), 7.44 (m, 4H), 7.95 (d, 2H), 8.34 (d, 2H); LC-MS (m/z) calcd., 627.26. found, 650.3 [M+Na]$^+$.

Synthesis of Compound (29)

To a solution of compound (28) (2.14 g, 3.41 mmol) in THF (20 mL) was added Pd/C (428 mg). The mixture was stirred at room temperature under an H$_2$ atmosphere (45 psi) for 48.0 hours. The reaction mixture was filtered over Celite, and the filter cake was washed with THF. Removal of the solvent under reduced pressure afforded the corresponding aromatic amine (1.48 g, 86%) as a white solid: $^1$H NMR (500 MHz, CDCl$_3$) δ 0.86 (d, 3H), 0.90 (d, 3H), 1.36 (s, 9H), 1.85 (m, 1H), 2.77 (m, 1H), 2.84 (m, 1H), 2.90 (m, 2H), 2.92 (d, 1H), 3.07 (m, 1H), 3.71 (m, 1H), 3.77 (m, 1H), 4.16 (br., 2H), 4.72 (d, 1H), 6.66 (d, 2H), 6.75 (d, 2H), 7.09 (d, 2H), 7.52 (d, 2H).

General Procedure for the Synthesis of Compounds (30a), (30b) and (30c)

A solution of compound (29) (152 mg, 0.30 mmol) and mPEG$_n$-Br (n=3, 5 and 7, in three separate runs) (0.45 mmol) in acetone (10 mL) was stirred at 70° C. for 20 hours. After this period, the reaction mixture was cooled to room temperature and 150 mL of DCM was added. The solution was washed with water (150 mL×2). The organic phase was dried over sodium sulfate and then concentrated under reduced pressure. The resulting residue was purified by column chromatography (biotage: DCM/CH$_3$OH, CH$_3$OH, 3-6%, 15CV, 6-8% 5CV) to provide compound (30a), (30b) and (30c), respectively (yield, 70-80%) as colorless oil. Compound (30a) (n=3): $^1$H NMR (500 MHz, CDCl$_3$) δ 0.83 (d, 3H), 0.89 (d, 3H), 1.36 (s, 9H), 1.82 (m, 1H), 2.62 (m, 1H), 2.69 (m, 1H), 2.86 (m, 1H), 2.92 (m, 3H), 3.36 (s, 3H), 3.53 (m, 2H), 3.62 (m, 2H), 3.68 (m, 2H), 3.74 (m, 4H), 3.85 (m, 3H), 4.08 (m, 2H), 4.40 (br., 2H), 4.77 (d, 1H), 6.62 (d, 2H), 6.82 (d, 2H), 7.14 (d, 2H), 7.38 (d, 2H); LC-MS (m/z) calcd., 653.3. found, 654.4 [M+H]$^+$. Compound (30b) (n=5): $^1$H NMR (500 MHz, CDCl$_3$) δ 0.83 (d, 3H), 0.89 (d, 3H), 1.37 (s, 9H), 1.81 (m, 1H), 2.60 (m, 2H), 2.85 (m, 1H), 2.92 (m, 3H), 3.35 (s, 3H), 3.52 (m, 2H), 3.61-3.65 (m, 11H), 3.70 (m, 2H), 3.75 (m, 5H), 3.85 (m, 2H), 4.07 (m, 2H), 4.49 (br., 2H), 4.73 (d, 1H), 6.62 (d, 2H), 6.82 (d, 2H), 7.15 (d, 2H), 7.34 (d, 2H); LC-MS (m/z) calcd., 741.4. found, 742.5 [M+H]+, 764.4. [M+Na]$^+$. Compound (30c) (n=7): $^1$H NMR (500 MHz, CDCl$_3$) δ 0.82 (d, 3H), 0.89 (d, 3H), 1.36 (s, 9H), 1.80 (m, 1H), 2.85 (m, 1H), 2.92 (m, 3H), 3.35 (s, 3H), 3.52 (m, 2H), 3.61-3.65 (m, 19H), 3.70 (m, 2H), 3.75 (m, 5H), 3.85 (m, 2H), 4.07 (m, 2H), 4.49 (s, 2H), 4.73 (d, 1H), 6.61 (d, 2H), 6.82 (d, 2H), 7.14 (d, 2H), 7.35 (d, 2H); LC-MS (m/z) calcd., 829.4. found, 830.5 [M+H]+.

General Procedure for the Synthesis of Compounds (31a), (31b) and (31c)

A solution of compound (30a), (30b) and (30c) (0.20 mmol, in three separate runs) in a mixture of 30% trifluoroacetic acid in CH$_2$Cl$_2$ (4.0 mL) was stirred at room temperature for 40 minutes. After this period, the reaction mixture was concentrated under reduced pressure and the residue was redissolved in CH$_2$Cl$_2$ (5.0 mL). To this solution were added (3R,3aS,6aR)-3 hydroxyhexahydrofuro[2,3-b]furanyl succinimidyl carbonate (54 mg, 0.20 mmol) and triethylamine (0.155 mL, 1.51 mmol). The resulting mixture was stirred for one hour. The reaction mixture was then concentrated under reduced pressure, and the residue was purified by column chromatography (biotage, DCM/CH$_3$OH, CH$_3$OH: 0-4%, 20 CV, 4-6%, 10 CV) to provide compounds (31a), (31b), and (31c), respectively (yield: 75-80%) as colorless oil. Compound (31a) (n=3): $^1$H NMR (500 MHz, CDCl$_3$) δ 0.83 (d, 3H), 0.88 (d, 3H), 1.58 (m, 1H), 1.64 (m, 1H), 1.77 (m, 1H), 2.65 (m, 1H), 2.72 (m, 2H), 2.90 (m, 2H), 2.98 (m, 2H), 3.35 (s, 3H), 3.52 (m, 2H), 3.60 (m, 2H), 3.64 (m, 3H), 3.69 (m, 4H), 3.81 (m, 5H), 3.92 (m, 1H), 4.03 (m, 2H), 4.46 (s, 2H), 5.00 (m, 1H), 5.16 (d, 1H), 5.62 (d, 1H), 6.60 (d, 2H), 6.78 (d, 2H), 7.08 (d, 2H), 7.38 (d, 2H); LC-MS (m/z) calcd: 709.3. found 710.3 [M+H]$^+$. Compound (31b) (n=5): $^1$H NMR (500 MHz, CDCl$_3$) δ 0.86 (d, 3H), 0.92 (d, 3H), 1.71-1.85 (m, 3H), 2.65 (m, 2H), 2.78 (m, 1H), 2.97 (m, 4H), 3.36 (s, 3H), 3.54 (m, 2H), 3.64 (m, 10H), 3.68 (m, 3H), 3.75 (m, 4H), 3.69 (m, 4H), 3.85 (m, 4H), 3.90 (m, 1H), 4.00 (m, 1H), 4.10 (m, 2H), 4.50 (br., 2H), 5.06 (m, 1H), 5.12 (d, 1H), 5.66 (d, 1H), 6.64 (d, 2H), 6.82 (d, 2H), 7.13 (d, 2H), 7.37 (d, 2H); LC-MS (m/z) calcd: 797.4. found 798.4 [M+H]$^+$. Compound (31c) (n=7), $^1$H NMR (500 MHz, CDCl$_3$) δ 0.86 (d, 3H), 0.92 (d, 3H), 1.71-1.85 (m, 3H), 2.62 (m, 2H), 2.78 (m, 1H), 2.97 (m, 4H), 3.37 (s, 3H), 3.54 (m, 2H), 3.64 (m, 19H), 3.68 (m, 3H), 3.73 (m, 4H), 3.85 (m, 4H), 3.90 (m, 1H), 4.00 (m, 1H), 4.08 (m, 2H), 4.52 (br., 2H), 5.06 (m, 1H), 5.12 (d, 1H), 5.66 (d, 1H), 6.64 (d, 2H), 6.82 (d, 2H), 7.13 (d, 2H), 7.37 (d, 2H); LC-MS (m/z) calcd: 885.4. found 886.5 [M+H]$^+$.

Example 8

Synthesis of PEG-Tipranavir

PEG-tipranavir was prepared. Schematically, the approach followed for this example is shown below (wherein Xa stands for oxazolidinone and compound numbers in bold in the schematic correspond to the compound numbers provided in the text of this Example 8 alone).

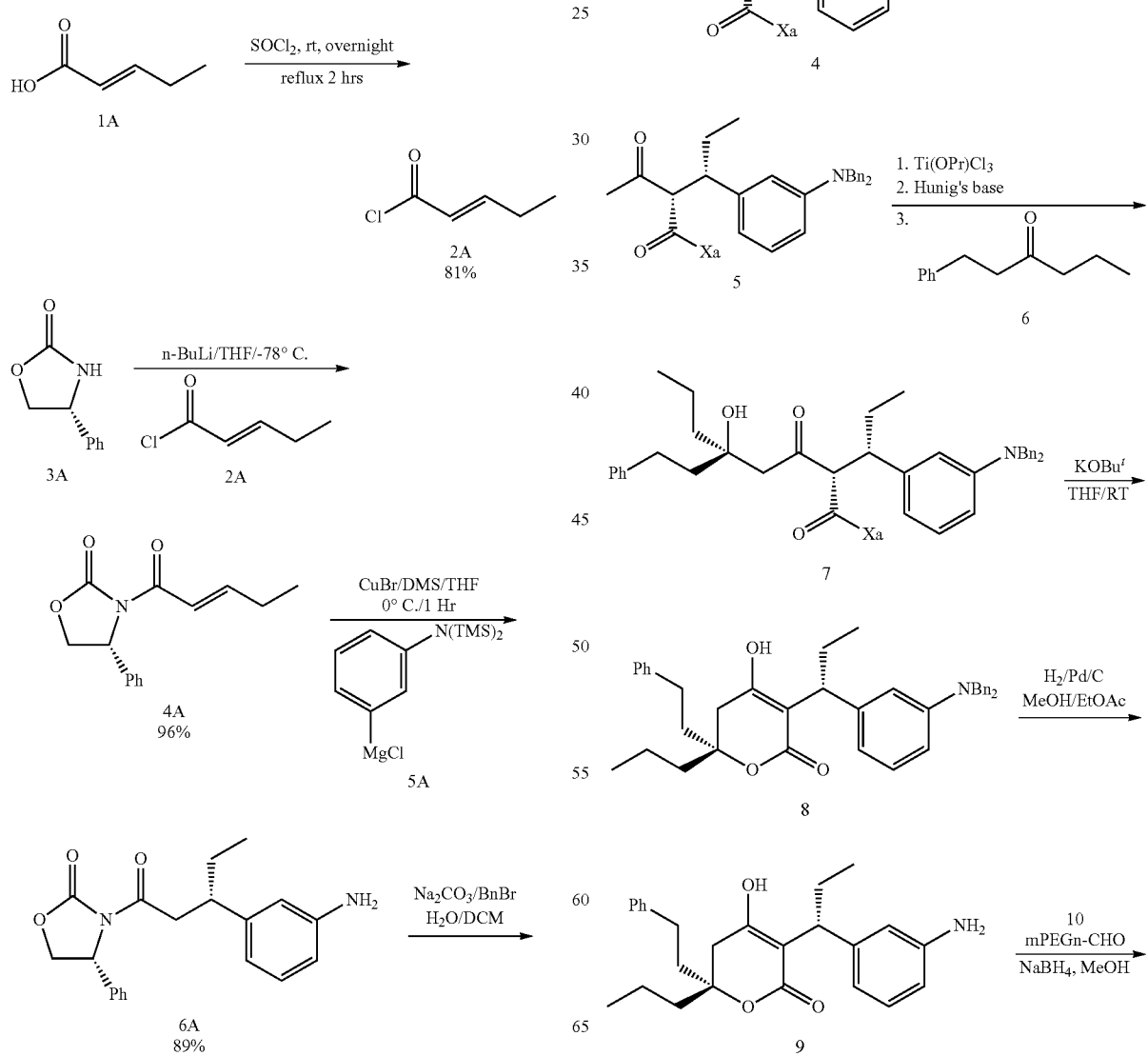

-continued

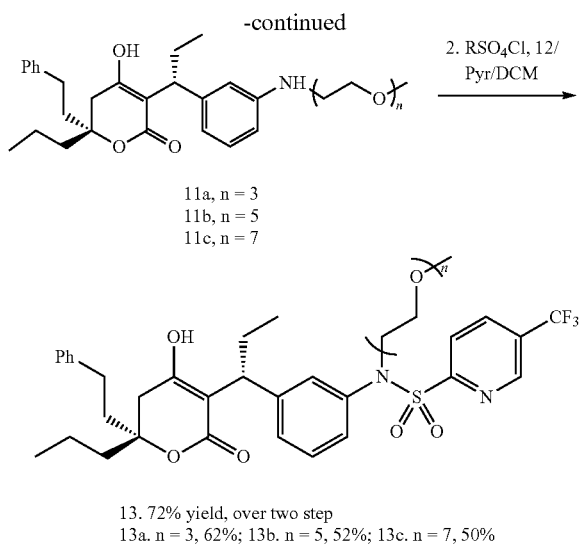

11a, n = 3
11b, n = 5
11c, n = 7

13. 72% yield, over two step
13a. n = 3, 62%; 13b. n = 5, 52%; 13c. n = 7, 50%

In carrying out this synthesis, the following materials were used. Calcium hydride (CaH$_2$), ethylene glycol, trimethyl orthoacetate, sodium hydroxide, titanium (IV) chloride, N,N-diisopropylethylamine (DIPEA), perchlorid acid 60% (HCLO$_4$), phenethylmagnesium chloride (1.0 M in THF), butyaldehyde, pyridinium chlorochromate (PCC), titanium (IV) isopropoxide, potassium tert-butoxide (KOBut), palladium/carbon (10 wt %), oxalyl chloride [(COCl)$_2$], dimethylsulfoxide (DMSO), anhydrous methanol, sodium bronohydride (NaBH$_4$), and pyridine were purchased from Sigma-Aldrich (St Louis, Mo.). mPEG$_n$-OH (n=3, 5, 7) were purchased from TCI America. 5-Trifluoromethyl-2-pyridinesulfonyl chloride was purchased from Toronto Research Chemicals, Inc. (North York, ON, Canada). DCM was distilled from CaH$_2$. Tetrahydrofuran (THF) and other organic solvents were used as they purchased. 2-(E)-pentenoic acid, thionyl chloride, (R)-(−)-4-phenyl-2-oxazolidinone, n-butyl lithium (1M, Hexane), 3-bis(trimethylsilyl)amino]phenylmagnesium chloride (1.0 M, THF), copper bromide (I)-dimethyl sulfide, benzyl bromide, and ammonium chloride were purchased from Sigma-Aldrich (St Louis, Mo.). Ammonium hydroxide, sodium sulfate, ethyl acetate, and hexane were purchased from Fisher Scientific (Fair Lawn, N.J.). Magnesium sulfate, sodium bicarbonate, and sodium carbonate were purchased from EM Science (Gibbstown, N.J.). DCM was distilled from CaH$_2$. THF (anhydrous) and acetonitrile were also purchased from Sigma-Aldrich and used as purchased.

Acid Chloride Preparation (2A)

In a 100-mL flask equipped with a reflux condenser, 2-(E)-pentenoic acid (15.4 mL, 152 mmol) was added under N$_2$. After the reaction flask was set up in a water bath, thionyl chloride (10.5 mL, 144 mmol) was then added slowly and the reaction was kept in the water bath for an additional ten minutes before it was removed and allowed to warm to room temperature. The reaction was kept at room temperature overnight and then heated to 110° C. (external) in oil bath for 30 minutes and was kept at this temperature for an additional 30 minutes. The solution was cool down below 40° C. before vacuum distillation was started. Vacuum distillation provided desired product 2 (13.8 g, 81% yield) as a colorless liquid, under 45-55° C. (external)/8 mmHg. $^1$H NMR (300 MHz, CDCl$_3$) δ 1.13 (t, 3H, J=7.5 Hz), 2.29-2.39 (m, 2H), 6.07 (dt, 1H, J=1.5, 15.3 Hz), 7.28 (dt, 1H, J=6.3, 15.3 Hz).

Oxazolidinone Amide Bond Formation (4A)

Oxazolidinone (3A) (6.90 g, 42.3 mmol) was added to a 500-mL flask protected with N$_2$ and was filled with anhydrous THF (265 mL). The THF solution was cooled down to −78° C. in a dry-ice bath. Then n-BuLi (1.6 M in hexane, 27.8 mL, 44.4 mmol) was added slowly (about 12 minutes). The reaction was kept at this temperature for 30 minutes before 2-(E)-pentenoic acid chloride (2A) (5.51 g, 46.5 mmol) was added slowly over seven minutes. The dry-ice bath was immediately removed after addition of the acid chloride was completed and the reaction solution was warmed to room temperature over 40 minutes. The reaction then was quenched by a saturated solution of NH$_4$Cl (400 mL). A small amount of pure de-ionized water was added to dissolve the precipitation of NH$_4$Cl. The organic THF phase was separated and the aqueous phase was extracted with EtOAc (100 mL×2). The organic phases were combined, dried over MgSO$_4$, and concentrated to about 25 mL. While stirring, hexane (200 mL) was added and the crude product precipitated in a few minutes. After filtration, the solution was concentrated to about 10 mL and precipitated a second time with hexane (about 180 mL). The mother liquor was concentrated and the resulting residue was purified on Biotage (EtOAc/Hex 6-50% in 20 CV). Three portions of colorless product (4A) were combined (9.95 g, 96% yield). R$_f$=0.45 (Hex:EtOAc=3:1), RP-HPLC (betasil C18, 0.5 mL/min, 60-100% ACN in 8 min) 7.40 min, LC-MS (ESI, MH$^+$) 246.1. $^1$H NMR (300 MHz, CDCl$_3$) δ 1.08 (t, 3H, J=7.5 Hz), 2.28 (p, 2H, J=6.3 Hz), 4.28 (dd, 1H, J=3.9, 9.0 Hz), 4.70 (t, 1H, J=8.7 Hz), 5.49 (dd, 1H, J=3.9, 8.7 Hz), 7.09-7.18 (m, 1H), 7.23-7.42 (m, 6H).

Asymmetric Michael Addition:

In a 500-mL flask protected with N$_2$, copper bromide (I)-dimethyl sulfide (7.44 g, 36.2 mmol) was added followed by anhydrous THF (75 mL). The solution was cooled down to −45° C. with dry-ice/acetonitrile before 3-[bis(trimethylsilyl)amino]-phenylmagnesium chloride (1.0 M, 36.2 mL, 36.2 mmol) was added dropwise over 30 minutes. The reaction was kept at a temperature between −40° C. to 0° C. for 20 minutes. A solution of above starting material (4A) (7.1 g, 29.0 mmol) in THF (19.3 mL) was added dropwise over 20 minutes. The reaction then was warmed to 0° C. over 10 min and then further to room temperature over 15 minutes. The reaction mixture was quenched with the addition of aqueous NH$_4$Cl (70 mL) at room temperature for 15 minutes. The aqueous phase was then adjusted to pH=8 by addition of NH$_4$OH (5 mL). The solution was then poured into an ether solution (250 mL) and the aqueous phase was separated. The ether phase was washed with NaHCO$_3$ (80 mL×2) until the aqueous phase was not blue to pH paper anymore. The ether phase was then dried over Na$_2$SO$_4$ and concentrated in vacuo. The resulting residue was loaded on the reverse phase column (40 M×3, about 8 g crude each) and purified via 20-70% ACN in 20 CV. Fractions were collected and acetonitrile was evaporated. The aqueous phase then extracted with DCM (50 mL×3). The organic solution was combined, dried over Na$_2$SO$_4$, concentrated to give product (6A) (8.73 g, 89% yield). R$_f$=0.11 (Hex:EtOAc=3:1), RP-HPLC (betasil C18, 0.5 mL/min, 60-100% ACN in 8 min) 5.67 min, LC-MS (ESI, MH$^+$) 339.2. $^1$H NMR (500 MHz, CDCl$_3$) δ 0.76 (t, 3H, J=7.2 Hz), 1.50-1.68 (m, 2H), 2.90-3.00 (m, 1H), 3.06 (dd, 1H, J=7.2, 15.6 Hz), 3.48 (dd, 1H, J=7.5, 15.6 Hz), 4.17 (dd, 1H, J=4.2, 9.3 Hz), 4.64 (t, 1H, J=9.0 Hz), 5.38 (dd, 1H, J=3.9, 8.7 Hz), 6.51-6.61 (m, 3H), 6.99-7.07 (m, 3H), 7.22-7.28 (m, 3H).

Benzyl Protection of Amine:

The above product (6A) (13.5 g, 40 mmol) was dissolved in DCM (146 mL) and $H_2O$ (106 mL) in a 500-mL flask. Solid sodium carbonate (25 g, 240 mmol) and benzyl bromide (19.0 mL, 160 mmol) were added. The solution was heated (52° C. external) to reflux overnight (20 hrs) before it was checked by TLC. The reaction was diluted with $NaHCO_3$ (300 mL) and DCM was separated from the solution. The aqueous phase was then extracted with DCM (60 mL×2) and organic phases were combined. The solution was dried over $Na_2SO_4$ and concentrated. The residue was loaded on Biotage (40 M×2, 14 g crude each) over 6-22% EtOAc/Hex in 18 CV. The product fractions were collected and evaporated to generate a colorless soft solid product (2) (17.5 g, 84%). $R_f$=0.42 (Hex:EtOAc=3:1), RP-HPLC (betasil C18, 0.5 mL/min, 60-100% ACN in 8 min, 100% 8-12 min) 9.80 min, LC-MS (ESI, MH$^+$) 519.2. $^1$H NMR (300 MHz, CDCl$_3$) δ 0.65 (t, 3H, J=7.2 Hz), 1.40-1.55 (m, 2H), 2.84-2.94 (m, 1H), 3.02 (dd, 1H, J=7.2, 15.6 Hz), 3.42 (dd, 1H, J=7.5, 15.6 Hz), 4.15 (dd, 1H, J=3.9, 8.7 Hz), 4.53-4.67 (m, 5H), 5.35 (dd, 1H, J=3.9, 8.7 Hz), 6.50-6.61 (m, 3H), 6.98-7.07 (m, 3H), 7.18-7.29 (m, 13H).

Synthesis of Glycol Ortho Ester, Compound (3)

A fresh $CaH_2$ distilled starting material (26.3 g, 219 mmol) was mixed with ethylene glycol (11 mL, 197 mmol) at room temperature. $H_2SO_4$ (3-4 drops, 0.25%) was added and stirring at this temperature. A water spray vacuo system with a solid NaOH dry bottle and a mercury manometer was set up to the distillation reaction system. The vacuo was adjusted below 95 mmHg (not less than 55 mmHg) and the temperature was gradually increased (10° C. per ten minutes). After a forerun (~2 g) was collected, a colorless product (16.2 g, 70% yield) was collected under 68-71° C./58-60 mmHg. $^1$H NMR (300 MHz, CDCl$_3$) δ 1.55 (3H, s), 3.28 (3H, s), 3.97-4.12 (4H, m).

TiCl$_4$ Activated C—C Conjugation to Prepare Compound (4)

A pre-vacuo dried starting material (2) (6.45 g, 12.4 mmol) was dissolved in DCM (50 mL) under the protection of $N_2$. It was then allowed to cool down to −78° C. in a dry-ice/acetone bath. TiCl$_4$ (2.45 mL, 22.3 mmol) was dropwise added and the reaction at this temperature was kept for five minutes before DIPEA (4.11 mL, 23.6 mmol) was added. The bath was moved away immediately and the reaction was warm up to 0° C. in salt-ice bath. The enolate formation was kept at this temperature for 30 minutes before it was re-cooled down to −78° C. Glycol ortho ester (3) (3.66 mL, 31 mmol) was added slowly. After addition, the reaction was warm up to 0° C. and kept at this temperature for 2.5 hours. The reaction was quenched with half saturated NH$_4$Cl and water. The solution was diluted with water and extracted with DCM (50 mL×3). The combined organic phase was washed with NaHCO$_3$ and dried over Na$_2$SO$_4$. TLC show the reaction was clean but ~10% starting material remaining. Biotage purification (40 M×5 times) provided a colorless product (5.47 g, 73% yield) product without contamination. $R_f$=0.51 (Hex:EtOAc=3:1), LC-MS (ESI, MH$^+$) 605.3. $^1$H NMR (300 MHz, CDCl$_3$) δ 0.55 (3H, t, J=7.2 Hz), 0.86 (3H, s), 1.40-1.51 (2H, m) 2.89 (1H, dt, J=3.6, 11.1 Hz), 3.03 (1H, q, J=6.9 Hz), 3.44-3.50 (1H, m), 3.54 (1H, q, J=6.9 Hz), 3.62-3.72 (1H, m), 4.26 (1H, dd, J=3.6, 9.0 Hz), 4.55-4.67 (5H, m), 4.80 (1H, d, J=10.8 Hz), 5.46 (1H, dd, J=3.3, 8.4 Hz), 6.59-6.63 (3H, m), 7.08 (1H, t, J=7.5 Hz), 7.19-7.37 (15H, m).

Acid Hydrolysis of Acetal to Form Compound (5)

The acetal product (4) (5.47 g, 9.06 mmol) was dissolved in anhydrous THF (18 mL). Deionized water (3.6 mL) and HClO$_4$ (3.6 mL) were added. The reaction was started in an oil bath at the temperature of 40° C. (external) for 2.5 hours. After cooling down to room temperature, the solution was neutralized with NaHCO$_3$ slowly to pH=8-9. The mixture solution was diluted with water (100 mL) and extracted with DCM (80 mL×3). The organic phase was dried over Na$_2$SO$_4$ and concentrated in vacuo. The residue was loaded on Biotage column (25M) with gradient elute (4-13% EtOAc/Hex in 16 CV). A colorless solid (5.18 g, >100% yield) was collected after high vacuo drying. $R_f$=0.43 (Hex:EtOAc=3:1), RP-HPLC (betasil C18, 0.5 mL/min, 60-100% ACN in 10 min) 6.40 min, LC-MS (ESI, MH$^+$) 561.3. $^1$H NMR (300 MHz, CDCl$_3$) δ 0.61 (3H, t, J=7.2 Hz), 1.63 (3H, s), 1.07 (1H, dt, J=3.3, 10.8 Hz), 4.22 (1H, dd, J=3.9, 8.7 Hz), 4.61 (4H, s), 4.67 (1H, t, J=9.0 Hz), 4.98 (1H, d, J=10.5 Hz), 5.42 (1H, dd, J=3.6, 8.7 Hz), 6.54-6.64 (3H, m), 7.09 (1H, t, J=8.1 Hz), 7.21-7.39 (15H, m).

Synthesis of Compound (6)

Phenyl ethyl magnesium chloride (1M in THF, 120 mmol) was cannulated to a 500-mL flask together with THF (180 mL). The above mixture solution was then cool down to 0° C. using an ice-water bath before butyraldehyde (10.2 mL, 114 mmol) was added dropwise. TLC indicated a clean reaction after one hour at this temperature. The reaction was then quenched with NH$_4$Cl (150 mL) and the THF was separated. The THF solution was washed with saturated brine before it was dried over Na$_2$SO$_4$ and concentrated in vacuo. Over 20 grams of the secondary alcohol product (>100% yield) was obtained without further purification.

The secondary alcohol product (4.56 g, 25.6 mmol) was mixed with DCM (128 mL) at room temperature. PCC (6.62 g, 30.7 mmol) was added. The reaction was kept at room temperature for two hours. Due to the TLC indicated an about 15% of remaining starting material, another part of PCC (1.11 g, 5.1 mmol) was added and the reaction was finished in two hours. The solution mixture was filtrated though a layer of celite and silica gel. The filtrated solution was then evaporated and the residue was purified on Biotage column (40S). A colorless compound (6) (2.79 g, yield 62%) was collected. NMR proton spectrum indicated a product with impurity <1%. $^1$H NMR (300 MHz, CDCl$_3$) δ 0.89 (3H, t, J=7.2 Hz), 1.56-1.63 (2H, m), 2.37 (2H, t, J=7.2 Hz), 2.72 (2H, t, J=7.2 Hz), 2.90 (2H, t, J=7.5 Hz), 7.17-7.21 (3H, m), 7.26-7.28 (2H, m).

Ti-Activated C—C Conjugation, Aldol Reaction to Form Compound (7)

In a N$_2$ protected 100-mL flask, freshly distilled DCM (22 mL) was added. Ti(OPr)$_4$ (373 µL, 1.27 mmol) and TiCl$_4$ (377 µL, 3.44 mmol) were added in that order. The reaction solution was cooled down to −78° C. in an acetone-dry ice bath and compound (5) (1.93 g, 3.44 mmol) in DCM (6 mL) solution was added slowly. The solution was reddish and was kept at this temperature for five minutes before DIPEA (899 µL, 5.16 mmol) was added. The acetone-dry ice bath was taken away and warmed to 0° C. before an ice-water bath was used. The enolate formation was kept at 0° C. for one hour before it was re-cooled down to −78° C. in an acetone-dry ice bath. Compound (6) (1.21 mL, 6.88 mmol) was added slowly. The solution was then warm up to 0° C. and kept at this temperature via ice-water bath for one hour. The reaction was quenched by saturated $NH_4Cl$ solution (30 mL) and a diluted mixture was extracted by DCM (40 mL×3). The combined organic phase was then dried over $Na_2SO_4$ and concentrated in vacuo. The residue was loaded on the Biotage column (40S) with a gradient (8-18% EtOAc/Hex in 16 CV). A yellowish product (1.90 g, yield 75%) was collected. $R_f$=0.42 (Hex:EtOAc=3:1), RP-HPLC (betasil C18, 0.5 mL/minute, 60-100% ACN in ten minutes) 9.13 minutes, LC-MS (ESI, $MH^+$) 737.5.

Basic Hydrolysis and Lactonization to Synthesize Compound (8)

The aldol product (7) mixture (1.68 g, 2.28 mmol) was dissolved in the THF (50 mL) under a $N_2$ atmosphere. After the sample was dissolved, the solution was allowed to cool in ice-water bath for five minutes before $KOBu^t$ (1 M, 2.74 mL) was added. The reaction was kept at this temperature for 20 minutes. It was quenched with $NH_4Cl$ (50 mL) and the organic phase was diluted with EtOAc (150 mL). The aqueous phase was then separated (ensuring a pH<7) and the ether phase was washed with saturated brine (50 mL). It was then dried over $Na_2SO_4$ and concentrated under vacuo. The dried residue was then loaded on Biotage column (25 M) and purified (6-22% EtOAc/Hex in 16 CV) four times. The yellowish benzyl amine compound (8) (712.1 mg, yield 54.5%) was solidified after high vacuo drying. $R_f$=0.41 (Hex:EtOAc=3:1), RP-HPLC (betasil C18, 0.5 mL/minute, 60-100% ACN in ten minutes) 5.23 minutes, LC-MS (ESI, $MH^+$) 574.4.

Pd/C hydrogenation to synthesize (R)-3-((R)-1-(3-aminophenyl)propyl)-5,6-dihydro-4-hydroxy-6-phenethyl-6-propylpyran-2-one (9)

The benzyl amine compound (8) (265.8 mg, 0.464 mmol) was dissolved in EtOAc (6.5 mL) and MeOH (6.5 mL) mixture solution. The solution vial was bubbling $N_2$ for exchange at lease 15 minutes before catalyst addition. Stirring was stopped and the Pd/C catalyst (43 mg, 8 wt %×2) was added slowly (or in small portions). The system was evacuated and recharged with hydrogen gas (<50 psi) three times (stop stirring during vacuo). The hydrogenolysis was then kept at room temperature under 50 psi for overnight (16 hrs) to complete. After release the pressure, the reaction mixture was first checked with HPLC to see the completeness before a filtration was performed. The catalyst residue and filter paper were carefully washed with methanol. The solution was then evaporated and vacuo drying to give oil-like compound (9) (182 mg, 100% yield). No further purification is necessary. RP-HPLC (betasil C18, 0.5 mL/minute, 10-100% ACN in 8 minutes) 4.58 minutes, LC-MS (ESI, $MH^+$) 394.2.

Preparation of Compound (10) Via Swern Oxidation of mPEGn-OH

In a 250-mL flask with $N_2$ protection, DCM (105 mL) and oxalyl chloride (2M, 7.5 mL, 15 mmol) was added. The solution was cool down to −78° C. in dry-ice acetone bath for five minutes before DMSO (1.42 mL, 20.0 mmol) was added. It was stirred vigorously at this temperature for 20 minutes before a $mPEG_7$-OH (3.40 g, 10.0 mmol) and DCM (10 mL) mixture was added. The reaction was kept at this temperature for another 20 minutes before TEA (5.5 mL, 39.6 mmol) were added. The reaction was kept in dry-ice bath for three minutes and the bath was removed to gradually warm up to ambient temperature for 25 minutes. It was quenched with saturated $NaHCO_3$ (70 mL) and DCM solution was diluted (120 mL). The organic phase was separated and aqueous phase was extracted with DCM (20 mL×2). It was dried over $Na_2SO_4$ and then concentrated and a slight yellow liquid with some solid inside (2.78 g, 82% yield) was saved in $N_2$. NMR indicated a 64% conversion mixture. Biotage FCC (3-10% MeOH in DCM in 16 CV) provided pure product for reductive amination. $R_f$=0.32 (DCM:MeOH=10:1), $^1$H NMR (300 MHz, $CDCl_3$) δ 3.39 (s, 3H), 3.54-3.57 (m, 2H), 3.66 (s, 20H), 3.72-3.75 (m, 2H), 4.17 (s, 2H), 9.74 (s, 1H).

$mPEG_5$-CHO was synthesized in a similar approach. Crude product showed 86% aldehyde with 99% yield. Biotage FCC (3-10% MeOH in DCM in 16 CV) provided 75% aldehyde product with 56% yield and 15% aldehyde mixture with 25% yield. $R_f$=0.34 (DCM:MeOH=10:1), $^1$H NMR (300 MHz, $CDCl_3$) δ 3.38 (s, 3H), 3.38-3.57 (m, 2H), 3.67 (s, 11H), 3.70-3.75 (m, 3H), 4.17 (s, 2H), 9.74 (s, 1H).

Reductive Amination to Synthesize Compound (11)

Compound (9) (69.6 mg, 0.177 mmol) was dissolved in methanol (3.4 mL). While stirring, $mPEG_5$-CHO (235 mg, 75% purity, 0.708 mmol) was added dropwise. The reaction was run for 18 minutes and thereafter moved to a water bath at ambient temperature. $NaBH_4$ (54 mg, 1.42 mmol) was added in several portions. HPLC was used to check the reaction after three minutes and evidenced the reaction achieved 77% conversion. The reaction was quenched with $NaHCO_3$ (10 mL) and diluted with water and EtOAc. The organic phase was then separated and dried over $Na_2SO_4$. HPLC show the reaction has 81% conversion with 13% of starting material remaining. The solution was diluted with $NaHCO_3$ aqueous solution and extracted with DCM (30 mL×3). The combined organic solution was evaporated to provide crude sample (178 mg). It was dissolved in ACN (6 mL) and water (2 mL) and purified on AKTA (40-57% in 5 CV×2, 12.10 minutes). The acetonitrile solution of collected product was evaporated and saturated with NaCl. It was extracted with DCM (30 mL×3) and combined solution was dried over $NaSO_4$, filtrated, concentrated under vacuo. A slightly yellowish product (75.9 mg, 69% yield) was obtained with purity over 99%. RP-HPLC (betasil C18, 0.5 mL/minute, 30-100% ACN in ten minutes) 5.53 minutes, LC-MS (ESI, $MH^+$) 628.2.

This synthetic procedure was followed except $mPEG_3$-CHO was substituted for $mPEG_5$-CHO. With excess aldehyde (1.6 eq), the product mixture showed 72% of conversion after work up. AKTA purification (40-50% ACN in 3 CV, 13.2 minutes) provided 42% yield product with purity over >99%. RP-HPLC (betasil C18, 0.5 mL/minutes, 30-100% ACN in ten minutes) 5.65 minutes, LC-MS (ESI, $MH^+$) 540.3.

This synthetic procedure was followed except $mPEG_7$-CHO was substituted for $mPEG_5$-CHO. With excess aldehyde (4.5 eq), the product mixture showed 78% of conversion after work up. AKTA purification (40-57% in 5 CV) provided 73% yield of pure product (>99%). RP-HPLC (betasil C18, 0.5 mL/minute, 60-100% ACN in eight minutes) 5.06 minutes, LC-MS (ESI, $MH^+$) 716.4.

Synthesis of Compound (13a)

The above AKTA purified product (11a) (96.8 mg, 0.180 mmol) was dissolved in DCM (1.6 mL). After dissolving, the solution was cool down in an ice-water bath and trifluoropyridine sulphonyl chloride (48.6 mg, 0.198 mmol) was added.

Pyridine (44 µL, 0.54 mmol) was then added and the reaction was warm up during the overnight reaction. HPLC showed the retention time of starting material was completed and the reaction was quenched with NH$_4$Cl (10 mL). It was diluted with DCM and the separated organic phase was washed with brine. The organic phase was then dried over Na$_2$SO$_4$ and concentrated. The crude product (159.4 mg) was purified on Biotage (10-50% EtOAc in Hex with 16 CV) provided a slightly yellowish product (13a) (73.1 mg) and a less pure product (35.7 mg) with the total yield about 62%. R$_f$=0.22 (Hex:EtOAc=1:1), RP-HPLC (betasil C18, 0.5 mL/minute, 60-100% ACN in 8 minutes) 4.20 minutes, LC-MS (ESI, MH$^+$) 749.3.

Following a procedure similar to the synthesis of compound (13a), compound (11b) (154.9 mg) produced the desired product (13b) (36.0 mg, 93% pure) and a mixture of product (71.2 mg) with a yield of ~52%. Purification over Biotage silical gel column (1-7% MeOH in DCM in 16 CV). R$_f$=0.54 (EtOAc), RP-HPLC (betasil C18, 0.5 mL/minute, 60-100% ACN in 8 minutes) 4.36 minutes, LC-MS (ESI, MH$^+$) 837.4.

Following a procedure similar to the synthesis of compound (13a), compound (11c) (167.7 mg) produced the desired product (13c) (39.9 mg, 95% pure) and a mixture of product (82.3 mg) with a yield of ~50%. Purification over Biotage silical gel column (2-7% MeOH in DCM in 16 CV). R$_f$=0.25 (EtOAc), RP-HPLC (betasil C18, 0.5 mL/minute, 60-100% ACN in 8 minutes) 3.78 minutes, LC-MS (ESI, MH$^+$) 925.5.

Example 9

Evaluation of Conjugates

Following the standard procedures for evaluating activity and efficacy in cell and cell-free assays (and as set forth in, for example, Example 3), atazanavir conjugates (see Example 4), tipranivir conjugates (see Example 8) and darunavir conjugates (see Examples 5 through 7). The results are shown in the tables 2 through 8 below.

TABLE 2

Anti-HIV-1 Efficacy in CEM-SS Cells

| Compound | CEM-SS/HIV-1$_{RF}$ EC$_{50}$ (µM) | CEM-SS TC$_{50}$ (µM) | Therapeutic Index |
|---|---|---|---|
| AZT | 0.001 | >1.0 | >1000.0 |
| Atazanavir | 0.012 | 54.9 | 4578.2 |
| di-mPEG-3-Atazanavir | 0.038 | 95.7 | 2519.3 |
| di-mPEG-5-Atazanavir | 1.1 | >200.0 | >181.0 |
| di-mPEG-6-Atazanavir | 2.5 | 158.6 | 62.4 |
| di-mPEG-7-Atazanavir | 8.4 | >200.0 | >24.0 |

TABLE 3

CELL-FREE ASSAY

| Compound | IC$_{50}$ (nM) | IC$_{90}$ (nM) | IC$_{50}$ - fold change | IC$_{90}$ fold change |
|---|---|---|---|---|
| Atazanavir | 6.92 | 31.77 | 1.0 | 1.0 |
| di-mPEG-3-Atazanavir | 12.72 | 53.67 | 1.8 | 1.7 |
| di-mPEG-5-Atazanavir | 17.33 | 47.62 | 2.5 | 1.5 |
| di-mPEG-6-Atazanavir | 15.63 | 67.82 | 2.3 | 2.1 |
| di-mPEG-7-Atazanavir | 10.92 | 39.93 | 1.6 | 1.3 |

TABLE 4

CEM-SS/HIV-1RF

| Compound | EC$_{50}$ (µM) | TC$_{50}$ (µM) | Therapeutic Index | EC$_{50}$- fold change |
|---|---|---|---|---|
|  | 0.001 | >1.0 | >1000.0 |  |
| Atazanavir | 0.012 | 54.9 | 4578.2 | 1 |
| di-mPEG-3-Atazanavir | 0.038 | 95.7 | 2519.3 | 3.2 |
| di-mPEG-5-Atazanavir | 1.1 | >200.0 | >181.0 | 91.7 |
| di-mPEG-6-Atazanavir | 2.5 | 158.6 | 62.4 | 208.3 |
| di-mPEG-7-Atazanavir | 8.4 | >200.0 | >24.0 | 700 |

TABLE 5

Tipranavir Conjugates in Cell-Based Assay

| Compound | CEM-SS/HIV-1$_{RF}$ EC$_{50}$ (µM) | CEM-SS TC$_{50}$ (µM) | Therapeutic Index |
|---|---|---|---|
| AZT | 0.002 | >1.0 | >500.0 |
| Tipranavir | 0.12 | 30.6 | 263.8 |
| mPEG$_3$-amide-Tipranavir | 0.08 | 1.3 | 15.5 |
| mPEG$_5$-amide-Tipranavir | >200.0 | 12.8 | — |
| mPEG$_7$-amide-Tipranavir | >200.0 | 14.5 | — |

TABLE 6

Tipranavir Conjugates in Cell-Free Assay

| Compound | IC$_{50}$ (nM) |
|---|---|
| Saquinavir | 0.079 |
| Tipranavir | 7.2 |
| mPEG$_3$-amide-Tipranavir | — |
| mPEG$_5$-amide-Tipranavir | — |
| mPEG$_7$-amide-Tipranavir | 12.2 |

TABLE 7

Darunavir Conjugates in Cell-Based Assay

| Compound | CEM-SS/HIV-1$_{RF}$ EC$_{50}$ (µM) | CEM-SS TC$_{50}$ (µM) | Therapeutic Index |
|---|---|---|---|
| AZT | 0.005 | >1.0 | >200.0 |
| Darunavir | <0.0007 | 118.8 | >180,000.0 |
| mPEG$_3$-Darunavir | <0.0007 | 93.9 | >142,272.7 |
| mPEG$_5$-Darunavir | 0.011 | 40.7 | 3697.3 |
| mPEG$_7$-Darunavir | 0.014 | 167.6 | 11,974.9 |

TABLE 8

Darunavir Conjugates in Cell-Free Assay

| Compound | $IC_{50}$ (nM) |
|---|---|
| Darunavir | 1.5 |
| mPEG$_3$-Darunavir | 5.3 |
| mPEG$_5$-Darunavir | 1.1 |
| mPEG$_7$-Darunavir | 5.2 |
| Saquinavir | 0.001 |

What is claimed is:

1. A compound of the following Formula

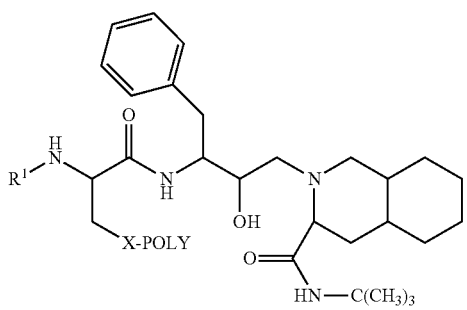

wherein:
X is a stable amide linkage;
POLY is a poly(alkylene oxide) of between 1 and 30 monomers;
and $R^1$ is benzyloxycarbonyl or 2-quinolylcarbonyl.

2. The compound of claim 1, wherein $R^1$ is benzyloxycarbonyl.

3. The compound of claim 1, wherein $R^1$ is 2-quinolylcarbonyl.

4. The compound of claim 1, wherein the poly(alkylene oxide) is a poly(ethylene oxide).

5. The compound of claim 1, wherein the water-soluble, non-peptidic oligomer is made of between 1 and 10 monomers.

6. The compound of claim 4, wherein the poly(alkylene oxide) includes an alkoxy or hydroxy end-capping moiety.

7. The compound of claim 1, wherein $R^1$ is benzyloxycarbonyl, the water-soluble, non-peptidic oligomer is a poly(ethylene oxide) made of between 1 and 10 monomers and includes a methoxy end-capping moiety, and the stable linkage is an amide.

8. The compound of claim 1, wherein $R^1$ is 2-quinolylcarbonyl, the water-soluble, non-peptidic oligomer is a poly(ethylene oxide) made of between 1 and 10 monomers and includes a methoxy end-capping moiety, and the stable linkage is an amide.

9. A composition comprising a compound of claim 1, and optionally, a pharmaceutically acceptable excipient.

10. A composition of matter comprising a compound of claim 1, wherein the compound is present in a dosage form.

11. A method of inhibiting protease activity in a subject in need thereof, the method comprising administering a compound of claim 1.

12. A compound of the following formula:

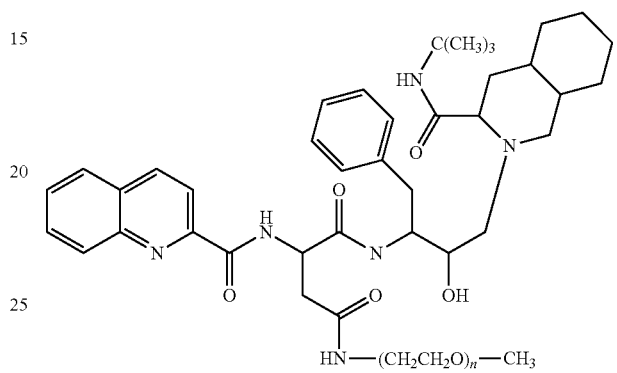

wherein n is 3.

13. A compound of the following formula:

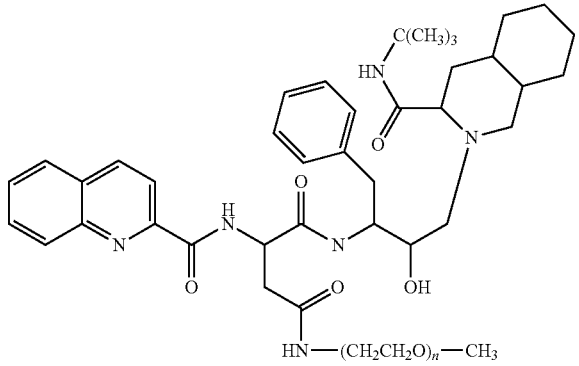

wherein n is 5.

* * * * *